(12) United States Patent
Xiang et al.

(10) Patent No.: US 7,101,912 B2
(45) Date of Patent: Sep. 5, 2006

(54) CARBIDOPA PRODRUGS AND DERIVATIVES, AND COMPOSITIONS AND USES THEREOF

(75) Inventors: Jia-Ning Xiang, Palo Alto, CA (US); Mark A. Gallop, Los Altos, CA (US); Kenneth C. Cundy, Redwood City, CA (US); Jianhua Li, Sunnyvale, CA (US); Feng Xu, Palo Alto, CA (US); Cindy X. Zhou, Palo Alto, CA (US); Laxminarayan Bhat, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 182 days.

(21) Appl. No.: 10/728,942

(22) Filed: Dec. 8, 2003

(65) Prior Publication Data

US 2004/0167216 A1   Aug. 26, 2004

Related U.S. Application Data

(60) Provisional application No. 60/431,304, filed on Dec. 6, 2002.

(51) Int. Cl.
*A61K 31/216* (2006.01)
*C07C 229/28* (2006.01)

(52) U.S. Cl. ............... 514/533; 514/538; 514/450; 514/452; 514/456; 514/466; 514/469; 514/470; 514/471; 549/229; 549/267; 549/274; 549/436; 549/438; 549/444; 549/304; 549/310; 549/292; 549/313; 558/269; 560/34

(58) Field of Classification Search .......... 560/34; 549/229, 274, 267, 436, 438, 444, 304, 310, 549/313, 292; 514/471, 450, 452, 456, 466, 514/469, 470, 533, 538; 558/269
See application file for complete search history.

(56) References Cited

U.S. PATENT DOCUMENTS

| | | | |
|---|---|---|---|
| 2,996,341 A | 8/1961 | Barry | |
| 3,139,383 A | 6/1964 | Neville | |
| 3,402,240 A | 9/1968 | Cain et al. | |
| 3,462,536 A | 8/1969 | Chemerda et al. | |
| 3,676,480 A | 7/1972 | Sletzinger et al. | |
| 3,715,382 A | 2/1973 | Karady et al. | |
| 3,746,753 A | 7/1973 | Karady et al. | |
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michaels | |
| 3,992,518 A | 11/1976 | Chien et al. | |
| 4,051,251 A | 9/1977 | Stone | |
| 4,055,645 A | 10/1977 | Scriabine | |
| 4,063,064 A | 12/1977 | Saunders et al. | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,088,864 A | 5/1978 | Theeuwes et al. | |
| 4,093,709 A | 6/1978 | Choi et al. | |
| 4,156,734 A | 5/1979 | Stone | |
| 4,200,098 A | 4/1980 | Ayer et al. | |
| 4,285,987 A | 8/1981 | Ayer et al. | |
| 4,311,706 A | 1/1982 | Bodor et al. | |
| 4,313,956 A | 2/1982 | Bodor et al. | |
| 4,421,736 A | 12/1983 | Walters | |
| 4,434,153 A | 2/1984 | Urquhart et al. | |
| 4,663,349 A | 5/1987 | Repta | |
| 4,721,613 A | 1/1988 | Urquhart et al. | |
| 4,752,470 A | 6/1988 | Mehta | |
| 4,771,073 A | 9/1988 | Repta | |
| 4,816,263 A | 3/1989 | Ayer et al. | |
| 4,820,523 A | 4/1989 | Shtohryn et al. | |
| 4,826,875 A | 5/1989 | Chiesi | |
| 4,853,229 A | 8/1989 | Theeuwes | |
| 4,873,263 A | 10/1989 | Repta | |
| 4,966,915 A | 10/1990 | Tsuchiya et al. | |
| 5,017,607 A | 5/1991 | Chiesi | |
| 5,462,933 A | 10/1995 | Kramer et al. | |
| 5,607,969 A | 3/1997 | Milman et al. | |
| 5,840,756 A | 11/1998 | Cohen et al. | |
| 6,051,576 A | 4/2000 | Ashton et al. | |
| 6,171,615 B1 | 1/2001 | Roussin et al. | |
| 6,375,987 B1 | 4/2002 | Farah et al. | |
| 6,379,700 B1 | 4/2002 | Joachim et al. | |
| 2002/0099041 A1 | 7/2002 | Gallop et al. | |

FOREIGN PATENT DOCUMENTS

| | | |
|---|---|---|
| CA | 919691 | 1/1973 |
| CA | 929483 | 7/1973 |
| CA | 951661 | 7/1974 |
| CA | 951662 | 7/1974 |

(Continued)

OTHER PUBLICATIONS

International Search Report for PCT/US03/38742, dated Mar. 30, 2004 (5 pages).
Cheng and Fung, "Dose-Dependent Pharmacokinetics of Laevodopa and its Metabolites in the Rat," *Xenobiotica*, 6(4):237-248 (1976).
Kurlan et al., "Duodenal and Gastric Delivery of Levodopa in Parkinsonism," *Ann. Neurol.*, 23(6):589-595 (1988).
Iwamoto et al., "Effect of Age on Gastrointestinal and Hepatic First-Pass Effects of levodopa in Rats," *J. Pharm. Pharmacol.*, 39:421-425 (1987).
Entry on Sinemet® in *Physicians' Desk Reference*, 56th Edition (2002).

(Continued)

*Primary Examiner*—Bernard Dentz
(74) *Attorney, Agent, or Firm*—Finnegan, Henderson, Farabow, Garrett & Dunner, LLP

(57) ABSTRACT

Prodrugs of carbidopa, derivatives of carbidopa prodrugs, methods of making prodrugs of carbidopa and derivatives thereof, methods of using prodrugs of carbidopa and derivatives thereof, and compositions of prodrugs of carbidopa and derivatives thereof are disclosed.

63 Claims, No Drawings

FOREIGN PATENT DOCUMENTS

| | | |
|---|---|---|
| CA | 956969 | 10/1974 |
| CA | 971974 | 7/1975 |
| DE | 2 062 285 | 7/1971 |
| DE | 20 62 285 A | 7/1971 |
| DE | 230 865 A1 | 12/1985 |
| DE | 240 818 | 11/1986 |
| DE | 240 818 A3 | 11/1986 |
| EP | 0 309 827 A1 | 4/1989 |
| GB | 1 261 660 A | 1/1972 |
| GB | 1 343 408 A | 1/1974 |
| JP | 60-11448 | 1/1985 |
| WO | WO 95/20567 A1 | 8/1995 |
| WO | WO 02/28882 A1 | 4/2002 |
| WO | WO 02/34237 A1 | 5/2002 |

OTHER PUBLICATIONS

Yeh et al., "Pharmacokinetics and Bioavailability of Sinemet CR: A Summary of Human Studies," *Neurology*, 39(Suppl. 2):25-38 (1989).

Sandler et al., "Variation of Levodopa Metabolism with Gastrointestinal-Absorption Site," *The Lancet*, 1(7851):238-240 (1974).

"SkyePharma's Medopar-DR approved," *Scrip*, 2233:21 (1997).

Juncos et al., "Levodopa Methyl Ester Treatment of Parkinson's Disease," *Neurology*, 37:1242-1245 (1987).

Cooper et al., "L-Dopa Esters as Potential Prodrugs: Effect on Brain Concentration of Dopamine Metabolites in Reserpinized Mice," *J. Pharm. Pharmacol.*, 39:809-818 (1987).

Graul, "The Year's New Drugs," *Drug News Perspect.*, 14(1):12-31 (2001).

Fix et al., "Short-Chain Alkyl Esters of L-Dopa as Prodrugs for Rectal Absorption," *Pharm. Res.*, 6(6):501-505 (1989).

Fix et al., "A Comparison of Oral and Rectal Absorption of L-Dopa Esters in Rats and Mice," *Pharm. Res.*, 7(4):384-387 (1990).

Leppert et al., "The Effects of Carbidopa Dose and Time and Route of Administration on Systemic L-Dopa Levels in Rats," *Pharm. Res.*, 5(9):587-591 (1988).

Contin et al., "Pharmacokinetic Optimisation in the Treatment of Parkinson's Disease," *Clin. Pharmakinet.*, 30(6):463-481 (1996).

Lu and Yu, "Dimensionless Presentation for Drug Release from a Coated Pure Drug Bead: 2. Experiment," *Int. J. Pharm.*, 112:117-124 (1994).

Felmeister, "Powders," in *Remington's Pharmaceutical Sciences*, Mack Publishing Company, Fourteenth Edition, Chapter 86, pp. 1626-1628 (1970).

Fincher, "Particle Size of Drugs and Its Relationship to Absorption and Activity," *J. Pharm. Sci.*, 57(11):1825-1835 (1968).

King and Schwartz, "Oral Solid Dosage Forms," in *Remington's Pharmaceutical Sciences*, Mack Publishing Company, Chapter 90, pp. 1603-1625 (1985).

Sefton, "Implantable Pumps," *CRC Crit. Rev. Biomed. Eng.*, 14(3):201-240 (1987).

Saudek et al., "A Preliminary Trial of the Programmable Implantable Medication System for Insulin Delivery," *N. Engl. J. Med.*, 321(9):574-579 (1989).

Langer and Peppas, "Chemical and Physical Structure of Polymers as Carriers for Controlled Release of Bioactive Agents: A Review," *J. Macromol. Sci. Rev. Macromol Chem. Phys.*, C23(1):61-126 (1983).

Levy et al., "Inhibition of Calcification of Bioprosthetic Heart Valves by Local Controlled-Release Diphosphonate," *Science*, 228:190-192 (1985).

During et al., "Controlled Release of Dopamine from a Polymeric Brain Implant: In Vivo Characterization," *Ann. Neurol.*, 25:351-356 (1989).

Howard et al, "Intracerebral Drug Delivery in Rats with Lesion-Induced Memory Deficits," *J. Neurosurg.*, 71:105-112 (1989).

Alderman, "A Review of Cellulose Ethers in Hydrophilic Matrices for Oral Controlled-Release Dosage Forms," *Int. J. Pharm. Tech. & Prod. Mfr.*, 5(3):1-9 (1984).

Bamba et al., "Release Mechanisms in Gelforming Sustained Release Preparations," *Int. J. Pharm.*, 2:307-315 (1979).

Goodson, "Dental Applications" in *Medical Applications of Controlled Release, vol. II: Applications and Evaluation*, Langer and Wise (Eds.), CRC Press, Inc., Chapter 6, pp. 115-138 (1984).

Langer, "New Methods of Drug Delivery," *Science*, 249:1527-1533 (1990).

Linhardt, "Biodegradable Polymers for Controlled Release of Drugs," in *Controlled Release of Drugs: Polymers and Aggregate Systems*, Rosoff (Ed.), VCH Publishers, Chapter 2, pp. 53-95 (1989).

Coleman et al., "Polymer Reviews: A Practical Guide to Polymer Miscibility," *Polymer*, 31:1187-1203 (1990).

Hoes and Feijen, "The Application of Drug-Polymer Conjugates in Chemotherapy," in *Horizons in Biochemistry and Biophysics, vol. 9: Drug Carrier Systems*, Roerdink and Kroon (Eds.), John Wiley & Sons, Chapter 3, pp. 57-109 (1989).

Leong and Langer, "Polymeric Controlled Drug Delivery," *Adv. Drug Delivery Rev.*, 1:199-233 (1987).

Verma et al., "Osmotically Controlled Oral Drug Delivery," *Drug Dev. Ind. Pharm.*, 26(7):695-708 (2000).

CARBIDOPA PRODRUGS AND DERIVATIVES, AND COMPOSITIONS AND USES THEREOF

This application claims priority benefit of U.S. Provisional Application No. 60/431,304 filed Dec. 6, 2002.

Embodiments of the present invention are directed to prodrugs of carbidopa and derivatives of carbidopa prodrugs, methods of making prodrugs of carbidopa and derivatives of carbidopa prodrugs, methods of using prodrugs of carbidopa and derivatives of carbidopa prodrugs, and compositions of prodrugs of carbidopa and derivatives of carbidopa prodrugs.

Parkinson's disease is a disabling, progressive illness that affects one in 1,000 people and generally occurs in people over the age of 50 years. Patients with Parkinson's disease have a deficiency of the neurotransmitter dopamine in the brain as a result of the nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can be dependent on the rate at which the drug passes through the upper gastrointestinal tract. Approximately 30–50% of the administered dose reaches the systemic circulation after oral administration. The absolute bioavailability of levodopa is dose-dependent, due to saturation of the active transport pathway (Cheng et al., 1976, Xenobiotica, 6:237–248). Plasma levels of levodopa must be carefully titrated for each patient to achieve the optimal therapeutic activity. If the concentration of levodopa is too low in plasma (and consequently in the brain) the patient can experience a return of the symptoms of Parkinson's disease (rigidity, tremor, bradykinesia). On the other hand, motor fluctuation can become a significant side effect if plasma drug levels are too high. Uncontrolled fluctuations in plasma levodopa levels can greatly contribute to the incidence of "on-off" fluctuations (diskinesias). The most effective control of Parkinsonism is observed when plasma levels of levodopa are maintained in a narrow range, for example, by continuous intraduodenal infusion (Kurlan et al., 1988, Ann. Neurol., 23:589–595).

Once absorbed, levodopa is rapidly converted to dopamine by L-aromatic amino acid decarboxylase (AADC) in the intestines and liver. It has been known that intestinal metabolism of levodopa is the major source of first pass loss of the drug. Intraportal and intravenous administration gave similar levodopa systemic exposures in rats (Iwamoto et al., 1987, J. Pharm. Pharmacol., 39:421–5). In patients, only 1% of the administered dose reaches the central nervous system intact, following transport across the blood-brain barrier by the neutral amino acid transporter. For this reason, levodopa is normally co-administered with a drug designed to inhibit its peripheral decarboxylation (e.g. carbidopa or benserazide). When administered with carbidopa, intact levodopa is transported into the central nervous system where it can be converted to dopamine. Carbidopa itself does not cross the blood-brain barrier to a significant extent, and therefore does not inhibit the required conversion of levodopa to dopamine in the brain.

The oral bioavailability of levodopa from conventional formulations of levodopa/carbidopa (e.g., Sinemet) is 84–99% (Physician's Desk Reference; Yeh et al., 1989, Neurology, 39:25–38). The half-life of levodopa in the plasma of patients is about 50 min when administered alone, or 1 to 2 hrs when given with carbidopa. For this reason, the drug must be administered three or more times per day.

A formulation of levodopa/carbidopa (Sinemet® CR) intended to provide a controlled release of both drugs is commercially available. Sinemet® CR is designed for release of both levodopa and carbidopa over a 4–6 hour period. However, absorption of levodopa is limited to the small intestine and the resulting bioavailability of levodopa from Sinemet® CR is reduced relative to the immediate release product. In most cases, Sinemet® CR must also be given more than twice per day to achieve a therapeutic level of levodopa. Conventional delayed and extended release formulations that target the large intestine are ineffective for the sustained delivery of levodopa. A simple enteric coated formulation of levodopa led to increased gastrointestinal side effects (nausea) but did not improve absorption (Sandler et al., 1974, Lancet, 16:238–240). A sustained release formulation of levodopa/carbidopa has been described that employs a swellable matrix (Geomatrix) delivery system to retain the drug in the stomach (Genta Jago product licensing information, June 1997). However, this formulation was designed to be bioequivalent to the commercially available Sinemet® CR formulation and therefore has not proven capable of providing the desired goal of a once or twice per day regimen.

The potential use of various simple esters as prodrugs of levodopa as a means to improve the pharmacokinetics of the drug has been proposed (U.S. Pat. Nos. 5,017,607; 4,826,875; 4,873,263; 4,663,349; 4,771,073; 4,311,706; Juncos et al., 1987, Neurology 37:1242; and Cooper et al., 1987, J. Pharm. Pharmacol. 39:809). An oral formulation of levodopa methyl ester (Levomet®, CHF 1301) has been described (Chiesi Pharmaceuticals). The ethyl ester of levodopa (TV-1203) is under clinical investigation as a potential therapy for Parkinsonism when co-administered with carbidopa (U.S. Pat. No. 5,607,969). A sustained cellulose formulation of levodopa ethyl ester in a mixture of hydroxypropylmethyl cellulose, hydroxypropyl cellulose, and a carboxyvinyl polymer has been described (U.S. Pat. No. 5,840,756). However, oral administration of this formulation to healthy adults pretreated with carbidopa produced a plasma levodopa terminal half-life of only 2 hr, comparable to that of Sinemet® CR. This result indicates that the ester was absorbed faster than the rate of its hydrolysis to levodopa.

A pivaloyl ester of levodopa (NB-355) has been described (European Patent No. 0309827). Conversion of the prodrug to levodopa in rat plasma following absorption from an intestinal loop was slow and sustained levels of prodrug were observed, while levels of levodopa were low. The potential for using ester prodrugs of levodopa to enhance rectal absorption of the drug has been described (U.S. Pat. Nos. 4,663,349; 4,771,073; 4,873,263). Notably, the absorption of simple alkyl esters of levodopa has been shown to be greater following rectal absorption than following oral dosing (et al., Pharm. Res. 1989, 6:501–5; et al., Pharm. Res. 1990, 4:384–7). This effect is due to the decreased abundance of esterases in the large intestine relative to the small intestine. Therefore, selective delivery of a prodrug of levodopa to the large intestine in a sustained release formulation might be expected to provide a greater oral bioavailability and a prolonged exposure to the drug.

The half-life of levodopa is prolonged and its bioavailability increased by the co-administration of carbidopa. Both drugs have relatively short half-lives ($\leq 2$ hr) (Yeh et al., 1989, Neurology, 39:25–38). Any method of sustained delivery of levodopa to the systemic circulation would therefore require a sufficient level of carbidopa to continuously inhibit peripheral decarboxylation of levodopa. In order to avoid the need for frequent (more than twice per day) dosing of carbidopa, it is necessary to deliver both levodopa and carbidopa (or prodrug thereof) in a sustained manner. It has been proposed that rectal co-administration of an AADC inhibitor such as carbidopa with an ester prodrug of levodopa would be possible as a means to decrease metabolic clearance of levodopa (U.S. Pat. Nos. 4,663,349; 4,771,073; 4,873,263). However, studies in rats have since indicated that absorption of carbidopa following rectal administration is poor (Leppert et al., 1988, Pharm. Res., 5:587–591). For this reason, a conventional sustained release formulation of carbidopa is unlikely to achieve the desired result of sustained systemic exposure.

The following publications, patents and patent applications are cited in this application as superscript numbers:

[1] Cheng, et al., Xenobiotica, 1976, 6:237–248.
[2] Contin, et al., Clin. Pharmakinet., 1996, 30:463–481.
[3] Cooper, et al., J. Pharm. Pharmacol. 1987, 39:809.
[4] Genta Jago product licensing information, June 1997.
[5] Greene et al., Protective Groups in Organic Synthesis, Third Edition, John Wiley & Sons, 1999, and references cited therein.
[6] Fix, et al., Pharm. Res., 1989, 6:501–5.
[7] Fix, et al., Pharm. Res., 1990, 4:384–7.
[8] Iwamoto, et al., J. Pharm. Pharmacol., 1987, 39:421–5.
[9] Juncos, et al., Neurology 1987, 37:1742.
[10] Kurlan, et al., Ann. Neurol., 1988, 23:589–59.
[11] Larock, Comprehensive Organic Transformations, John Wiley & Sons, Second Edition, 1999.
[12] Leppert, et al., Pharm. Res., 1988, 5:587–591.
[13] March, Advanced Organic Chemistry, John Wiley & Sons, Fourth Edition, 1992.
[14] Physician's Desk Reference.
[15] Sandler, et al., Lancet, 1974, 16:238–240.
[16] Smith, Organic Synthesis, John Wiley & Sons, 1994.
[17] Yeh, et al., Neurology, 1989, 39:25–38.
[18] "Novel dopa/dopamine prodrugs", U.S. Pat. No. 4,311,706, Jan. 19, 1982.
[19] "Rectally absorbable form of L-dopa", U.S. Pat. No. 4,663,349, May 5, 1987
[20] "Rectally absorbable form of L-dopa", U.S. Pat. No. 4,771,073, Sep. 13, 1988
[21] "Pharmaceutical compositions containing levodopa methyl ester, preparation and therapeutic applications thereof", U.S. Pat. No. 4,826,875, May 2, 1989.
[22] "Rectally absorbable form of L-dopa", U.S. Pat. No. 4,873,263, Oct. 10, 1989.
[23] "L-dopa derivatives of their acid addition salts, process for producing same and their use", U.S. Pat. No. 4,966,915, Oct. 30, 1990.
[24] "Method to treat Parkinson's disease", U.S. Pat. No. 5,017,607, May 21, 1991.
[25] "Modified bile acid conjugates, and their use as pharmaceuticals", U.S. Pat. No. 5,462,933, Oct. 31, 1995.
[26] "L-dopa ethyl ester to treat Parkinson's disease", U.S. Pat. No. 5,607,969, Mar. 4, 1997.
[27] "Pharmaceutical composition of L-DOPA ester", U.S. Pat. No. 5,840,756, Nov. 24, 1998.
[28] "Means to achieve sustained release of synergistic drugs by conjugation", U.S. Pat. No. 6,051,576, Apr. 18, 2000.
[29] "Codrugs as a method of controlled drug delivery", International Publication No. WO 95/20567, Aug. 8, 1995.
[30] U.S. Provisional Application No. 60\023,758 filed on Oct. 6, 2000.
[31] "L-Dopa Derivatives or Their Acid Addition Salts, Process for Producing Same and Their Use," European Patent No. 0 309 827, Apr. 5, 1989.
[32] "Bile acid prodrugs of L-dopa and their use in the sustained treatment of Parkinsonism," International Publication No. WO 02/28882, Apr. 11, 2002.

All of the above publications, patents and patent applications are herein incorporated by reference in their entirety to the same extent as if each individual publication, patent or patent application was specifically and individually indicated to be incorporated by reference in its entirety.

Certain embodiments of the present invention are related to prodrugs of carbidopa and derivatives of carbidopa prodrugs, which are capable of undergoing absorption across the intestinal epithelium via active and/or passive transport. In certain embodiments, carbidopa prodrugs and derivatives thereof are capable of absorption over a significant length of the gastrointestinal tract, including the large intestine (i.e., colon). Such prodrugs can be incorporated into conventional sustained release formulations (including osmotic delivery devices) to provide sustained systemic exposure to carbidopa upon oral administration to a mammal. Many of such prodrugs and derivatives can be coadministered with levodopa, or a prodrug of levodopa, and in some embodiments also formulated as sustained release compositions, with the levodopa/carbidopa prodrug compositions together providing prolonged exposure to levodopa at levels necessary to affect sustained anti-Parkinson's therapy. Certain embodiments include carbidopa prodrugs that can block first-pass levodopa decarboxylation within the intestinal enterocytes (either as the intact prodrugs themselves, or through generation of carbidopa from prodrug cleavage within the enterocytes) and which can be readily cleaved to provide carbidopa in the systemic circulation. Levodopa-carbidopa prodrug or derivative thereof or levodopa prodrug-carbidopa prodrug or derivative thereof sustained release compositions can also be administered together with inhibitors of catechol O-methyltransferase (COMT) (e.g., entacapone or tolcapone) to further block peripheral clearance of levodopa.

Among carbidopa prodrugs and derivatives thereof contemplated by certain embodiments are prodrugs and derivatives in which the terminal amino group of these drugs is blocked with an acyl or alkoxycarbonyl group. These functionalities undergo cleavage in vivo to liberate the parent drug. Optionally, the carboxyl and/or catechol moieties of carbidopa can additionally be masked with promoieties, these promoieties being cleaved either before or after cleavage of the N-terminal promoiety. Similarly, carboxyl esters and amides derived from carbidopa, which can be cleaved in vivo to release the parent drug, are contemplated as another class of prodrugs in certain embodiments. As before, the catechol moieties of such prodrugs and derivatives can also optionally be masked with promoieties, these promoieties being cleaved either before or after cleavage of the carboxy-terminal promoiety. Further contemplated by certain embodiments are carbidopa prodrugs and derivatives thereof that can initially undergo cleavage in vivo to liberate dipeptide or dipeptide analogs containing carbidopa. These dipeptides can provide the parent drug upon further proteolysis in vivo. Moreover, such prodrugs and derivatives can serve as substrates for peptide transporters localized in the intestines.

Suitable catechol protecting moieties in the aforementioned prodrugs can be elaborated by functionalizing one or more of the phenolic hydroxy groups via acylation or other appropriate methods. The corresponding esters, carbonates, and (hemi)acetals/(hemi)ketals can be cleaved in vivo to regenerate the catechol moieties of the parent drug.

One aspect provides carbidopa prodrugs and derivatives thereof of structural Formula (I):

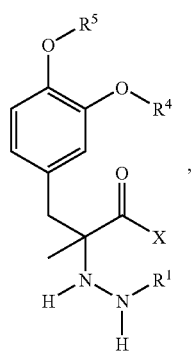
(I)

a stereoisomer thereof, an enantiomer thereof, a pharmaceutically acceptable salt thereof, a hydrate thereof, or a solvate of any of the foregoing, wherein:

X is selected from —OR$^{10}$ and moieties of Formulae (II) and (III):

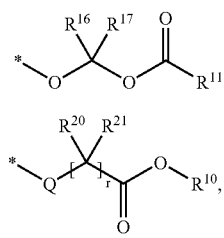
(II)

(III)

where:

r is an integer from 1 to 6;

Q is O or —NR$^{15}$;

R$^1$ is selected from hydrogen and the structure of Formula (IX):

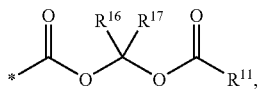
(IX)

R$^4$ and R$^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, cycloheteroalkyl, substituted cycloheteroalkyl, —C(O)OR$^{27}$, —C(O)R$^{27}$, —(CR$^{16}$R$^{17}$)OC(O)R$^{11}$, and moieties of Formulae (XVII) and (XVIII):

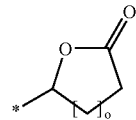
(XVII)

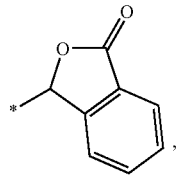
(XVIII)

wherein o is 1–3, and the cycloheteroalkyl rings in (XVII) and (XVIII) are optionally substituted with one or more groups selected from halo, CN, NO$_2$, OH, C$_{1-6}$ alkyl, and C$_{1-6}$ alkoxy;

or R$^4$ and R$^5$ together form a structure selected from Formula (XII) to (XVI):

(XII)

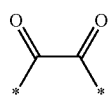
(XIII)

(XIV)

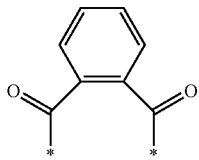
(XV)

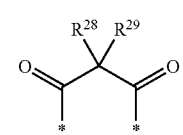
(XVI)

wherein the aryl ring in Formula (XV) is optionally substituted with one or more groups selected from halo, CN, OH, C$_{1-6}$ alkyl, C$_{1-6}$ alkoxy and —CO$_2$R$^{31}$;

R$^{10}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

R$^{11}$ is selected from hydrogen, alkyl, substituted alkyl, alkoxy, substituted alkoxy, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl, or optionally, R$^{11}$ and either R$^{16}$ or R$^{17}$, together with the atoms to which R$^{11}$ and either R$^{16}$ or R$^{17}$ are attached, form a cycloheteroalkyl or substituted cycloheteroalkyl ring, optionally to which is fused an aryl, substituted aryl, heteroaryl, substituted heteroaryl, cycloalkyl, substituted cycloalkyl, cycloheteroalkyl or substituted cycloheteroalkyl ring;

$R^{15}$ is independently selected from hydrogen, alkyl, substituted alkyl, aryl, substituted aryl, arylalkyl, and substituted arylalkyl;

$R^{16}$ and $R^{17}$ are independently selected from hydrogen, alkyl substituted alkyl, alkoxycarbonyl, substituted alkoxycarbonyl, aryl, substituted aryl, arylalkyl, substituted arylalkyl, carbamoyl, substituted carbomoyl, cycloalkyl, substituted cycloalkyl, cycloalkoxycarbonyl, substituted cycloalkoxycarbonyl, cycloheteroalkyl, substituted cycloheteroalkyl, heteroaryl, substituted heteroaryl, heteroarylalkyl, and substituted heteroarylalkyl or optionally, $R^{16}$ and $R^{17}$ together with the carbon atom to which $R^{16}$ and $R^{17}$ are attached form a cycloalkyl, substituted cycloalkyl, cycloheteroalkyl or substituted cycloheteroalkyl ring;

each $R^{20}$ and $R^{21}$ is independently selected from hydrogen, alkyl, substituted alkyl, alkoxy, substituted alkoxy, acyl, substituted acyl, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, and substituted heteroaryloxy, or optionally, when r is 1, then $R^{20}$ and $R^{21}$ together with the carbon atom to which each $R^{20}$ and $R^{21}$ is attached form a cycloalkyl, substituted cycloalkyl, cycloheteroalkyl or substituted cycloheteroalkyl ring, or optionally when $R^{20}$ and $R^{15}$ are present and are attached to adjacent atoms then $R^{15}$ and $R^{20}$ together with the atoms to which $R^{15}$ and $R^{20}$ are attached form a cycloheteroalkyl or substituted cycloheteroalkyl ring;

$R^{27}$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

with the provisos that when X is $-OR^{10}$, $R^1$ is hydrogen, and $R^4$ and $R^5$ are independently selected from hydrogen and $C_{1-19}$ alkyl, $C_{1-19}$ aryl or $C_{1-19}$ arylalkyl, then $R^{10}$ is not hydrogen or $C_{1-6}$ alkyl; and none of $R^1$, $R^4$, $R^5$, $R^{10}$, $R^{11}$, $R^{15}$, $R^{16}$, $R^{17}$, $R^{20}$, $R^{21}$, $R^{27}$, $R^{28}$, $R^{29}$, and $R^{31}$ comprise a bile acid moiety.

A second aspect provides compositions of compounds of carbidopa prodrugs and derivatives thereof. In certain embodiments, the compositions comprise a carbidopa prodrug or a derivative thereof, or an enantiomer and stereoisomer of any of the foregoing, or a pharmaceutically acceptable salt thereof, a hydrate thereof, or a solvate of any of the foregoing and a pharmaceutically acceptable diluent, carrier, excipient and/or adjuvant of any of the foregoing. The choice of diluent, carrier, excipient and/or adjuvant can depend upon, among other factors, the desired mode of administration.

A third aspect provides methods for treating Parkinson's disease. The methods comprise co-administering to a patient in need of such treatment a therapeutically effective amount of at least one of following combinations: i) levodopa and carbidopa prodrug; ii) levodopa and carbidopa derivative; iii) levodopa prodrug and carbidopa prodrug; iv) levodopa prodrug and carbidopa derivative; vi) a stereoisomer or an enantiomer of any of the foregoing; and vi) a pharmaceutically acceptable salt thereof, a hydrate thereof or a solvate of any of the foregoing, are included in the embodiments. In certain embodiments, the at least one combination is administered to the patient using a sustained-release dosage form or device.

In certain embodiments, the carbidopa prodrug or derivative thereof can be released from the dosage form or device over a period of at least 6 hours, in certain embodiments, over a period of at least 8 hours, and in certain embodiments, over a period of at least 12 hours. Further, in certain embodiments, the dosage form or device can release from 0 to 20% of the prodrug or derivative thereof in 0 to 2 hours, from 20 to 50% of the prodrug or derivative thereof in 2 to 12 hours, from 50 to 85% of the prodrug in 3 to 20 hours and greater than 75% of the prodrug or derivative thereof in 5 to 18 hours.

The oral sustained release dosage forms or devices used with certain embodiments can take any form as long as the release characteristics and pharmacokinetic profiles above are satisfied. For example, the dosage form can be in the form of an osmotic dosage form, a prodrug- or derivative-releasing polymer, prodrug- or derivative-releasing tiny timed-release pills, prodrug- or derivative-releasing lipids, prodrug- or derivative-releasing waxes and/or prodrug- or derivative-releasing beads.

A fourth aspect provides compositions for treating Parkinson's disease or hypertension in a patient in need of such treatment.

A fifth aspect provides methods for making carbidopa prodrugs and derivatives thereof, compositions of carbidopa prodrugs and derivatives thereof, methods of using carbidopa prodrugs and derivatives thereof, and methods of using compositions of carbidopa prodrugs and derivatives thereof for treating Parkinson's disease or hypertension.

SPECIFIC EMBODIMENTS

Definitions

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting form the standard deviation found in their respective testing measurements.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

"Compounds" refers to compounds encompassed by generic formulae disclosed herein, any subgenus of those generic formulae, and any specific compounds within those generic or subgeneric formulae. The compounds can be a specific specie, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure is determinative of the identity of the compound. The compounds can contain one or more chiral centers and/or double bonds and therefore, can exist as stereoisomers, such as double-bond isomers (i.e., geometric isomers), enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl; butanyls such as butan-1-yl, butan-2-yl (sec-butyl), 2-methyl-propan-1-yl (isobutyl), 2-methyl-propan-2-yl (t-butyl), cyclobutan-1-yl; and the like.

"Alkenyl" refers to an unsaturated branched, straight-chain or cyclic alkyl group having at least one carbon-carbon double bond derived by the removal of one hydrogen atom from a single carbon atom of a parent alkene. The group can be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like.

"Alkylene" refers to a saturated or unsaturated, branched, straight-chain or cyclic divalent hydrocarbon group derived by the removal of two hydrogen atoms from a parent alkane, alkene or alkyne. Typical alkylene groups include, but are not limited to methylene, ethylene, propylene, butylene; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Alkylamino" refers to a radical —NHR where R represents an alkyl or cycloalkyl group as defined herein. Representative examples include, but are not limited to, methylamino, ethylamino, 1-methylethylamino, cyclohexyl amino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical —S(O)$_2$R where R is an alkyl or cycloalkyl group as defined herein. Representative examples include, but are not limited to methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that can be optionally substituted as defined herein. Representative examples include, but are not limited to, methylthio, ethylthio, propylthio, butylthio, and the like.

"Amino" refers to the radical —NH$_2$.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms.

"Arylene" refers to a divalent aromatic hydrocarbon group derived by removal of two hydrogen atoms from a parent aromatic ring system.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C$_6$–C$_{30}$) arylalkyl, e.g., the alkanyl, alkenyl or alkynyl moiety of the arylalkyl group is (C$_1$–C$_{10}$) and the aryl moiety is (C$_6$–C$_{20}$).

"Arylalkylene" refers to a divalent acyclic alkyl group in which one of the hydrogen atoms bonded to a carbon atom, typically a terminal or sp$^3$ carbon atom is replaced with an aryl group.

"Arylalkyloxy" refers to an —O-arylalkyl group where arylalkyl is as defined herein.

"Aryloxycarbonyl" refers to a radical —C(O)—O-aryl where aryl is as defined herein.

"Bile acid moiety" refers to a moiety which has, or which includes, a structure of Formulae (A) or (B):

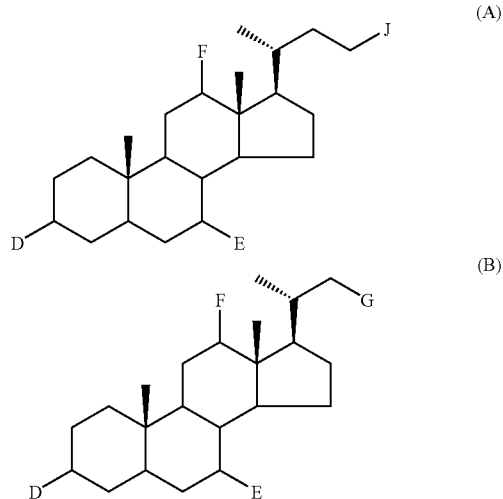

wherein each of D, E and F are independently H, OH or O—; wherein G is OH or O—; wherein J is COOH or CO—; and wherein at least one, and at most two, of D, E, F, G and J within a structure of Formulae (A) or (B) are O— or CO— and serve as point(s) of covalent bonding to another moiety or moieties.

"Carbamoyl" refers to the radical —C(O)N(R)$_2$ where each R group is independently hydrogen, alkyl, cycloalkyl or aryl as defined herein, which can be optionally substituted as defined herein.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain embodiment, the cycloalkyl group is (C$_3$–C$_{10}$) cycloalkyl, or in certain embodiments (C$_3$–C$_6$) cycloalkyl.

"Cycloheteroalkyl" refers to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" refers to a radical —C(O)—OR where R is cycloheteroalkyl is as defined herein.

"Dialkylamino" refers to a radical —NRR' where R and R' independently represent an alkyl or cycloalkyl group as defined herein. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino, and the like.

"Halo" refers to fluoro, chloro, bromo, or iodo.

"Heteroalkyloxy" refers to an —O-heteroalkyl group where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O', —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, wherein R' is hydrogen, alkyl, substituted alkyl, cycloalkyl, substituted cycloalkyl, aryl or substituted aryl.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is between 5–20 membered heteroaryl, and in other embodiments is between 5–10 membered heteroaryl. In certain embodiments heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined herein.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In certain embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl.

"Leaving group" has the meaning conventionally associated with it in synthetic organic chemistry, i.e., an atom or a group capable of being displaced by a nucleophile and includes halo (such as chloro, bromo, and iodo), acyloxy (e.g., acetoxy, benzoyloxy), mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine and the like.

"Pharmaceutically acceptable vehicle" refers to a diluent, adjuvant, excipient or carrier with which a compound is administered.

"Extended release" refers to dosage forms that provide for the delayed, slowed, over a period of time, continuous, discontinuous, or sustained release of the compounds.

"Patient" includes mammals and humans. The terms "human" and "patient" are used interchangeably herein.

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —$R^{33}$, —O$^-$, =O, —O$R^{33}$, —S$R^{33}$, —S$^-$, =S, —N$R^{33}R^{34}$, =N$R^{33}$, —C$X_3$, —C$F_3$, —CN, —OCN, —SCN, —NO, —NO$_2$, =N$_2$, —N$_3$, —S(O)$_2$O$^-$, —S(O)$_2$OH, —S(O)$_2R^{33}$, —OS(O)$_2$O$^-$, —OS(O)$_2R^{33}$, —P(O)(O$^-$)$_2$, —P(O)(O$R^{33}$)(O$^-$), —OP(O)(O$R^{33}$)(O$R^{34}$), —C(O)$R^{33}$, —C(S)$R^{33}$, —C(O)O$R^{33}$, —C(O)N$R^{33}R^{34}$, —C(O)O$^-$, —C(S)O$R^{33}$, —N$R^{35}$C(O)N$R^{33}R^{34}$, —N$R^{35}$C(S)N$R^{33}R^{34}$, —N$R^{35}$C(N$R^{33}$)N$R^{33}R^{34}$ and —C(N$R^{33}$)N$R^{33}R^{34}$, where each X is independently a halogen; each $R^{33}$ and $R^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{35}R^{36}$, —C(O)$R^{35}$ or —S(O)$_2R^{35}$ or optionally $R^{33}$ and $R^{34}$ together with the atom to which they are both attached form a cycloheteroalkyl or substituted cycloheteroalkyl ring; and $R^{35}$ and $R^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Treating" or "treatment" of any disease or disorder refers to arresting or ameliorating a disease or disorder, reducing the risk of acquiring a disease or disorder, reducing the development of a disease or disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibit at least one physical parameter which may not be discernible to the patient. Further, "treating" or "treatment" refers to delaying the onset of the disease or disorder or at least symptoms thereof in a patient which may be exposed to or predisposed to a disease or disorder even though that patient does not yet experience or display symptoms of the disease or disorder.

"Therapeutically effective amount" refers to the amount of a compound that, when administered to a patient for treating a disease or disorder, is sufficient to affect such treatment for the disease or disorder. The "therapeutically effective amount" will vary depending on the compound, the disease or disorder and its severity and the age and weight of the patient to be treated.

"Cleave" refers to breakage of chemical bonds and is not limited to chemical or enzymatic reactions or mechanisms unless clearly indicated by the context.

Thus, the development of levodopa prodrugs and/or carbidopa prodrugs and derivatives thereof that can be efficiently absorbed throughout the gastrointestinal tract, including the colon, is highly desirable.

Reference will now be made in detail to certain embodiments.

Compounds

Compounds include carbidopa prodrugs and other derivatives to which promoieties have been attached. In certain embodiments, compounds include carbidopa derivatives of Formula (I):

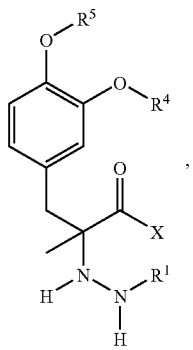

(I)

a stereoisomer thereof, an enantiomer thereof, a pharmaceutically acceptable salt thereof, a hydrate thereof, or a solvate of any of the foregoing, wherein:

X is selected from —OR$^{10}$ and moieties of Formulae (II) and (III):

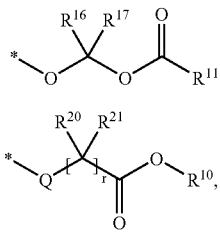

where:
r is an integer from 1 to 6;
Q is O or —NR$^{15}$;

R$^1$ is selected from hydrogen and the structure of Formula (IX):

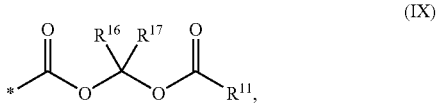

R$^4$ and R$^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, cycloheteroalkyl, substituted cycloheteroalkyl, —C(O)OR$^{27}$, —C(O)R$^{27}$, —(CR$^{16}$R$^{17}$)OC(O)R$^{11}$, and moieties of Formulae (XVII) and (XVIII):

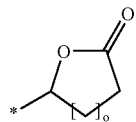

(XVII)

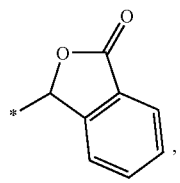

(XVIII)

wherein o is 1–3, and the cycloheteroalkyl rings in (XVII) and (XVIII) are optionally substituted with one or more groups selected from halo, CN, NO$_2$, OH, C$_{1-6}$ alkyl, and C$_{1-6}$ alkoxy;

or R$^4$ and R$^5$ together form a structure selected from Formulae (XII) to (XVI):

(XII)

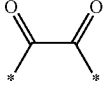

(XIII)

(XIV)

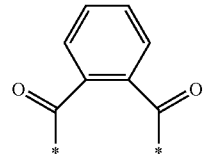

(XV)

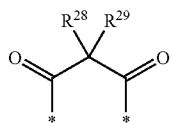

(XVI)

wherein the aryl ring in Formula (XV) is optionally substituted with one or more groups selected from halo, CN, OH, $C_{1-6}$ alkyl, $C_{1-6}$ alkoxy, and —$CO_2R^{31}$;

$R^{10}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{11}$ is selected from hydrogen, alkyl, substituted alkyl, alkoxy, substituted alkoxy, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl, or optionally, $R^{11}$ and either $R^{16}$ or $R^{17}$, together with the atoms to which $R^{11}$ and either $R^{16}$ or $R^{17}$ are attached, form a cycloheteroalkyl or substituted cycloheteroalkyl ring, optionally to which is fused an aryl, substituted aryl, heteroaryl, substituted heteroaryl, cycloalkyl, substituted cycloalkyl, cycloheteroalkyl or substituted cycloheteroalkyl ring;

$R^{15}$ is independently selected from hydrogen, alkyl, substituted alkyl, aryl, substituted aryl, arylalkyl, and substituted arylalkyl;

$R^{16}$ and $R^{17}$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbomoyl, cycloalkyl, substituted cycloalkyl, cycloalkoxycarbonyl, substituted cycloalkoxycarbonyl, cycloheteroalkyl, substituted cycloheteroalkyl, heteroaryl, substituted heteroaryl, heteroarylalkyl, and substituted heteroarylalkyl or optionally, $R^{16}$ and $R^{17}$ together with the carbon atom to which $R^{16}$ and $R^{17}$ are attached form a cycloalkyl, substituted cycloalkyl, cycloheteroalkyl or substituted cycloheteroalkyl ring;

each $R^{20}$ and $R^{21}$ is independently selected from hydrogen, alkyl, substituted alkyl, alkoxy, substituted alkoxy, acyl, substituted acyl, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, and substituted heteroaryloxy, or optionally, when r is 1, then $R^{20}$ and $R^{21}$ together with the carbon atom to which each $R^{20}$ and $R^{21}$ is attached form a cycloalkyl, substituted cycloalkyl, cycloheteroalkyl or substituted cycloheteroalkyl ring, or optionally when $R^{20}$ and $R^{15}$ are present and are attached to adjacent atoms then $R^{15}$ and $R^{20}$ together with the atoms to which $R^{15}$ and $R^{20}$ are attached form a cycloheteroalkyl or substituted cycloheteroalkyl ring;

$R^{27}$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

with the provisos that when X is —$OR^{10}$, $R^1$ is hydrogen, and $R^4$ and $R^5$ are independently selected from hydrogen and $C_{1-19}$ alkyl, $C_{1-19}$ aryl or $C_{1-19}$ arylalkyl, then $R^{10}$ is not hydrogen or $C_{1-6}$ alkyl; and none of $R^1$, $R^4$, $R^5$, $R^{10}$, $R^{11}$, $R^{15}$, $R^{16}$, $R^{17}$, $R^{20}$, $R^{21}$, $R^{27}$, $R^{28}$, $R^{29}$, and $R^{31}$ comprise a bile acid moiety.

In certain embodiments, the compounds are represented by Formula (Ia) shown below:

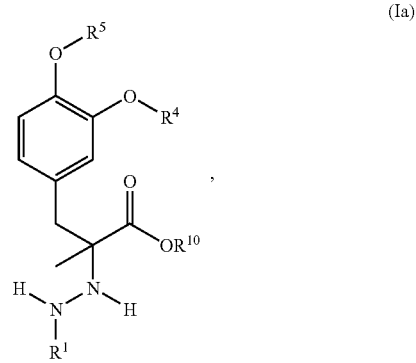

(Ia)

and stereoisomers thereof, enantiomers thereof, pharmaceutically acceptable salts thereof, hydrates thereof, or solvates of any of the foregoing, wherein:

$R^1$ is selected from hydrogen, and the structure of Formula (IX):

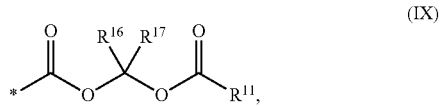

(IX)

$R^4$ and $R^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, cycloheteroalkyl, substituted cycloheteroalkyl, —C(O)$R^{27}$, —C(O)$R^{27}$, —(C$R^{16}R^{17}$)OC(O)$R^{11}$, and moieties of Formulae (XVII) and (XVIII):

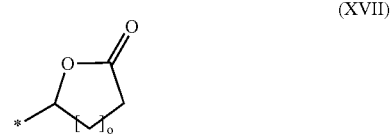

(XVII)

-continued

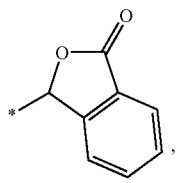
(XVIII)

wherein o is 1–3, and the cycloheteroalkyl rings in (XVII) and (XVIII) are optionally substituted with one or more groups selected from halo, CN, $NO_2$, OH, $C_{1-6}$ alkyl, and $C_{1-6}$ alkoxy;

or $R^4$ and $R^5$ together form a structure selected from Formulae (XII) to (XVI):

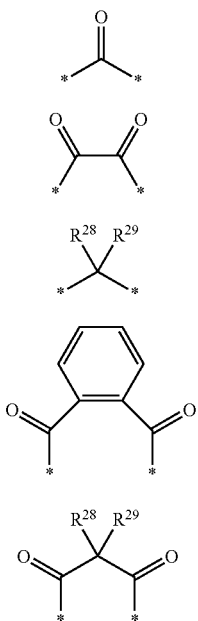

(XII)

(XIII)

(XIV)

(XV)

(XVI)

wherein the aryl ring in Formula (XV) is optionally substituted with one or more groups selected from halo, CN, OH, $C_{1-6}$ alkyl, $C_{1-6}$ alkoxy, and $-CO_2R^{31}$;

$R^{10}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{11}$ is selected from hydrogen, alkyl, substituted alkyl, alkoxy, substituted alkoxy, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, alkoxy, heteroaryl, substituted heteroaryl, heteroarylalkyl, and substituted heteroarylalkyl, or optionally, $R^{11}$ and either $R^{16}$ or $R^{17}$, together with the atoms to which $R^{11}$ and either $R^{16}$ or $R^{17}$ are attached, form a cycloheteroalkyl or substituted cycloheteroalkyl ring, optionally to which is fused an aryl, substituted aryl, heteroaryl, substituted heteroaryl, cycloalkyl, substituted cycloalkyl, cycloheteroalkyl or substituted cycloheteroalkyl ring;

$R^{16}$ and $R^{17}$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroarylalkyl, and substituted heteroarylalkyl or optionally, $R^{16}$ and $R^{17}$ together with the carbon atom to which they are attached form a cycloalkyl, substituted cycloalkyl, cycloheteroalkyl or substituted cycloheteroalkyl ring;

$R^{27}$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, heteroaryl, heteroarylalkyl, and substituted heteroarylalkyl;

with the provisos that when $R^1$ is hydrogen, and $R^4$ and $R^5$ are independently selected from hydrogen, $C_{1-19}$ alkyl, $C_{1-19}$ aryl or $C_{1-19}$ arylalkyl, then $R^{10}$ is not hydrogen or $C_{1-6}$ alkyl; and none of $R^1$, $R^4$, $R^5$, $R^{10}$, $R^{11}$, $R^{15}$, $R^{16}$, $R^{17}$, $R^{27}$, $R^{28}$, $R^{29}$, and $R^{31}$ comprises a bile acid moiety.

In certain embodiments of a compound of Formula (Ia):
$R^4$ and $R^5$ are independently moieties having the structures of Formulae (XVII) and (XVIII):

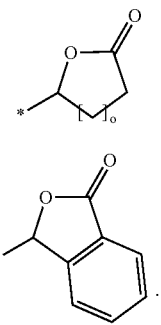

(XVII)

(XVIII)

In certain embodiments of a compound of Formula (Ia), $R^1$ is hydrogen.

In certain embodiments of a compound of Formula (Ia), $R^1$ is a moiety comprising Formula (IX).

In certain embodiments of a compound of Formula (Ia), $R^4$ and $R^5$ are independently selected from hydrogen, alkanyl, substituted alkanyl, arylalkanyl, substituted arylalkanyl, heteroarylalkanyl, substituted heteroarylalkanyl, cycloalkanyl, substituted cycloalkanyl, cycloheteroalkanyl, and substituted cycloheteroalkanyl. In certain embodiments of a compound of Formula (Ia), $R^4$ and $R^5$ are independently selected from hydrogen, methyl, ethyl, propyl, isopropyl, butyl, isobutyl, sec-butyl, tert-butyl, cyclopropyl, cyclobutyl, cyclopentyl, cyclohexyl, benzyl, and pyridyl, where the aryl rings of the benzyl and pyridyl groups are optionally substituted with one or more substituents selected from halo, CN, $NO_2$, OH, $C_{1-6}$ alkyl, $C_{1-6}$ alkoxy, and $-CO_2R^{31}$.

In certain embodiments of a compound of Formula (Ia), $R^4$ and $R^5$ are independently selected from hydrogen, —C(O)OR$^{27}$, and —C(O)R$^{27}$. In certain embodiments, R$^4$ and R$^5$ are both independently —C(O)OR$^{27}$ or —C(O)R$^{27}$. In certain embodiments, R$^{27}$ is selected from C$_{1-10}$ alkyl, substituted C$_{1-10}$ alkyl, C$_{5-8}$ aryl, substituted C$_{5-8}$ aryl, C$_{6-10}$ arylalkyl, and substituted C$_{6-10}$ arylalkyl.

In certain embodiments, R$^{27}$ is selected from alkanyl, substituted alkanyl, cycloalkanyl, substituted cycloalkanyl, arylalkanyl, substituted arylalkanyl, heteroarylalkanyl and substituted heteroarylalkanyl. In certain embodiments, R$^{27}$ is selected from methyl, ethyl, propyl, isopropyl, butyl, isobutyl, sec-butyl, tert-butyl, cyclopropyl, cyclobutyl, cyclopentyl, cyclohexyl, and benzyl where the aryl ring of the benzyl group is optionally substituted with one or more substituents selected from halo, CN, NO$_2$, OH, C$_{1-6}$ alkyl, C$_{1-6}$ alkoxy, and —CO$_2$R$^{31}$.

In certain embodiments, R$^{27}$ is selected from aryl, substituted aryl, heteroaryl, and substituted heteroaryl. In certain embodiments, R$^{27}$ is selected from phenyl, pyridyl, furyl, and thienyl, the aromatic rings of which are optionally substituted with one or more substituents selected from halo, CN, NO$_2$, OH, C$_{1-6}$ alkyl, C$_{1-6}$ alkoxy, and —CO$_2$R$^{31}$.

In certain embodiments, R$^{27}$ is selected from C$_{1-10}$ alkyl, substituted C$_{1-10}$ alkyl, C$_{5-8}$ aryl, substituted C$_{5-8}$ aryl, C$_{6-10}$ arylalkyl, and substituted C$_{6-10}$ arylalkyl.

In certain embodiments of a compound of Formula (Ia), R$^4$ and R$^5$ are independently selected from hydrogen, and —(CR$^{16}$R$^{17}$)OC(O)R$^{11}$. In certain embodiments, R$^4$ and R$^5$ are both independently —(CR$^{16}$R$^{17}$)OC(O)R$^{11}$.

In certain embodiments of a compound of Formula (Ia), R$^4$ and R$^5$ are independently selected from —(CR$^{16}$R$^{17}$)OC(O)R$^{11}$R$^{11}$, and —(CR$^{16}$R$^{17}$)OC(O)R$^{11}$ wherein R$^{11}$ is selected from hydrogen, C$_{1-10}$ alkyl, substituted C$_{1-10}$ alkyl, C$_{5-8}$ aryl, substituted C$_{5-8}$ aryl, C$_{1-15}$ alkoxy, and substituted C$_{1-15}$ alkoxy.

In certain embodiments of a compound of Formula (Ia), R$^4$ and R$^5$ are independently selected from —(CR$^{16}$R$^{17}$)OC(O)R$^{11}$R$^{11}$, and —(CR$^{16}$R$^{17}$)OC(O)R$^{11}$ wherein R$^{16}$ and R$^{17}$ are independently selected from hydrogen, C$_{1-16}$ alkyl, substituted C$_{1-16}$ alkyl, C$_{5-8}$ aryl, substituted C$_{5-8}$ aryl, C$_{6-10}$ arylalkyl, and substituted C$_{6-10}$ arylalkyl.

In certain embodiments of a compound of Formula (Ia), R$^4$ and R$^5$ together with the atoms to which they are attached are incorporated into a benzo-fused heterocyclic ring of Formula (XIV).

In certain embodiments of a compound of Formula (Ia), R$^{10}$ is selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, heteroarylalkanyl, and substituted heteroarylalkanyl. In certain embodiments, R$^{10}$ is selected from hydrogen, methyl, ethyl, propyl, isopropyl, butyl, isobutyl, sec-butyl, tert-butyl, cyclopropyl, cyclobutyl, cyclopentyl, cyclohexyl, phenoxyethyl, carboxymethyl, carboxyethyl, carboxypropyl, carboxybutyl, and benzyl, all of which are optionally substituted with one or more substituents selected from halo, CN, NO$_2$, OH, C$_{1-6}$ alkyl, C$_{1-6}$ alkoxy, and —CO$_2$R$^{31}$.

In certain embodiments of a compound of Formula (Ia), R$^{10}$ is selected from hydrogen, aryl, substituted aryl, heteroaryl, and substituted heteroaryl. In certain embodiments, R$^{10}$ is selected from phenyl and substituted phenyl, where the one or more substituents are selected from halo, CN, NO$_2$, OH, C$_{1-6}$ alkyl, C$_{1-6}$ alkoxy, and —CO$_2$R$^{31}$.

In certain embodiments of a compound of Formula (Ia), R$^{10}$ is selected from C$_{1-10}$ alkyl, substituted C$_{1-10}$ alkyl, C$_{5-8}$ aryl, substituted C$_{5-8}$ aryl, —R$^{32}$OC(O)R$^{37}$, and —R$^{32}$OC(O)OR$^{37}$, where where R$^{32}$ is selected from C$_{1-10}$ alkylene, substituted C$_{1-10}$ alkylene, C$_{5-8}$ arylene, substituted C$_{5-8}$ arylene, C$_{6-10}$ arylalkylene, and substituted C$_{6-10}$ arylalkylene, and R$^{37}$ is selected from C$_{1-10}$ alkyl, substituted C$_{1-10}$ alkyl, C$_{5-8}$ aryl, substituted C$_{5-8}$ aryl, C$_{6-10}$ arylalkyl, and substituted C$_{6-10}$ arylalkyl.

In certain embodiments of a compound of Formula (Ia), R$^{11}$ is selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, heteroarylalkanyl, and substituted heteroarylalkanyl. In certain embodiments, R$^{11}$ is selected from methyl, ethyl, propyl, isopropyl, butyl, isobutyl, sec-butyl, tert-butyl, cyclopropyl, cyclobutyl, cyclopentyl, cyclohexyl, and styryl, where the aryl ring of the styryl group is optionally substituted with one or more substituents selected from halo, CN, NO$_2$, OH, C$_{1-6}$ alkyl, C$_{1-6}$ alkoxy, and —CO$_2$R$^{31}$.

In certain embodiments of a compound of Formula (Ia), R$^{11}$ is selected from aryl, substituted aryl, heteroaryl, and substituted heteroaryl. In certain embodiments, R$^{11}$ is selected from phenyl, pyridyl, indolyl, furyl, imidazolyl and oxazolyl, the aromatic rings of which are optionally substituted with one or more substituents selected from halo, CN, NO$_2$, OH, C$_{1-6}$ alkyl, C$_{1-6}$ alkoxy, and —CO$_2$R$^{31}$.

In certain embodiments of a compound of Formula (Ia), R$^{11}$ is selected from hydrogen, C$_{1-10}$ alkyl, substituted C$_{1-10}$ alkyl, C$_{5-8}$ aryl, substituted C$_{5-8}$ aryl, C$_{1-15}$ alkoxy, and substituted C$_{1-15}$ alkoxy.

In certain embodiments of a compound of Formula (Ia), R$^{11}$ is selected from methoxy, ethoxy, propoxy, isopropoxy, butoxy, isobutoxy, sec-butoxy, tert-butoxy, pentyloxy, hexyloxy, cyclopropoxy, cyclobutoxy, cyclopentyloxy, cyclohexyloxy, 2,6-dimethylcyclohexyloxy, fenchyloxy, and adamantyloxy.

In certain embodiments of a compound of Formula (Ia), R$^{11}$ and either R$^{16}$ or R$^{17}$, together with the atoms to which R$^{11}$ and either R$^{16}$ or R$^{17}$ are attached, form a cycloalkyl, substituted cycloalkyl, cycloheteroalkyl or substituted cycloheteroalkyl ring, optionally to which is fused an aryl, substituted aryl, heteroaryl or substituted heteroaryl ring.

In certain embodiments of a compound of Formula (Ia), R$^{16}$ and R$^{17}$ are independently selected from hydrogen, alkanyl, substituted alkanyl, cycloalkanyl, aryl, substituted aryl, heteroaryl, substituted heteroaryl, arylalkanyl, and substituted arylalkanyl. In certain embodiments, R$^{16}$ and R$^{17}$ are independently selected from hydrogen, methyl, ethyl, propyl, isopropyl, butyl, isobutyl, sec-butyl, tert-butyl, cyclopropyl, cyclobutyl, cyclopropyl, cyclobutyl, cyclopentyl, cyclohexyl, phenyl, and benzyl, where the aryl ring of the phenyl and the benzyl groups is optionally substituted with one or more substituents selected from halo, CN, NO$_2$, OH, C$_{1-6}$ alkyl, C$_{1-6}$ alkoxy, and —CO$_2$R$^{31}$.

In certain embodiments of a compound of Formula (Ia), R$^{16}$ and R$^{17}$ together with the carbon atom to which they are attached form a cycloalkanyl, substituted cycloalkanyl, cycloheteroalkanyl or substituted cycloheteroalkanyl ring. In certain embodiments, R$^{16}$ and R$^{17}$ together with the carbon atom to which they are attached form a cyclopropyl, cyclobutyl, cyclopentyl or cyclohexyl ring.

In certain embodiments of a compound of Formula (Ia), R$^{16}$ and R$^{17}$ are independently selected from hydrogen, C$_{1-6}$ alkyl, substituted C$_{1-6}$ alkyl, C$_{5-8}$ aryl, substituted C$_{5-8}$ aryl, C$_{6-10}$ arylalkyl, and substituted C$_{6-10}$ arylalkyl.

In certain embodiments of a compound of Formula (Ia), R$^{28}$ and R$^{29}$ are independently selected from hydrogen, alkanyl, aryl, and alkoxycarbonyl. In certain embodiments, R$^{28}$ and R$^{29}$ are independently selected from hydrogen, methyl, ethyl, phenyl, methoxycarbonyl, and ethoxycarbonyl. In certain embodiments, $R^{38}$ and $R^{39}$ are both hydrogen.

In certain embodiments of a compound of Formula (Ia), $R^{31}$ is hydrogen or $C_{1-8}$ alkyl or cycloalkyl. In certain embodiments, $R^{31}$ is hydrogen, methyl, ethyl, propyl, isopropyl, butyl, isobutyl, sec-butyl, tert-butyl, cyclopropyl, cyclobutyl, cyclopentyl or cyclohexyl.

In certain embodiments of a compound of Formula (Ia), $R^1$ is hydrogen, and $R^{10}$ is selected from $C_{7-10}$ alkyl, substituted $C_{7-10}$ alkyl, $C_{5-8}$ aryl, substituted $C_{5-8}$ aryl, —$R^{32}$OC(O)$R^{37}$, and —$R^{32}$OC(O)O$R^{37}$, where $R^{32}$ is selected from $C_{1-10}$ alkylene, substituted $C_{1-10}$ alkylene, $C_{5-8}$ arylene, substituted $C_{5-8}$ arylene, $C_{6-10}$ arylalkylene, and substituted $C_{6-10}$ arylalkylene, and $R^{37}$ is selected from $C_{1-10}$ alkyl, substituted $C_{1-10}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formula (Ia), $R^1$ is a moiety of Formula (IX), and $R^{10}$ is selected from $C_{7-10}$ alkyl, substituted $C_{7-10}$ alkyl, $C_{5-8}$ aryl, substituted $C_{5-8}$ aryl, —$R^{32}$OC(O)$R^{37}$, and —$R^{32}$OC(O)O$R^{37}$, where $R^{32}$ is selected from $C_{1-10}$ alkylene, substituted $C_{1-10}$ alkylene, $C_{5-8}$ arylene, substituted $C_{5-8}$ arylene, $C_{6-10}$ arylalkylene, and substituted $C_{6-10}$ arylalkylene, and $R^{37}$ is selected from $C_{1-10}$ alkyl, substituted $C_{1-10}$ alkyl, $C_{5-8}$ aryl, substituted $C_{5-8}$ aryl, $C_{6-10}$ arylalkyl, and substituted $C_{6-10}$ arylalkyl.

In certain embodiments, compounds of Formula (I) are represented by Formulae (Ib) or (Ic) below:

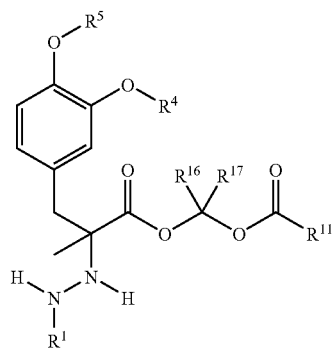
(Ib)

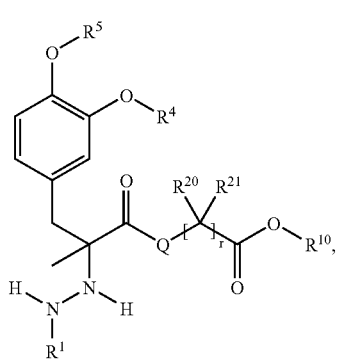
(Ic)

and stereoisomers thereof, enantiomers thereof, pharmaceutically acceptable salts thereof, hydrates thereof, or solvates of any of the foregoing, wherein:

Q is O or —NR$^{15}$;

r is an integer from 1 to 6;

$R^1$ is selected from hydrogen, and a moiety of Formula (IX):

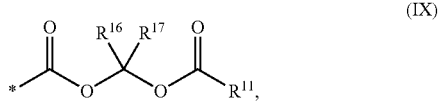
(IX)

$R^4$ and $R^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, —C(O)R$^{27}$, —C(O)R$^{27}$, —(CR$^{16}$R$^{17}$)OC(O)R$^{11}$, and moieties of Formulae (XVII) and (XVIII):

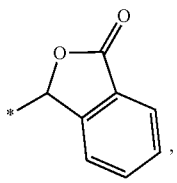
(XVII)

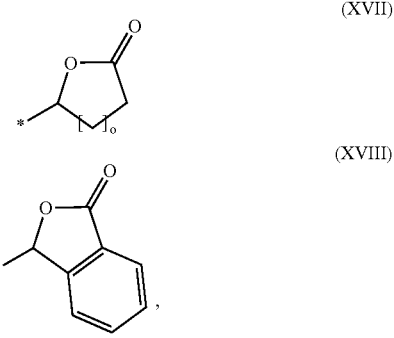
(XVIII)

wherein o is 1–3, and the cycloheteroalkyl rings in (XVII) and (XVIII) are optionally substituted with one or more groups selected from halo, CN, NO$_2$, OH, C$_{1-6}$ alkyl, and C$_{1-6}$ alkoxy;

or $R^4$ and $R^5$ are independently moieties having the structures of Formulae (XII) to (XVI):

(XII)

(XIII)

(XIV)

(XV)

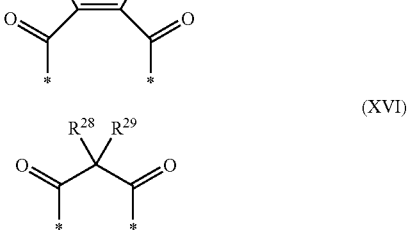
(XVI)

wherein the aryl ring in Formula (XV) is optionally substituted with one or more groups selected from halo, CN, OH, C$_{1-6}$ alkyl, C$_{1-6}$ alkoxy, and —CO$_2$R$^{31}$;

$R^{10}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{11}$ is selected from hydrogen, alkyl, substituted alkyl, alkoxy, substituted alkoxy, aryl, substituted aryl, aryloxy, substituted aryloxy, arylalkyl, substituted arylalkyl, cycloalkyl, substituted cycloalkyl, cycloalkyloxy, substituted cycloalkyloxy, heteroalkyl, substituted heteroalkyl, cycloheteroalkyl, substituted cycloheteroalkyl, heteroaryl, substituted heteroaryl, heteroarylalkyl, and substituted heteroarylalkyl, or optionally, $R^{11}$ and either $R^{16}$ or $R^{17}$, together with the atoms to which $R^{11}$ and either $R^{16}$ or $R^{17}$ are attached, form a cycloheteroalkyl or substituted cycloheteroalkyl ring, optionally to which is fused an aryl, substituted aryl, heteroaryl, substituted heteroaryl, cycloalkyl, substituted cycloalkyl, cycloheteroalkyl or substituted cycloheteroalkyl ring;

$R^{15}$ is selected from hydrogen, alkyl, substituted alkyl, aryl, substituted aryl, arylalkyl, and substituted arylalkyl;

$R^{16}$ and $R^{17}$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroarylalkyl, and substituted heteroarylalkyl or optionally, $R^{16}$ and $R^{17}$ together with the carbon atom to which they are attached form a cycloalkyl, substituted cycloalkyl, cycloheteroalkyl or substituted cycloheteroalkyl ring;

each $R^{20}$ and $R^{21}$ is independently selected from hydrogen, alkyl, substituted alkyl, alkoxy, substituted alkoxy, acyl, substituted acyl, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, and substituted heteroaryloxy, or optionally, when r is 1, then $R^{20}$ and $R^{21}$ together with the carbon atom to which they are attached form a cycloalkyl, substituted cycloalkyl, cycloheteroalkyl or substituted cycloheteroalkyl ring, or optionally when $R^{20}$ and $R^{15}$ are present and are attached to adjacent atoms then $R^{15}$ and $R^{20}$ together with the atoms to which they are attached form a cycloheteroalkyl or substituted cycloheteroalkyl ring;

$R^{27}$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

with the proviso that none of $R^1$, $R^4$, $R^5$, $R^{10}$, $R^{11}$, $R^{15}$, $R^{16}$, $R^{17}$, $R^{20}$, $R^{21}$, $R^{27}$, $R^{28}$, $R^{29}$, and $R^{31}$ comprise a bile acid moiety.

In certain embodiments of a compound of Formulae (Ib) or (Ic), $R^4$ and $R^5$ are independently selected moieties from Formulae (XVII), and (XVIII).

In certain embodiments of a compound of Formula (Ic), Q is O.

In certain embodiments of a compound of Formula (Ic), Q is —$NR^{15}$.

In certain embodiments of a compound of Formulae (Ib) or (Ic), $R^1$ is hydrogen.

In certain embodiments of a compound of Formulae (Ib) or (Ic), $R^1$ is a moiety of Formula (IX).

In certain embodiments of a compound of Formulae (Ib) or (Ic), $R^4$ and $R^5$ are independently selected from hydrogen, alkanyl, substituted alkanyl, arylalkanyl, substituted arylalkanyl, heteroarylalkanyl, substituted heteroarylalkanyl, cycloalkanyl, substituted cycloalkanyl, cycloheteroalkanyl, and substituted cycloheteroalkanyl. In certain embodiments, $R^4$ and $R^5$ are independently selected from hydrogen, methyl, ethyl, propyl, isopropyl, butyl, isobutyl, sec-butyl, tert-butyl, cyclopentyl, cyclohexyl, benzyl, and pyridyl, where the aryl rings of the benzyl and pyridyl groups are optionally substituted with one or more substituents selected from halo, CN, $NO_2$, OH, $C_{1-6}$ alkyl, $C_{1-6}$ alkoxy, and —$CO_2R^{31}$.

In certain embodiments of a compound of Formulae (Ib) or (Ic), $R^4$ and $R^5$ are independently selected from hydrogen, —$C(O)OR^{27}$, and —$C(O)R^{27}$. In certain embodiments of a compound of Formulae (Ib) or (Ic), $R^4$ and $R^5$ are independently selected from hydrogen, —$C(O)OR^{27}$, and —$C(O)OR27$, wherein $R^{27}$ is selected from $C_{1-10}$ alkyl, substituted $C_{1-10}$ alkyl, $C_{5-8}$ aryl, $C_{5-8}$ substituted aryl, $C_{6-10}$ arylalkyl, and substituted $C_{6-10}$ arylalkyl.

In certain embodiments, $R^4$ and $R^5$ are both independently —$C(O)OR^{27}$ or —$C(O)R^{27}$. In certain embodiments, $R^4$ and $R^5$ are both independently —$C(O)OR^{27}$ or —$C(O)R^{27}$ where $R^{27}$ is selected from $C_{1-10}$ alkyl, substituted $C_{1-10}$ alkyl, $C_{5-8}$ aryl, $C_{5-8}$ substituted aryl, $C_{6-10}$ arylalkyl, and substituted $C_{6-10}$ arylalkyl.

In certain embodiments, $R^4$ and $R^5$ are both independently —$C(O)OR^{27}$ or —$C(O)R^{27}$ where $R^{27}$ is selected from alkanyl, substituted alkanyl, cycloalkanyl, substituted cycloalkanyl, arylalkanyl, substituted arylalkanyl, heteroarylalkanyl, and substituted heteroarylalkanyl. In certain embodiments, $R^{27}$ is selected from methyl, ethyl, propyl, isopropyl, butyl, isobutyl, sec-butyl, tert-butyl, cyclopropyl, cyclobutyl, cyclopentyl, cyclohexyl, and benzyl, where the aryl ring of the benzyl group is optionally substituted with one or more substituents selected from halo, CN, $NO_2$, OH, $C_{1-6}$ alkyl, $C_{1-6}$ alkoxy, and —$CO_2R^{31}$.

In certain embodiments, $R^{27}$ is selected from aryl, substituted aryl, heteroaryl, and substituted heteroaryl. In certain embodiments, $R^{27}$ is selected from phenyl, pyridyl, furyl, and thienyl, the aromatic rings of which are optionally substituted with one or more substituents selected from halo, CN, $NO_2$, OH, $C_{1-6}$ alkyl, $C_{1-6}$ alkoxy, and —$CO_2R^{31}$.

In certain embodiments of a compound of Formulae (Ib) or (Ic), $R^4$ and $R^5$ are independently selected from hydrogen and —$(CR^{16}R^{17})OC(O)R^{11}$. In certain embodiments of a compound of Formulae (Ib) or (Ic), $R^4$ and $R^5$ are independently selected from hydrogen and —$(CR^{16}R^{17})OC(O)R^{11}$ wherein $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy. In certain embodiments of a compound of Formulae (Ib) or (Ic), $R^4$ and $R^5$ are independently selected from hydrogen and —$(CR^{16}R^{17})OC(O)R^{11}$ wherein $R^{16}$ and $R^{17}$ are independently selected from hydrogen, $C_{1-6}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formulae (Ib) or (Ic), $R^4$ and $R^5$ are both independently —$(CR^{16}R_{17})OC(O)R^{11}$. In certain embodiments, $R^4$ and $R^5$ are both independently —$(CR^{16}R^{17})OC(O)R^{11}$ wherein $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$, alkoxy, and substituted $C_{1-15}$ alkoxy. In certain embodiments, $R^4$ and $R^5$ are both independently —$(CR^{16}R^{17})OC(O)R^{11}$ wherein $R^{16}$ and $R^{17}$ are independently selected from hydrogen, $C^{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formula (Ic), $R^{10}$ is selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, heteroarylalkanyl, and substituted heteroarylalkanyl, aryl, substituted aryl, heteroaryl, and substituted heteroaryl. In certain embodiments, $R^{10}$ is selected from hydrogen, methyl, ethyl, propyl, isopropyl, butyl, isobutyl, sec-butyl, tert-butyl, cyclopentyl, cyclohexyl, and benzyl, where the aryl ring of the benzyl group is optionally substituted with one or more substituents selected from halo, CN, $NO_2$, OH, $C_{1-6}$ alkyl, $C_{1-6}$ alkoxy, and —$CO_2R^{31}$. In certain embodiments, $R^{10}$ is hydrogen, methyl or ethyl.

In certain embodiments of a compound of Formula (Ic), $R^{10}$ is selected from hydrogen, $C_{1-10}$ alkyl, substituted $C_{1-10}$ alkyl, $C_{5-8}$ aryl, and substituted $C_{5-8}$ aryl.

In certain embodiments of a compound of Formula (Ib), $R^{11}$ is selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, cycloheteroalkanyl, substituted cycloheteroalkanyl, heteroarylalkanyl, and substituted heteroarylalkanyl. In certain embodiments, $R^{11}$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, and styryl, where the aryl ring of the styryl group is optionally substituted with one or more substituents are selected from halo, CN, $NO_2$, OH, $C_{1-6}$ alkyl, $C_{1-6}$ alkoxy, and —$CO_2R^{31}$.

In certain embodiments of a compound of Formula (Ib), $R^{11}$ is selected from aryl, substituted aryl, heteroaryl, and substituted heteroaryl. In certain embodiments, $R^{11}$ is selected from phenyl, pyridyl, indolyl, furyl, imidazolyl, and oxazolyl, the aromatic rings of which are optionally substituted with one or more substituents selected from halo, CN, $NO_2$, OH, $C_{1-6}$ alkyl, $C_{1-6}$ alkoxy, and —$CO_2R^{31}$.

In certain embodiments of a compound of Formula (Ib), $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy.

In certain embodiments of a compound of Formula (Ib), $R^{11}$ is selected from alkoxy, and cycloalkoxy. In certain embodiments, $R^{11}$ is selected from methoxy, ethoxy, propoxy, isopropoxy, butoxy, isobutoxy, sec-butoxy, tert-butoxy, pentyloxy, hexyloxy, cyclopropoxy, cyclobutoxy, cyclopentyloxy, cyclohexyloxy, 2,6-dimethylcyclohexyloxy, fenchyloxy, and adamantyloxy.

In certain embodiments of a compound of Formula (Ib), $R^{11}$ and either $R^{16}$ or $R^{17}$, together with the atoms to which $R^{11}$ and either $R^{16}$ or $R^{17}$ are attached, form a cycloalkyl, substituted cycloalkyl, cycloheteroalkyl or substituted cycloheteroalkyl ring, to which an aryl, substituted aryl, heteroaryl or substituted heteroaryl ring is optionally fused to the cycloheteroalkyl or substituted cycloheteroalkyl ring.

In certain embodiments of a compound of Formulae (Ia), $R^1$ is hydrogen, $R^4$ and $R^5$ are each $C(O)R^{27}$, $R^{10}$ is $C_{1-4}$ alkyl, and $R^{27}$ comprises $C_{1-4}$ alkyl.

In certain embodiments of a compound of Formulae (Ia), $R^1$ is hydrogen, $R^4$ and $R^5$ are each $C(O)R^{27}$, $R^{10}$ is $C_{1-4}$ alkyl, and $R^{27}$ is tert-butyl.

In certain embodiments of a compound of Formulae (Ia), $R^1$ is hydrogen, $R^4$ and $R^5$ are each $C(O)R^{27}$, $R^{10}$ is methyl or ethyl, and $R^{27}$ comprises $C_{1-4}$ alkyl.

In certain embodiments of a compound of Formula (Ib), $R^1$ is hydrogen, $R^4$ and $R^5$ are each $C(O)OR^{27}$, $R^{16}$ is hydrogen, $R^{27}$ is ethyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and $C_{1-4}$ alkyl. In certain embodiments of a compound of Formula (Ib), $R^1$ is hydrogen, $R^4$ and $R^5$ are each $C(O)OR^{27}$, $R^{16}$ is hydrogen, $R^{27}$ is ethyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and methyl.

In certain embodiments of a compound of Formula (Ib), $R^1$ is hydrogen, $R^4$ and $R^5$ are each $C(O)R^{27}$, $R^{16}$ is hydrogen, $R^{27}$ is isopropyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and $C_{1-4}$ alkyl. In certain embodiments of a compound of Formula (Ib), $R^1$ is hydrogen, $R^4$ and $R^5$ are each $C(O)R^{27}$, $R^{16}$ is hydrogen, $R^{27}$ is isopropyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and methyl.

In certain embodiments of a compound of Formula (Ib), $R^1$ is hydrogen, $R^4$ and $R^5$ are each $C(O)R^{27}$, $R^{16}$ is hydrogen, $R^{27}$ is tert-butyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and $C_{1-4}$ alkyl. In certain embodiments of a compound of Formula (Ib), $R^1$ is hydrogen, $R^4$ and $R^5$ are each $C(O)R^{27}$, $R^{16}$ is hydrogen, $R^{27}$ is tert-butyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and methyl.

In certain embodiments of a compound of Formula (Ic), $R^{15}$ is hydrogen.

In certain embodiments of a compound of Formula (Ic), $R^{15}$ is selected from methyl, ethyl, propyl, isopropyl, butyl, isobutyl, and sec-butyl. In certain embodiments, $R^{15}$ is methyl.

In certain embodiments of a compound of Formulae (Ib) or (Ic), $R^{16}$ and $R^{17}$ are independently selected from hydrogen, alkanyl, substituted alkanyl, cycloalkanyl, substituted cycloalkanyl, aryl, substituted aryl, heteroaryl, substituted heteroaryl, arylalkanyl, and substituted arylalkanyl. In certain embodiments, $R^{16}$ and $R^{17}$ are independently selected from hydrogen, methyl, ethyl, propyl, isopropyl, butyl, isobutyl, sec-butyl, tert-butyl, cyclopropyl, cyclobutyl, cyclopentyl, cyclohexyl, phenyl, and benzyl. In certain embodiments, $R^{16}$ is hydrogen and $R^{17}$ is selected from hydrogen, methyl, ethyl, propyl, isopropyl, butyl, isobutyl, sec-butyl, tert-butyl, cyclopropyl, cyclobutyl, cyclopentyl, cyclohexyl, phenyl, and benzyl.

In certain embodiments of a compound of Formulae (Ib) or (Ic), $R^{16}$ and $R^{17}$ together with the carbon atom to which they are attached form a cycloalkanyl, substituted cycloalkanyl, cycloheteroalkanyl or substituted cycloheteroalkanyl ring. In certain embodiments, $R^{16}$ and $R^{17}$ together with the carbon atom to which they are attached form a cyclopropyl, cyclobutyl, cyclopentyl or cyclohexyl ring.

In certain embodiments of a compound of Formulae (Ib) or (Ic), $R^{16}$ and $R^{17}$ are independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formula (Ic), each $R^{20}$ and $R^{21}$ is independently selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, halo, heteroalkanyl, substituted heteroalkanyl, heteroarylalkanyl, and substituted heteroarylalkanyl. In certain embodiments, each $R^{20}$ and $R^{21}$ is independently hydrogen, methyl, ethyl, propyl, isopropyl, butyl, isobutyl, sec-butyl, tert-butyl, cyclopropyl, cyclobutyl, cyclopentyl, cyclohexyl or benzyl.

In certain embodiments of a compound of Formula (Ic), each $R^{20}$ and $R^{21}$ is independently selected from hydrogen, alkanyl, substituted alkanyl, arylalkanyl, substituted arylalkanyl, alkoxy, substituted alkoxy, alkylamino, substituted alkylamino, aryloxy, substituted aryloxy, dialkylamino, substituted dialkylamino, heteroalkyloxy, substituted heteroalkyloxy, heteroaryloxy, and substituted heteroaryloxy. In certain embodiments, each $R^{20}$ and $R^{21}$ is independently selected from hydrogen, alkoxy, alkylamino, aryloxy, dialkylamino or heteroalkyloxy.

In certain embodiments of a compound of Formula (Ic), each $R^{20}$ and $R^{21}$ is independently selected from hydrogen, alkanyl, substituted alkanyl, arylalkanyl, substituted arylalkanyl, acyl, substituted acyl, alkoxycarbonyl, substituted alkoxycarbonyl, carbamoyl, and substituted carbamoyl. In certain embodiments, each $R^{20}$ and $R^{21}$ is hydrogen, acyl, substituted acyl, alkoxycarbonyl, carbamoyl or substituted carbamoyl.

In certain embodiments of a compound of Formula (Ic), each $R^{20}$ and $R^{21}$ is independently selected from hydrogen, alkanyl, substituted alkanyl, arylalkanyl, substituted arylalkanyl, aryl, substituted aryl, heteroaryl, and substituted heteroaryl. In certain embodiments, each $R^{20}$ and $R^{21}$ is independently selected from hydrogen or phenyl, optionally substituted with one or more substituents selected from halo, CN, $NO_2$, OH, $C_{1-6}$ alkyl, $C_{1-6}$ alkoxy, and $—CO_2R^{31}$.

In certain embodiments of a compound of Formula (Ic), wherein r is 1, $R^{20}$ and $R^{21}$ together with the carbon atoms to which $R^{20}$ and $R^{21}$ are attached form a cycloalkanyl, substituted cycloalkanyl, cycloheteroalkanyl or substituted cycloheteroalkanyl ring. In certain embodiments, wherein r is 1, $R^{20}$ and $R^{21}$ together with the carbon atom to which they are attached form a cyclopropyl, cyclobutyl, cyclopentyl or cyclohexyl ring.

In certain embodiments of a compound of Formula (Ic), each $R^{20}$ and $R^{21}$ is independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formulae (Ib) or (Ic), $R^{28}$ and $R^{29}$ are independently selected from hydrogen, alkanyl, aryl, and alkoxycarbonyl. In certain embodiments, $R^{28}$ and $R^{29}$ are independently selected from hydrogen, methyl, ethyl, propyl, butyl, phenyl, methoxycarbonyl, and ethoxycarbonyl. In certain embodiments, $R^{28}$ and $R^{29}$ are both hydrogen.

In certain embodiments of a compound of Formulae (Ib) or (Ic), $R^{31}$ is hydrogen or $C_{1-8}$ alkyl. In certain embodiments, $R^{31}$ is hydrogen, methyl, ethyl, propyl, isopropyl, butyl, isobutyl, sec-butyl, tert-butyl, cyclopropyl, cyclobutyl, cyclopentyl or cyclohexyl.

Synthesis of Certain Compounds

Embodiments of carbidopa prodrugs and/or derivatives thereof can be prepared by methods well known in the art.

In certain embodiments the compounds can be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions can vary with the particular reactants or solvent used, but such conditions can be determined by one skilled in the art by routine optimization procedures.

Additionally, as will be apparent to those skilled in the art, conventional protecting groups can be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*[5] and references cited therein.

Furthermore, in certain embodiments the carbidopa prodrugs and derivatives thereof can contain one or more chiral centers. Accordingly, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) can be prepared using, for example, optically active starting materials or stereoselective reagents well-known in the art. Alternatively, racemic mixtures of such compounds can be separated using, for example, chiral column chromatography, chiral resolving agents and the like.

In certain embodiments, carbidopa prodrugs and derivatives thereof can be prepared by methods well known in the art.[5,11,12,16,23,25] The disclosures of these references are herein incorporated by reference. Some of the preparative methods can be found in U.S. Provisional Application No. 60/238,758[30] and International Publication No. WO 02/28882[32].

A compound of Formula (Ia) where, can be prepared as illustrated in Scheme 1 below. Reacting commercially available carbidopa with an alcohol 11 in the presence of an appropriate coupling agent such as acetyl chloride affords an ester of compound of Formula 12 in which the hydrazine moiety is subsequently protected to provide a compound of Formula 13.

Scheme 1

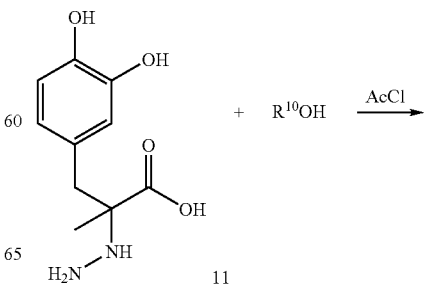

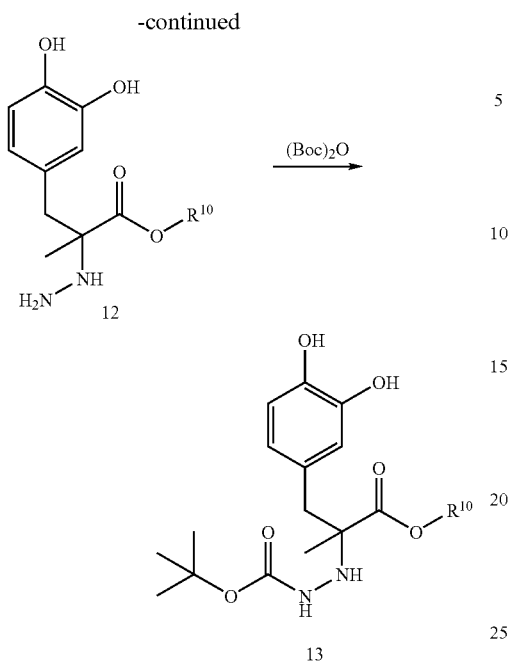
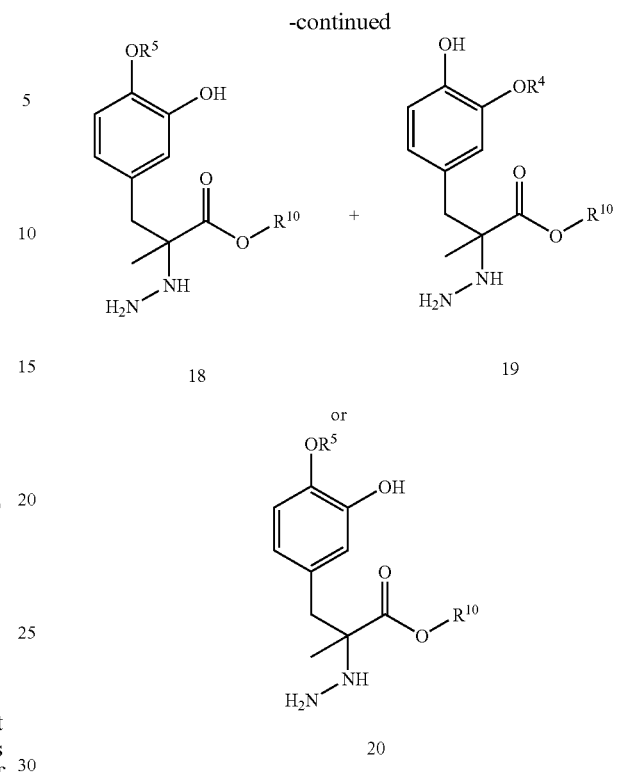

Catechol moieties in 13 can be manipulated with different protecting groups to form mono- or di-substituted analogs as shown in Scheme 2. Thus, treatment of a compound of Formula 13 with an acid halide 14, a haloformate 15, an anhydride 16 or a halide 17 in the presence of a base (e.g., TEA, $Cs_2CO_3$ etc.), in an appropriate solvent (e.g.; dichloromethane, acetone, etc) followed by removal of the hydrazine protecting group affords a mixture of mono-substituted compounds of Formulae 18 and 19 or a di-substituted compound of Formula 20. For compounds wherein $R^4$ and $R^5$ are resistant to hydrolysis under basic conditions (e.g. $R^4$, $R^5$=Me, Bn etc. or $R^4$ and $R^5$ are linked via —CR'R"C—), esters of Formulae 18, 19 and 20 can be converted to the corresponding acids ($R^{10}$=H, e.g. upon treatment with aq. LiOH).

Alternatively, compounds of Formulae 18–20 wherein $R^4$ and $R^5$ are acyl groups can be prepared directly from a compound of Formula 12 by treatment with an acid halide 14 in the presence of an appropriate acid such as trifluoroacetic acid (TFA).

Illustrated in Scheme 3, the hydrazine moiety in carbidopa, 12, 18, 19 and 20 can be elaborated by reacting with a nitrophenyl carbonate of Formula 21 under appropriate conditions to provide acyloxyalkyl carbamates of Formulae 22–26, respectively.

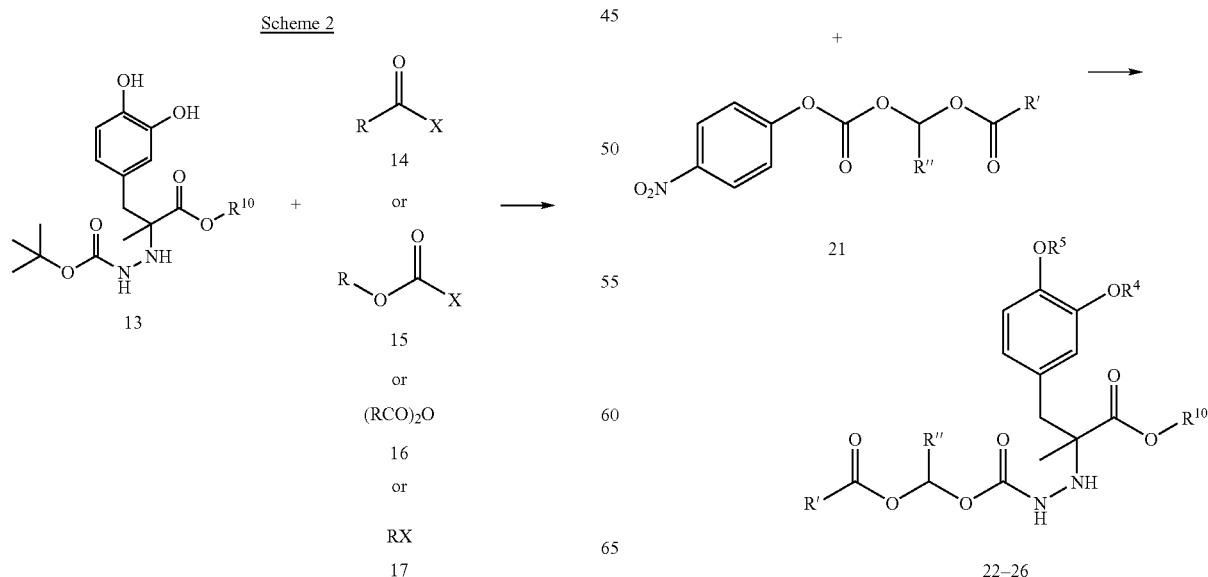

As shown in Scheme 5, compounds of Formulae (Ib) and (Ic) can be prepared by reacting a carboxylic acid 32 (obtained from treatment of carbidopa with (Boc)$_2$O in methanol) with an appropriate halide 33 or a compound of Formula 35, wherein D is OH, NH$_2$, NHR$^{15}$, halide or other leaving group, under appropriate alkylation or coupling conditions to provide compounds of Formulae 36 and 38, respectively. Furthermore, treatment of compounds of Formulae 36 and 38 with electrophiles 14–17 followed by removal of the protecting groups affords compounds of Formulae 39 and 41, in which one or both of R$^4$ and R$^5$ are either acyl, alkoxycarbonyl, alkyl or substituted alkyl (Scheme 5). Directly removing the protecting group (Boc) from compounds of Formulae 36 and 38 also affords compounds of Formulae 39 and 41 in which R$^4$ and R$^5$ are both hydrogen.

Scheme 5

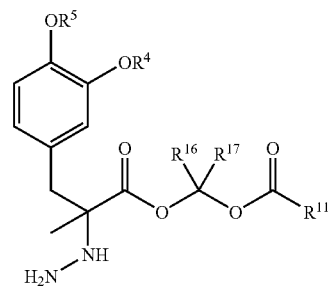

Scheme 4

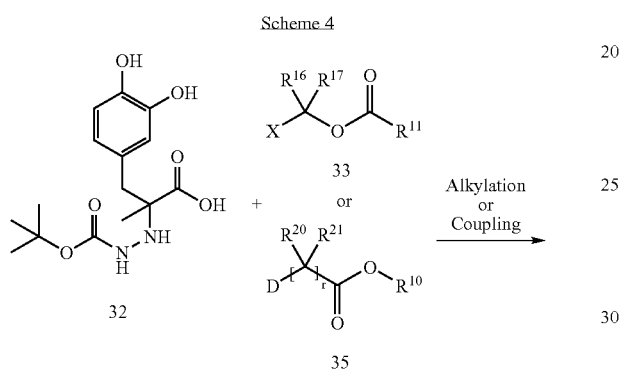

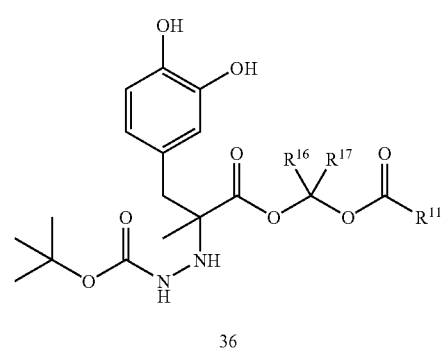

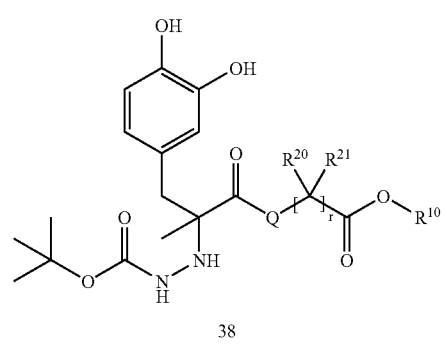

Therapeutic Uses of Certain Compounds

In accordance with certain embodiments, carbidopa prodrugs and derivatives thereof are decarboxylase enzyme inhibitors. Thus, in certain embodiments, a use of the carbidopa prodrugs and derivatives thereof is coadministration with another therapeutic agent or drug which has a tendency to be metabolized by one or more decarboxylase enzymes upon administration. Thus, the carbidopa prodrugs and derivatives thereof of the embodiments can be effective as protectants to inhibit or prevent decarboxylation of another coadministered therapeutic agent or drug. The carbidopa prodrugs and derivatives thereof can be delivered from the same dosage form as the therapeutic agent/drug that is subject to decarboxylation, or from different dosage forms. The carbidopa prodrugs and derivatives thereof can be administered at the same time as, prior to, or subsequent to, the administration of the therapeutic agent/drug subject to decarboxylation. The carbidopa prodrugs and derivatives can have particular utility in inhibiting the decarboxylation of levodopa, and prodrugs and derivatives of levodopa, which are administered to humans suffering from Parkinson's disease. Further, in certain embodiments, the carbidopa prodrugs and derivatives thereof, together with levodopa or a levodopa prodrug or derivative, can be administered to a patient, such as a human, to arrest, ameliorate, reduce the risk of acquiring, reduce the development of or at least one of the clinical symptoms of, or reduce the risk of developing or at least one of the clinical symptoms of, Parkinson's disease.

Certain embodiments of compounds and compositions of carbidopa prodrugs and derivatives thereof together with levodopa or a levodopa prodrug can be advantageously used in human medicine. As mentioned above, in certain embodiments, the compounds and compositions can be useful for the treatment of Parkinson's disease.

When used to treat the above disease, carbidopa prodrugs and derivatives thereof can be administered or applied in combination with levodopa, and/or a levodopa prodrug that is subject to decarboxylation. Additionally, the therapeutic effectiveness of the above combinations can be further enhanced by co-administration of another pharmaceutically active agent (e.g., a catechol oxygen methyl transferase (COMT) inhibitor). Further, in certain embodiments, the carbidopa prodrugs and derivatives thereof, can be administered to a patient, such as a human, together with (i) L-dopa and/or an L-dopa prodrug, and (ii) a pharmaceutically active agent (such as a catechol oxygen methyl transferase (COMT) inhibitor), can be administered to a patient, such as a human, to arrest, ameliorate, reduce the risk of acquiring, reduce the development of or at least one of the clinical symptoms of, or reduce the risk of developing or at least one of the clinical symptoms of, Parkinson's disease.

In certain embodiments, the carbidopa prodrugs and derivatives thereof can be administered orally. Certain carbidopa prodrugs and derivatives thereof can also be administered by any other convenient route, for example, by infusion, absorption through epithelial or mucocutaneous linings (e.g., oral mucosa, rectal and intestinal mucosa).

In certain embodiments, the compounds and/or compositions provide carbidopa and carbidopa prodrugs and derivatives thereof upon in vivo administration to a patient. While not being bound by theory, the promoiety or promoieties of the carbidopa prodrugs and derivatives thereof are currently believed to be cleaved either chemically and/or enzymatically. One or more enzymes present in the stomach, intestinal lumen, intestinal tissue, blood, liver, brain or any other suitable tissue of a mammal can enzymatically cleave the promoiety or promoieties of the compounds and/or compositions. The mechanism of cleavage is not important to the embodiments.

While not being bound by theory, the promoiety or promoieties of certain embodiments of the compounds and/or compositions can be designed to be cleaved after absorption by the gastrointestinal tract (e.g., in intestinal tissue, blood, liver or other suitable tissue of a mammal). In this situation, carbidopa prodrugs and derivatives thereof can have the opportunity to be absorbed into the systemic circulation from the small and large intestines either by passive diffusion, active transport or by both passive and active processes. Certain compounds and/or compositions of carbidopa prodrugs and derivatives thereof can be administered as sustained release systems. In certain embodiments, the compounds can be delivered by oral sustained release administration. In some embodiments, the compounds can be administered twice per day and in certain embodiments, once per day.

Certain carbidopa prodrugs and derivatives thereof can be useful in treating Parkinsonism by administration of one or more of the carbidopa prodrugs and derivatives thereof together with levodopa or a prodrug of levodopa, in certain embodiments by the oral route, to a mammalian subject in need of the treatment. In a human subject weighing 70 kg, a carbidopa prodrug or derivative thereof can be administered at a dose ranging from 10 mg to 10 g per day, and in certain embodiments ranging from 100 mg to 1 g per day. The dose can be adjusted by one skilled in the art based on several factors, e.g. the body weight and/or condition of the subject treated, the dose of the levodopa, levodopa prodrug being administered, the severity of the Parkinson's disease, and the incidence of side effects, the manner of administration and the judgment of the prescribing physician.

Many compounds are also useful in treating hypertension (high blood pressure) by administration of one or more of the carbidopa prodrugs and derivatives thereof either alone or with another hypotensive agent such as clonidine, hydralazine, or guanethidine. Examples of hypotensive agents which can be coadministered with a carbidopa prodrug or derivative thereof are disclosed in U.S. Pat. Nos. 4,055,645 and 4,156,734, the disclosures of which are incorporated herein by reference. In certain embodiments, the hypotensive carbidopa prodrug or derivative thereof can be administered by the oral route to a mammalian subject to be treated for hypertension. The same dosage ranges mentioned above for treating Parkinson's disease can be used for administering the hypotensive carbidopa prodrugs and derivatives thereof in the treatment of hypertension.

For example, the dosage can be delivered in a composition by a single administration, by multiple applications, by sustained release or by controlled sustained release. These latter two are discussed in more detail herein.

Suitable dosage ranges for oral administration can be dependent on the potency of the parent carbidopa or carbidopa derivative drug, but generally range from 0.1 mg to 20 mg of a carbidopa prodrug or derivative thereof per kilogram of body weight. In the case of a carbidopa prodrug or derivative thereof that is metabolized in the patient's body to release carbidopa, the amount of carbidopa released can, in the case of adult patients, be in the range of 25–500 mg/day and the dose of carbidopa prodrug or derivative thereof administered can be adjusted to provide an equivalent molar quantity of carbidopa. Other carbidopa prodrugs and derivatives thereof can be more potent than carbidopa itself and lower doses can be appropriate for both the potent derivatives and prodrugs of such potent derivatives. Dosage ranges can be readily determined by methods known to those skilled in the art.

The carbidopa prodrugs and derivatives thereof can be assayed in vitro and in vivo, for the desired therapeutic or prophylactic activity prior to use in humans. For example, in vitro assays can be used to determine whether administration of a specific carbidopa prodrug or derivative thereof or a combination of such prodrugs and derivatives is appropriate for reducing decarboxylase activity. Carbidopa prodrugs and derivatives thereof can also be demonstrated to be effective and safe using animal model systems.

In certain embodiments, a therapeutically effective dose of a carbidopa prodrug or derivative thereof can provide therapeutic benefit without causing substantial toxicity. Toxicity of carbidopa prodrugs and derivatives thereof can be determined using standard pharmaceutical procedures and can be readily ascertained by the skilled artisan. The dose ratio between toxic and therapeutic effect is the therapeutic index. Certain carbidopa prodrugs and derivatives thereof can exhibit particularly high therapeutic indices in treating diseases and disorders. The dosage of a carbidopa prodrug or derivative thereof can be within a range of circulating concentrations that include an effective dose with little or no toxicity.

Formulations of Certain Compounds

In some embodiments, the carbidopa prodrugs and derivatives thereof can be administered by oral routes. Such compositions can be prepared in a manner well known in the pharmaceutical art and comprise at least one carbidopa prodrug or derivative. The present compositions can contain a therapeutically effective amount of one or more carbidopa prodrugs and derivatives thereof, in some embodiments, in purified form, together with levodopa, and/or a levodopa prodrug, and a suitable amount of a pharmaceutically acceptable vehicle, so as to provide the form for proper administration to a patient.

Certain embodiments also include compositions that contain, as the active ingredient, one or more of the carbidopa prodrugs and derivatives thereof associated with pharmaceutically acceptable excipients, carriers, diluents and/or adjuvants. In making the compositions, the active ingredient can be mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, and syrups containing, for example, up to 90% by weight of the active compound using, for example, soft and hard gelatin capsules.

In preparing a formulation, it can be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. ~40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions can be formulated in unit dosage form, each dosage containing from 1 mg to 2 g of the active ingredient. "Unit dosage forms" refers to physically discrete units suitable as unitary dosages for human subjects and other mammals, each unit containing a predetermined quantity of active material calculated to produce the desired therapeutic effect, in association with a suitable pharmaceutical excipient, diluent, carrier and/or adjuvant.

The active compound can be administered in a therapeutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient, diluent, carrier and/or adjuvant to form a solid preformulation composition containing a homogeneous mixture of a carbidopa prodrug or derivative. When referring to these preformulation compositions as homogeneous, it is meant that the active ingredient is dispersed evenly throughout the composition so that the composition can be readily subdivided into equally effective unit dosage forms such as tablets, pills and capsules. This solid preformulation is then subdivided into unit dosage forms of the type described above containing, for example, from 0.1 mg to 2 g of the therapeutically effective carbidopa prodrug or derivative.

The tablets or pills comprising a carbidopa prodrug or derivative thereof can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings. Such materials include a number of polymeric acids and mixtures of polymeric acids with such materials as shellac, cetyl alcohol, and cellulose acetate.

The liquid forms in which the compositions comprising carbidopa prodrugs and derivatives thereof can be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Sustained Release Oral Dosage Forms

Certain carbidopa prodrugs and derivatives thereof can be practiced with a number of different dosage forms, which can be adapted to provide sustained release of the prodrug or derivative upon oral administration.

In certain embodiment, the dosage form can comprise beads that on dissolution or diffusion release the prodrug or derivative over an extended period of hours, in some embodiments, over a period of at least 6 hours, in some embodiments, over a period of at least 8 hours and in other embodiments, over a period of at least 12 hours. The prodrug- or derivative-releasing beads can have a central composition or core comprising a prodrug or derivative and pharmaceutically acceptable vehicles, including an optional lubricant, antioxidant and buffer. The beads can be medical preparations with a diameter ranging from 1 mm to 2 mm. Individual beads can comprise doses of the prodrug or derivative, for example, doses of up to 40 mg of prodrug or derivative. The beads, in certain embodiments, can be formed of non-cross-linked materials to enhance their discharge from the gastrointestinal tract. The beads can be coated with a release rate-controlling polymer that gives a timed-release profile.

The timed-release beads can be manufactured into a tablet for therapeutically effective prodrug or derivative administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, *Int. J. Pharm.*, 1994, 112, 117–124; Pharmaceutical Sciences by Remington, 14$^{th}$ ed, pp 1626–1628 (1970); Fincher, *J. Pharm. Sci.* 1968, 57, 1825–1835; and U.S. Pat. No. 4,083,949) as has the manufacture of tablets (Pharmaceutical Sciences, by Remington, 17$^{th}$ Ed, Ch. 90, pp. 1603–1625 (1985).

In certain embodiments, an oral sustained release pump can be used (see Langer, supra; Sefton, 1987, *CRC Crit. Ref. Biomed. Eng.* 14:201; Saudek et al., 1989, *N. Engl. J. Med.* 321:574).

In certain embodiments, polymeric materials can be used (see "Medical Applications of Controlled Release," Langer and Wise (eds.), CRC Press, Boca Raton, Fla. (1974);

"Controlled Drug Bioavailability," Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228: 190; During et al., 1989, *Ann. Neurol.* 25:351; Howard et al, 1989, *J. Neurosurg.* 71:105). In certain embodiments, polymeric materials can be used for oral sustained release delivery. In certain embodiments, polymers include sodium carboxymethylcellulose, hydroxypropylcellulose, hydroxypropylmethylcellulose and hydroxyethylcellulose, and in some embodiments, hydroxypropylmethylcellulose. Other cellulose ethers have been described (Alderman, *Int. J. Pharm. Tech. & Prod. Mfr.*, 1984, 5(3) 1–9). Factors affecting drug release are well known to the skilled artisan and have been described in the art (Bamba et al., *Int. J. Pharm.*, 1979, 2, 307).

In certain embodiments, enteric-coated preparations can be used for oral sustained release administration. In certain embodiments, coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

In certain embodiments, drug-releasing lipid matrices can be used for oral sustained release administration. One example is when solid microparticles of the prodrug or derivative are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In certain embodiments, prodrug- or derivative-releasing waxes can be used for oral sustained release administration. Examples of suitable sustained prodrug- or derivative-releasing waxes are disclosed in Cain et al., U.S. Pat. No. 3,402,240 (carnauba wax, candedilla wax, esparto wax and ouricury wax); Shtohryn et al. U.S. Pat. No. 4,820,523 (hydrogenated vegetable oil, bees wax, carnauba wax, paraffin, candedilla, ozokerite and mixtures thereof); and Walters, U.S. Pat. No. 4,421,736 (mixture of paraffin and castor wax).

In certain embodiments, a controlled-release system can be placed in proximity to the target of the carbidopa prodrug or derivative, thus requiring only a fraction of the systemic dose (see, e.g., Goodson, in "Medical Applications of Controlled Release," supra, vol. 2, pp. 115–138 (1984)). Other controlled-release systems discussed in Langer, 1990, *Science* 249:1527–1533 can also be used.

In certain embodiments, the dosage form can comprise a carbidopa prodrug or derivative thereof coated on a polymer substrate. The polymer can be an erodible, or a nonerodible polymer. The coated substrate can be folded onto itself to provide a bilayer polymer drug dosage form. For example, a carbidopa prodrug or derivative thereof can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the prodrug or derivative over a sustained release period. Representative biodegradable polymers comprise a polymer selected from biodegradable poly(amides), poly(amino acids), poly(esters), poly(lactic acid), poly(glycolic acid), poly(carbohydrate), poly(orthoester), poly(orthocarbonate), poly(acetyl), poly(anhydrides), biodegradable poly(dehydropyrans), and poly(dioxinones) which are known in the art (Rosoff, *Controlled Release of Drugs*, Chap. 2, pp. 53–95 (1989); and in U.S. Pat. Nos. 3,811,444; 3,962,414; 4,066,747, 4,070,347; 4,079,038; and 4,093,709).

In certain embodiments, the dosage form can comprise a carbidopa prodrug or derivative thereof loaded into a polymer that releases the prodrug or derivative by diffusion through a polymer, or by flux through pores or by rupture of a polymer matrix. The drug delivery polymeric dosage form can comprise a concentration ranging from 10 mg to 2500 mg homogeneously contained in or on a polymer. The dosage form can comprise at least one exposed surface at the beginning of dose delivery. The non-exposed surface, when present, can be coated with a pharmaceutically acceptable material impermeable to the passage of the prodrug or derivative. The dosage form can be manufactured by procedures known in the art. An example of providing a dosage form comprises blending a pharmaceutically acceptable carrier like polyethylene glycol, with a known dose of prodrug or derivative at an elevated temperature, like 37° C., and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing the dosage form comprise a member selected from olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, polyalginate, polyamide and polysilicon. The polymers and procedures for manufacturing them have been described in the art (Coleman et al., *Polymers* 1990, 31, 1187–1231; Roerdink et al., *Drug Carrier Systems* 1989, 9, 57–10.; Leong et al., *Adv. Drug Delivery Rev.* 1987, 1, 199–233; Roff et al., *Handbook of Common Polymers* 1971, CRC Press; U.S. Pat. No. 3,992,518).

In certain embodiments, the dosage form can comprise a plurality of tiny pills. The tiny time-released pills provide a number of individual doses for providing various time doses for achieving a sustained-release prodrug or derivative delivery profile over an extended period of time up to 24 hours. The matrix can comprise a hydrophilic polymer selected from a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix can comprise a plurality of 4 to 50 tiny pills, each tiny pill comprising a dose population selected from, for example, 10 ng, 0.5 mg, 1 mg, 1.2 mg, 1.4 mg, 1.6 mg, 5.0 mg, etc. The tiny pills comprise a release rate-controlling wall of 0.001 up to 10 mm thickness to provide for the timed release of prodrug or derivative. Representative wall forming materials include a triglyceryl ester selected from glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in U.S. Pat. Nos. 4,434,153; 4,721,613; 4,853,229; 2,996,431; 3,139,383 and 4,752,470.

In certain embodiments, osmotic delivery systems can be used for oral sustained release administration (Verma et al., *Drug Dev. Ind. Pharm.,* 2000, 26:695–708). In certain embodiments, OROS® systems made by Alza Corporation, Mountain View, Calif. can be used for oral sustained release drug delivery (Theeuwes et al., U.S. Pat. No. 3,845,770; Theeuwes et al., U.S. Pat. No. 3,916,899). In certain embodiments, the dosage form can comprise an osmotic dosage form, which comprises a semipermeable wall that surrounds a therapeutic composition comprising the carbidopa prodrug or derivative. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug or derivative release. These delivery platforms can provide an essentially zero order delivery profile as opposed to the spiked profiles of immediate release formulations.

In certain embodiments, the dosage form can comprise another osmotic dosage form comprising a wall surrounding a compartment, the wall comprising a semipermeable polymeric composition permeable to the passage of fluid and substantially impermeable to the passage of the carbidopa prodrug or derivative thereof present in the compartment, a prodrug- or derivative-containing layer composition in the compartment, a hydrogel push layer composition in the compartment comprising an osmotic formulation for imbibing and absorbing fluid for expanding in size for pushing the prodrug or derivative composition layer from the dosage form, and at least one passageway in the wall for releasing the prodrug or derivative composition. The method delivers the prodrug or derivative by imbibing fluid through the semipermeable wall at a fluid imbibing rate determined by the permeability of the semipermeable wall and the osmotic pressure across the semipermeable wall causing the push layer to expand, thereby delivering the prodrug or derivative from the dosage form through the exit passageway to a patient over a prolonged period of time (up to 24 or even 30 hours). The hydrogel layer composition can comprise 10 mg to 1000 mg of a hydrogel such as a member selected from a polyalkylene oxide of 1,000,000 to 8,000,000 weight-average molecular weight, which are selected from a polyethylene oxide of 1,000,000 weight-average molecular weight, a polyethylene oxide of 2,000,000 weight-average molecular weight, a polyethylene oxide of 4,000,000 weight-average molecular weight, a polyethylene oxide of 5,000,000 weight-average molecular weight, a polyethylene oxide of 7,000,000 weight-average molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer can comprise 0.0 mg to 350 mg, such as 0.1 mg to 250 mg, of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose); 1 mg to 50 mg of an osmagent selected from sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, such as 0.1 mg to 30 mg, of a hydroxypropylalkylcellulose of 9,000 to 225,000 average-number molecular weight, selected from hydroxypropylethylcellulose, hydroxypropypentylcellulose, hydroxypropylmethylcellulose, and hydropropylbutylcellulose; 0.0 to 1.5 mg of an antioxidant selected from ascorbic acid, butylated hydroxyanisole, butylatedhydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine; and 0.0 mg to 7 mg of a lubricant selected from calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall can comprise a composition that is permeable to the passage of fluid and impermeable to the passage of the carbidopa prodrug or derivative. The wall can be nontoxic and can comprise a polymer selected from a cellulose acylate, cellulose diacylate, cellulose triacylate, cellulose acetate, cellulose diacetate and cellulose triacetate. The wall can comprise 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from hydroxypropylcellulose or a hydroxypropylalkycellulose such as hydroxypropylmethylcellulose. The total weight percent of all components comprising the wall is equal to 100 wt %. The internal compartment can comprise the prodrug- or derivative-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the prodrug or derivative composition is pushed from the dosage form. The therapeutic layer and the expandable layer act together during the operation of the dosage form for the release of prodrug or derivative to a patient over time. The dosage form can comprise a passageway in the wall that connects the exterior of the dosage form with the internal compartment. The osmotic powered dosage form provided by certain embodiments delivers the carbidopa prodrug or derivative thereof from the dosage form to the patient at a zero order rate of release over a period of up to about hours.

The expression "passageway" as used herein comprises means and methods suitable for the metered release of the carbidopa prodrug or derivative thereof from the compartment of the dosage form. The exit means comprises at least one passageway, including orifice, bore, aperture, pore, porous element, hollow fiber, capillary tube, channel, porous overlay, or porous element that provides for the osmotic controlled release of prodrug or derivative. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug or derivative from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Regardless of the specific form of sustained release oral dosage form used, the carbidopa prodrug or derivative thereof can be released from the dosage form over a period of at least 6 hours, in some embodiments, over a period of at least 8 hours, and in some embodiments, over a period of at least 12 hours. Further, the dosage form can release from 0 to 20% of the carbidopa prodrug or derivative thereof in 0 to 2 hours, from 20 to 50% of the prodrug or derivative thereof in 2 to 12 hours, from 50 to 85% of the prodrug or derivative thereof in 3 to 20 hours and greater than 75% of the prodrug or derivative thereof in 5 to 18 hours.

In certain embodiments, the dosage forms can be administered twice per day, and in some embodiments, once per day.

EXAMPLES

Certain embodiments can be further defined by reference to the following examples, which describe in detail preparation of compounds and compositions comprising carbidopa prodrugs and derivatives thereof and assays for using compounds and compositions comprising carbidopa prodrugs and derivatives thereof. It will be apparent to those skilled in the art that many modifications, both to materials and methods, can be practiced without departing from the embodiments.

The following synthetic and biological examples are offered to illustrate certain embodiments and are not to be construed in any way as limiting the scope. Unless otherwise stated, all temperatures are in degrees Celsius. In the examples below, the following abbreviations have the following meanings. If an abbreviation is not defined, it has its generally accepted meaning.

Atm=atmosphere
Boc=tert-butyloxycarbonyl
Cbz=carbobenzyloxy
CPM=counts per minute
DCC=dicyclohexylcarbodiimide
DMAP=4-N,N-dimethylaminopyridine
DMEM=Dulbecco's minimum eagle medium
DMF=N,N-dimethylformamide
DMSO=dimethylsulfoxide
Fmoc=9-fluorenylmethyloxycarbonyl
g=gram
hr=hour
HBSS=Hank's buffered saline solution
L=liter
LC/MS=liquid chromatography/mass spectroscopy
M=molar
min=minute
mL=milliliter
mmol=millimoles
NHS=N-hydroxysuccinimide
PBS=phosphate buffered saline
THF=tetrahydrofuran
TFA=trifluoroacetic acid
TMS=trimethylsilyl
µL=microliter
µM=micromolar
v/v=volume to volume

Example 1

3-(3,4-Bis-ethoxycarbonyloxy-phenyl)-2-hydrazino-2-methyl-propionic acid acetoxymethyl ester (101)

Step A: 2-(N'-tert-Butoxycarbonyl-hydrazino)-3-(3,4-dihydroxy-phenyl)-2-methyl-propionic acid (102)

To a mixture of carbidopa (5 g, 20 mmol), triethylamine (3 mL, 21 mmol) in methanol, was added Boc anhydride (4.7 g, 21 mmol) at 0° C. The reaction mixture was stirred at room temperature for 16 h under nitrogen. After removing the solvent under reduced pressure, the product was partitioned between ethyl acetate and 10% citric acid. The organic layer was separated, dried over $MgSO_4$ and concentrated to give 6.2 g (95%) of the title compound. $^1H$ NMR ($CD_3OD$, 400 MHz): 1.28 (s, 3H), 1.46 (s, 9H), 2.83 (dd, 2H), 6.60 (m, 3H). MS (ESI) m/z 349.21 (M+Na$^+$).

Step B: 2-(N'-tert-Butoxycarbonyl-hydrazino)-3-(3,4-Dihydroxy-phenyl)-2-methyl-propionic acid acetoxymethyl ester (103)

To a suspension of compound 102 (170 mg, 0.5 mmol) and cesium bicarbonate (99 mg, 0.5 mmol) in acetone was added bromomethyl acetate (170 mg, 0.5 mmol) and the mixture stirred at 44° C. temperature for 16 h. After removing the solvent under reduced pressure, the residue was partitioned between ethyl acetate and 10% citric acid. The organic layer was separated, dried over $MgSO_4$ and concentrated to afford the crude product, which was used in the next reaction without further purification.

Step C: 3-(3,4-Bis-ethoxycarbonyloxy-phenyl)-2-hydrazino-2-methyl-propionic acid acetoxymethyl ester (101)

To an ice cold reaction mixture containing compound 103 (0.358 g, 0.9 mmol) and TEA (0.224 mL, 1.8 mmol) in dichloromethane (5 mL) was added ethyl chloroformate (0.18 mL, 1.8 mmol). The mixture was stirred at 0° C. for 30 min and then at room temperature for 1 h. After removal of solvent, 10% citric acid was added and the organic phase was separated and dried over $MgSO_4$. After removing the solvent under reduced pressure, the resulting residue was treated with 50% trifluoroacetic acid in dichloromethane at room temperature for 30 min. After removing the solvent under reduced pressure, the resulting residue was purified by reverse phase preparative HPLC to afford 208 mg of the title compound. $^1H$ NMR ($CD_3OD$, 400 MHz): 1.35 (t, 6H), 1.45 (s, 3H), 3.08 (dd, 2H), 3.80 (s, 3H), 4.28 (q, 4H), 5.83 (dd, 2H), 7.12–7.24 (m, 3H). MS (ESI) m/z 443.28 (M+H$^+$).

Example 2

3-(3,4-Dihydroxyphenyl)-2-hydrazino-2-methyl-propionic acid acetoxymethyl ester (104)

Crude 103 was treated in a flask with 50% trifluoroacetic acid in dichloromethane at room temperature for 30 min. After removing the solvent under reduced pressure, the resulting residue was purified by reverse phase preparative HPLC to afford 57 mg of the title compound. $^1$H NMR (CD$_3$OD, 400 MHz): 1.37 (s, 3H), 1.98 (s, 3H), 2.82 (dd, 2H), 5.02 (s, 2H), 6.50 (m, 3H). MS (ESI) m/z 299.24 (M+H$^+$).

Example 3

3-(3,4-Bis-ethoxycarbonyloxy-phenyl)-2-hydrazino-2-methyl-propionic acid 2,2-dimethyl-propionyloxymethyl ester (105)

Following the procedure for preparation of compound 101, and substituting bromomethyl acetate with iodomethyl pivalate, provided the title compound. $^1$H NMR (CD$_3$OD, 400 MHz): 1.24 (s, 9H), 1.34 (t, 6H), 1.44 (s, 3H), 3.08 (dd, 2H), 4.29 (q, 4H), 5.88 (dd, 2H), 7.19–7.25 (m, 3H). MS (ESI) m/z 485.32 (M+H$^+$)

Example 4

3-(3,4-Bis-ethoxycarbonyloxy-phenyl)-2-hydrazino-2-methyl-propionic acid methyl ester (106)

Step A: Methyl 3-(3,4-dihydroxyphenyl)-2-hydrazino-2-methyl-propionate (107)

To a solution of carbidopa (226 mg, 1 mmol) in anhydrous methanol (20 mL), was added acetyl chloride (1 mL) at 0° C. The mixture was stirred at 65° C. in a pressure vessel for 4 h. Removal of solvent yielded 270 mg (99%) of the title compound as its hydrochloride salt. $^1$H NMR (CD$_3$OD, 400 MHz): 1.46 (s, 3H), 2.86 (dd, 2H), 3.78 (s, 3H), 6.45 (dd, J=8 Hz, J=2 Hz), 6.56 (d, J=2.4 Hz), 6.69 (d, J=8.4 Hz). MS (ESI) m/z 241.15 (M+H$^+$).

Step B: 2-(N'-tert-Butoxycarbonyl-hydrazino)-3-(3,4-dihydroxy-phenyl)-2-methyl-propionic acid methyl ester (108)

Following the procedure in Example 1 Step A, and substituting carbidopa with carbidopa methyl ester 107, provided the title compound. $^1$NMR (CD$_3$OD, 400 MHz): 1.22 (s, 3H), 1.42 (s, 9H), 2.80 (dd, 2H), 3.70 (s, 3H), 6.60 (m, 3H). MS (ESI) m/z 341.44 (M+H$^+$).

Step C: 3-(3,4-Bis-ethoxycarbonyloxy-phenyl)-2-hydrazino-2-methyl-propionic acid methyl ester (106)

Following the procedure in Example 1 Step C, and substituting 103 with 108, provided the title compound. $^1$H NMR (CD$_3$OD, 400 MHz): 1.36 (t, 6H), 1.45 (s, 3H), 3.10 (dd, 2H), 3.80 (s, 3H), 4.30 (q, 4H), 7.15–7.28 (m, 3H). MS (ESI) m/z 385.42 (M+H$^+$).

Example 5

3-[3,4-Bis-(2,2-dimethyl-propionyloxy)-phenyl]-2-hydrazino-2-methyl-propionic acid methyl ester (109)

Following the procedure in Example 4 Step C, and substituting ethyl chloroformate with pivalic anhydride, provided the title compound. $^1$H NMR (CD$_3$OD, 400 MHz): 1.37 (s, 18H), 1.46 (s, 3H), 3.11 (dd, 2H), 3.80 (s, 3H), 7.06–7.19 (m, 3H). MS (ESI) m/z 409.39 (M+H$^+$).

Example 6

3-(3,4-Bis-ethoxycarbonyloxy-phenyl)-2-hydrazino-2-methyl-propionic acid (110)

Following the procedure for preparation of 106, and substituting ethyl chloroformate and 108 with diethyl pyrocarbonate and 102, respectively, provided the title compound. $^1$H NMR (CD$_3$OD, 400 MHz): 1.18 (t, 6H), 1.36 (s, 3H), 3.01 (dd, 2H), 3.80 (s, 3H), 4.17 (q, 4H), 7.08–7.17 (m, 3H). MS (ESI) m/z 371.24 (M+H$^+$).

Example 7

3-[3,4-Bis-(2,2-dimethyl-propionyloxy)-phenyl]-2-hydrazino-2-methyl-propionic acid (111)

Following the procedure for preparation of 106, and substituting ethyl chloroformate and 108 with pivalic anhydride and 102, respectively, provided the title compound. $^1$H NMR (CD$_3$OD, 400 MHz): 1.34 (s, 18H), 1.46 (s, 3H), 3.11 (dd, 2H), 7.06–7.19 (m, 3H). MS (ESI) m/z 395.36 (M+H$^+$).

Example 8

3-(3,4-Dihydroxy-phenyl)-2-hydrazino-2-methyl-propionic acid 2,2-dimethyl-propionyloxymethyl ester (112)

Following the procedures described in Examples 1 and 2, and substituting bromomethyl acetate with iodomethyl pivalate, provided the title compound. $^1$H NMR (CD$_3$OD, 400 MHz): 1.24 (s, 9H), 1.44 (s, 3H), 2.90 (dd, 2H), 5.86 (s, 2H), 6.58 (m, 3H). MS (ESI) m/z 341.28 (M+H$^+$).

Example 9

2-Hydrazino-3-[3-hydroxy-4-(3-oxo-1,3-dihydro-isobenzofuran-1-yloxy)-phenyl]-2-methyl-propionic acid methyl ester (113) and 2-Hydrazino-3-[4-hydroxy-3-(3-oxo-1,3-dihydro-isobenzofuran-1-yloxy)-phenyl]-2-methyl-propionic acid methyl ester (114)

A mixture of compound 108 (380 mg, 1.1 mmol), bromophthalide (213 mg, 1 mmol) and CsHCO$_3$ (325 mg, 1 mmol) in acetone was stirred at room temperature for 16 h. After removing the solvent under reduced pressure, the residue was partitioned between 10% citric acid and ethyl acetate. The organic phase was separated and dried over MgSO$_4$. After removing the solvent under reduced pressure, the resulting residue was treated with 50% trifluoroacetic acid in dichloromethane at room temperature for 30 min. After removing the solvent, the resulting residue was purified by reverse phase preparative HPLC to afford two separated stereoisomers 113 (123 mg) and 114 (120 mg), respectively. Compound 113: $^1$H NMR (CD$_3$OD, 400 MHz): 1.43 (s, 3H), 2.98 (dd, 2H), 3.80 (s, 3H), 6.62–7.20 (m, 4H), 7.66–7.95 (m, 4H). MS (ESI) m/z 373.25 (M+H$^+$) and Compound 114: $^1$H NMR (CD$_3$OD, 400 MHz): 1.44 (s, 3H), 2.99 (dd, 2H), 3.84 (s, 3H), 6.80–7.18 (m, 4H), 7.69–7.93 (m, 4H). MS (ESI) m/z 373.25 (M+H$^+$).

Example 10

3-[4-(2,2-Dimethyl-propionyloxymethoxy)-3-hydroxy-phenyl]-2-hydrazino-2-methyl-propionic acid methyl ester (115) and 3-[3-(2,2-Dimethyl-propionyloxymethoxy)-3-hydroxy-phenyl]-2-hydrazino-2-methyl-propionic acid methyl ester (116)

Following the procedure for preparation of compounds 113 and 114, and substituting bromophthalide with iodomethyl pivalate, provided the title compounds 115 and 116, respectively. Compound 115: $^1$H NMR (CD$_3$OD, 400 MHz): 1.18 (s, 9H), 1.45 (s, 3H), 2.98 (dd, 2H), 3.78 (s, 3H), 5.74 (s, 2H), 6.58–6.98 (m, 3H). MS (ESI) m/z 355.30 (M+H$^+$) and Compound 116: $^1$H NMR (CD$_3$OD, 400 MHz): 1.20 (s, 9H), 1.46 (s, 3H), 2.98 (dd, 2H), 3.78 (s, 3H), 5.75 (dd, 2H), 6.68–6.89 (m, 3H). MS (ESI) m/z 355.38 (M+H$^+$).

Example 11

3-(4-Benzyloxy-3-hydroxy-phenyl)-2-hydrazino-2-methyl-propionic acid methyl ester (117) and 3-(3-Benzyloxy-3-hydroxy-phenyl)-2-hydrazino-2-methyl-propionic acid methyl ester (118)

Following the procedure for preparation of compounds 113 and 114, and substituting bromophthalide with benzyl bromide, provided the title compounds 117 and 118, respectively. Compound 117: $^1$H NMR (CD$_3$OD, 400 MHz): 1.38 (s, 3H), 2.90 (dd, 2H), 3.65 (s, 3H), 5.15 (s, 2H), 6.59–6.78 (m, 3H), 7.27–7.44 (m, 4H). MS (ESI) m/z 331.30 (M+H$^+$) and compound 118: $^1$H NMR (CD$_3$OD, 400 MHz): 1.42 (s, 3H), 2.92 (dd, 2H), 3.65 (s, 3H), 5.15 (s, 2H), 6.45–6.92 (m, 3H), 7.24–7.44 (m, 4H). MS (ESI) m/z 331.29 (M+H$^+$).

Example 12

3-[3,4-Bis-(3-oxo-1,3-dihydro-isobenzofuran-1-yloxy)-phenyl]-2-hydrazino-2-methyl-propionic acid methyl ester (119)

A mixture of compound 108 (170 mg, 0.5 mmol), bromophthalide (213 mg, 1 mmol) and Cs$_2$CO$_3$ (325 mg, 1 mmol) in acetone was stirred at 40° C. for 16 h. After removing the solvent under reduced pressure, the residue was partitioned between 10% citric acid and ethyl acetate. The organic phase was separated and dried over MgSO$_4$, and concentrated to dryness. The resulting residue was treated with 50% trifluoroacetic acid in dichloromethane at room temperature for 30 min. Removal of the solvent and purification of the resulting residue by reverse phase HPLC afford 81 mg of 119 as a mixture of diastereomers. $^1$H NMR (CD$_3$OD, 400 MHz): 1.50 (3H), 3.10 (2H), 3.84 (3H), 6.86–7.18 (m, 3H), 7.22–7.44 (m, 2H), 7.61–7.95 (m, 8H). MS (ESI) m/z 505.26.

Example 13

3-(3,4-Dimethoxy-phenyl)-2-hydrazino-2-methyl-propionic acid methyl ester (120)

Following the procedure for preparation of compound 119, and substituting bromophthalide with iodomethane, provided the title compound 120. $^1$H NMR (CD$_3$OD, 400 MHz): 1.44 (s, 3H), 3.00 (dd, 2H), 3.80 (2 s, 6H), 4.77 (s, 3H), 6.71–6.86 (m, 3H). MS (ESI) m/z 269.33 (M+H$^+$).

Example 14

3-(3,4-Dimethoxy-phenyl)-2-hydrazino-2-methyl-propionic acid (121)

Following the procedure for preparation of compound 119, and treatment of the resulting 120 with 0.33M of LiOH in H$_2$O/MeOH/THF before Boc removal by TFA, provided the title compound 121. $^1$H NMR (CD$_3$OD, 400 MHz): 1.49 (s, 3H), 3.05 (dd, 2H), 3.80 (2 s, 6H), 6.77–6.92 (m, 3H). MS (ESI) m/z 255.25 (M+H$^+$).

Example 15

3-(3,4-Dihydroxy-phenyl)-2-hydrazino-2-methyl-propionic acid 3-oxo-1,3-dihydro-isobenzofuran-1-yl ester (122)

Following the procedure for preparation of compound 104, and substituting bromomethyl acetate with bromophthalide, provided the title compound 122 as a mixture of diastereomers. MS (ESI) m/z 359.03 (M+H$^+$).

Example 16

3-(3-Ethoxycarbonyloxy-4-hydroxy-phenyl)-2-hydrazino-2-methyl-propionic acid methyl ester (123) and 3-(4-Ethoxycarbonyloxy-3-hydroxy-phenyl)-2-hydrazino-2-methyl-propionic acid methyl ester (124)

To an ice cold reaction mixture containing compound 108 (0.17 g, 0.5 mmol) and TEA (0.07 mL, 0.5 mmol) in dichloromethane (5 mL) was added ethyl chloroformate (0.025 mL, 0.5 mmol). The resulting mixture was stirred at 0° C. for 30 min and then at room temperature for 1. After concentration, the residue was partitioned with 10% citric acid and ethyl acetate. The organic phase was separated and dried over MgSO$_4$. After removing the solvent under reduced pressure, the resulting residue was treated with 50% trifluoroacetic acid in dichloromethane at room temperature for 30 min. Removal of the solvent and purification by reverse phase preparative HPLC afford 73 mg of a 1:1 mixture of the title compounds 123 and 124. $^1$H NMR (CD$_3$OD, 400 MHz): 1.35 (q, 3H), 1.46 (d, 3H), 2.98 (dd, 2H), 3.80 (d, 3H), 4.28 (q, 4H), 6.60–6.98 (m, 3H). MS (ESI) m/z 313.25 (M+H$^+$).

Example 17

2,6-Dimethyl-benzoic acid 4-(2-carboxy-2-hydrazino-propyl)-2-hydroxy-phenyl ester (125) and 2,6-Dimethyl-benzoic acid 5-(2-carboxy-2-hydrazino-propyl)-2-hydroxy-phenyl ester (126)

To a solution of carbidopa (732 mg, 3 mmol) in trifluoroacetic acid (10 mL), was slowly added 2,6-dimethylbenzoyl chloride (504 mg, 3 mmol) at 0° C. and the mixture stirred at room temperature for 1 h. The reaction mixture was concentrated under reduced pressure. The oily residue was dissolved in acetonitrile/H$_2$O and purified by reverse phase preparative HPLC to afford 196 mg of compound 125 [$^1$H NMR (CD$_3$OD, 400 MHz) 1.49 (s, 3H), 2.45 (d, 6H), 3.10 (dd, 2H), 6.82–7.25 (m, 6H). MS (ESI) m/z 359.23 (M+H$^+$)] and 161 mg of compound 126 [$^1$H NMR (CD$_3$OD, 400 MHz): 1.45 (s, 3H), 2.42 (d, 6H), 3.15 (dd, 2H), 6.74–7.27 (m, 6H). MS (ESI m/z 359.23 (M+H$^+$)].

Example 18

2,6-Dimethyl-benzoic acid 4-(2-hydrazino-2-methoxycarbonyl-propyl)-2-hydroxy-phenyl ester (127) and

2,6-Dimethyl-benzoic acid 5-(2-hydrazino-2-methoxycarbonyl-propyl)-2-hydroxy-phenyl ester (128)

Following the procedure for preparation of compounds 125 and 126, and substituting carbidopa with carbidopa methyl ester, provided the title compounds 127 [$^1$H NMR (CD$_3$OD, 400 MHz): 1.42 (s, 3H), 2.43 (d, 6H), 3.10 (dd, 2H), 3.78 (s, 3H), 6.82–7.30 (m, 6H). MS (ESI) m/z 373.08 (M+H$^+$)] and 128 [$^1$H NMR (CD$_3$OD, 400 MHz): 1.43 (s, 3H), 2.42 (d, 6H), 3.02 (dd, 2H), 3.80 (s, 3H), 6.65–7.22 (m, 6H). MS (ESI) m/z 373.08 (M+H$^+$)].

Example 19

2-Methyl-benzoic acid 4-(2-hydrazino-2-carbonyl-propyl)-2-hydroxy-phenyl ester (129) and

2-Methyl-benzoic acid 5-(2-hydrazino-2-carbonyl-propyl)-2-hydroxy-phenyl ester (130)

Following the procedure for preparation of compounds 125 and 126, and substituting 2,6-dimethyl-benzoyl chloride with 2-methyl-benzoyl chloride, provided the title compounds 129 and 130 as a mixture of two inseparable regioisomers. $^1$H NMR (CD$_3$OD, 400 MHz): 1.10 (d, 3H), 2.21 (d, 3H), 2.64 (dd, 2H), 6.36–7.75 (m, 7H). MS (ESI) m/z 343.23 (M–H$^+$).

Example 20

2-Methyl-benzoic acid 4-{2-carboxy-2-[N'-(2,2-dimethyl-propionyloxy-methoxycarbonyl)-hydrazino]-propyl}-2-hydroxy-phenyl ester (131) and

2-Methyl-benzoic acid 5-{2-carboxy-2-[N'-(2,2-dimethyl-propionyloxy-methoxycarbonyl)-hydrazino]-propyl}-2-hydroxy-phenyl ester (132)

To a mixture of compounds 129 and 130 (194 mg, 0.34 mmol) in dimethylformamide (5 mL) was added α-pivaloxymethyl-p-nitrophenyl carbonate (0.1 g, 0.34 mmol) and triethylamine (0.142 mL, 1.02 mmol) at room temperature. After stirring for 30 min, the mixture was partitioned between ethyl acetate and 10% citric acid. The organic layer was separated, dried (MgSO$_4$) and concentrated to dryness. The resulting residue was purified by reverse phase preparative HPLC to afford 113 mg of the title compounds as a mixture of regioisomers. $^1$H NMR (CD$_3$OD, 400 MHz): 1.18 (d, 9H), 1.21 (d, 3H), 2.60 (d, 3H), 2.90 (dd, 2H), 5.70 (d, 2H), 6.73–8.15 (m, 7H). MS (ESI) m/z 503.20 (M+H$^+$)

Example 21

3-(3,4-Dihydroxy-phenyl)-2-hydrazino-2-methyl-propionic acid 2-phenoxy-ethyl ester (133)

Following the procedure described in Example 4 Step A for preparation of compound 107, and substituting methanol with 2-phenoxy-ethanol, provided the title compound. $^1$H NMR (CD$_3$OD, 400 MHz): 1.65 (s, 3H), 3.10 (dd, 2H), 4.40 (t, 2H), 4.70 (t, 2H), 6.60–6.52 (m, 8H). MS (ESI) m/z 347.27 (M+H$^+$).

Example 22

Ethyl 3-(3,4-dihydroxyphenyl)-2-[N'-(2,2-dimethyl-propionyloxy-methoxycarbonyl)-hydrazino]-2-methyl-propionate (134)

Step A: Ethyl 3-(3,4-dihydroxyphenyl)-2-hydrazino-2-methyl-propionate (135)

Following the procedure for preparation of compound 107, and substituting methanol with ethanol, provided the title compound, which was used in the next reaction without further purification.

Step B: Ethyl 3-(3,4-dihydroxyphenyl)-2-[N'-(2,2-dimethyl-propionyloxy-methoxycarbonyl)-hydrazino]-2-methyl-propionate (134)

To a pressure vessel containing compound 135 (1 g, 4 mmol) and triethylamine (11.2 mL, 80 mmol), chloroform (50 mL), and acetonitrile (20 mL) was added N,O-bis(trimethylsilyl)acetamide (3.3 mL, 13.2 mmol) and the resulting mixture was stirred until a clear solution is formed. A solution containing α-pivaloxymethyl-p-nitrophenyl carbonate (0.63 g, 4 mmol) in chloroform (10 mL) was then added and stirred at 55° C. for 48 h. After concentration, the residue was partitioned between 10% citric acid and ethyl acetate. The organic layer was separated and the aqueous layer was further extracted with ethyl acetate (3×20 mL). The combined organic extracts were dried over MgSO$_4$ and then concentrated in vacuo. Chromatography of the resulting residue on silica gel, eluting with hexane:ethyl acetate (7:3) to remove nitrophenol, then eluting with ethyl acetate/methanol/acetic acid (100:10:0.5) afforded the crude product. Further purification by reverse preparative HPLC gave 60 mg of the title compound. $^1$H NMR (CDCl$_3$, 400 MHz): 1.22 (s, 9H), 1.29 (t, 3H), 1.38 (s, 3H), 2.82 (dd, 2H), 5.75 (dd, 2H), 6.53 (dd, 1H), 6.71 (m, 2H). MS (ESI) m/z 413.37 (M+H$^+$).

Example 23

3-(3,4-dihydroxyphenyl)-2-[N'-(2,2-dimethyl-propionyloxy-methoxycarbonyl)-hydrazino]-2-methyl-propionic acid (136)

To a pressure vessel containing carbidopa (2.26 g, 10 mmol), triethylamine (37 mL, 50 mmol), chloroform (150 mL), and acetonitrile (50 mL) was added trimethylchlorosilane (6.3 mL, 50 mmol) and the mixture stirred until the carbidopa fully dissolved. A solution containing α-pivaloxymethyl-p-nitrophenyl carbonate (2.0 g, 7 mmol) in chloroform (20 mL) was added and stirred at 65° C. for 24 h. After removing the solvent, the mixture was partitioned with 10% citric acid and ethyl acetate. The organic layer was separated and the aqueous layer was further extracted with ethyl acetate (3×60 mL). The combined organic extracts were dried over MgSO$_4$ and then concentrated in vacuo. Chromatography of the resulting residue on silica gel, eluting with hexane:ethyl acetate (7:3) to remove nitrophenol, then eluting with ethyl acetate/methanol/acetic acid (100:10:1) gave 780 mg (20%) of the title compound. $^1$H NMR (CDCl$_3$, 400 MHz): 1.18 (s, 9H), 1.26 (s, 3H), 2.82 (dd, 2H), 5.70 (dd, 2H), 6.53 (dd, J=8 Hz, J=2 Hz, 1H), 6.46 (d, J=8 Hz, 1H), 6.68 (d, J=2 Hz). MS (ESI) m/z 385.10 (M+H$^+$).

Example 24

Methyl 2-{N'-[(3-Carboxypropionyloxymethoxy)carbonyl]-hydrazino}-3-(3,4-dihydroxy-phenyl)-2-methyl-propionate (147)

Step A: [(3-Benzyloxycarbonyl)propionyloxymethyl]-4-Nitrophenyl Carbonate (148)

To a solution of succinic acid monobenzyl ester (1.1 g, 5.28 mmol) and iodomethyl-p-nitrophenyl carbonate (1.9 g, 5.90 mmol) in 20 mL anhydrous chloroform was added silver carbonate (2.2 g, 7.97 mmol). The reaction mixture was heated to reflux for 5 h before cooling to room temperature. The mixture was then filtered through a pad of celite and the filtrate was diluted with 100 mL of ethyl acetate. The organic layer was washed with brine (3×50 mL), dried over MgSO$_4$ and concentrated in vacuo. The crude product was purified by radial chromatography (5% ethyl acetate/hexane to 40% ethyl acetate/hexane) to afford 1.5 g (68%) of the title compound.

Step B: Methyl 2-{N'-[((3-Benzyloxycarbonyl)propionyloxymethoxy)carbonyl]-hydrazino}-3-(3,4-dihydroxy-phenyl)-2-methyl-propionate (149)

To an ice cold solution of 107 (210 mg, 0.71 mmol) in 2 mL DMF was dropwise added triethylamine (0.39 mL, 2.79 mmol) and 148 (300 mg, 0.81 mmol) in DMF (2 mL). The resulting mixture was allowed to warm to room temperature over 1 h and stirred for 10 h. The reaction mixture was then diluted with 50 mL ethyl acetate and washed with saturated ammonium chloride (2×30 mL). The organic layer was separated, dried over MgSO$_4$ and concentrated in vacuo. The residue was purified by radial chromatography to afford 70 mg (20%) of the title compound.

Step C: Methyl 2-{N'-[(3-Carboxypropionyloxymethoxy)carbonyl]-hydrazino}-3-(3,4-dihydroxy-phenyl)-2-methyl-propionate (147)

To a flask containing 10 mg of 10% Pd—C was added a solution of 149 in 2 mL ethyl acetate under nitrogen. The resulting mixture was degassed several times, and then hydrogen gas was introduced (via balloon). The suspended mixture was stirred vigorously for 12 h. The reaction mixture was then filtered through a pad of celite. After removing the solvent under reduced pressure, the residue was purified by reverse phase LC/MS to afford 14 mg (25%) of the title compound. $^1$H-NMR (400 MHz, CD$_3$OD): δ 6.63 (d, J=8.0 Hz, 1H), 6.54 (d, J=1.6 Hz, 1H), 6.43 (dd, J=8.0, 1.6 Hz, 1H), 5.70 (s, 2H), 3.66 (s, 3H), 2.84 (Abq, J=26.8, 13.6 Hz, 2H), 2.54–2.63 (m, 4H), 1.24 (s, 3H). MS (ESI) m/z 415.2 (M+H$^+$).

Example 25

5-[3-(3,4-Dihydroxy-phenyl)-2-hydrazino-2-methyl-propionyl]-oxy-pentanoic acid (151)

Step A: 5-[3-(3,4-Bis-benzyloxy-phenyl)-2-(N'-tert-butoxycarbonyl-hydrazino)-2-methyl-propionyl]-oxypentanoic acid benzyl ester (152)

To a solution of 5-bromo-pentanoic acid benzyl ester (210 mg, 0.78 mmol) in 1 mL DMF was added 3-(3,4-bis-benzyloxy-phenyl)-2-(N'-tert-butoxycarbonyl-hydrazino)-2-methyl-propionic acid (329 mg, 0.65 mmol) and potassium bicarbonate (78 mg, 0.78 mmol). The resulting mixture was heated to 80° C. and stirred for 12 h. The reaction mixture was then cooled to room temperature and diluted with 50 mL of ethyl acetate. The organic layer was washed with 10% citric acid aqueous solution (2×20 mL) followed by brine (2×20 mL). The organic layer was dried over MgSO$_4$ and concentrated in vacuo. The crude residue was purified by radial chromatography (CH$_2$Cl$_2$ to 10% MeOH/CH$_2$Cl$_2$) to afford 210 mg (46%) of the title compound.

Step B: 5-[2-(N'-tert-Butoxycarbonyl-hydrazino)-3-(3,4-dihydroxy-phenyl)-2-methyl-propionyl]-oxy-pentanoic acid (153)

To a flask containing 40 mg of 10% Pd—C was added a solution of the above product in 6 mL of MeOH under nitrogen. The resulting reaction solution was degassed several times, then hydrogen gas was introduced via a balloon apparatus. After stirring vigorously for 12 h, the reaction mixture was filtered through a pad of celite and the filtrate was concentrated in vacuo.

Step C: 5-[3-(3,4-Dihydroxy-phenyl)-2-hydrazino-2-methyl-propionyl]-oxy-pentanoic acid (151)

The crude 153 was dissolved in 4 mL anhydrous CH$_2$Cl$_2$ and treated with 2 mL of trifluoroacetic acid at 0° C. The reaction mixture was allowed to warm to room temperature and stirred for 1 h. After removing the solvent under reduced pressure, the residue was purified by reverse phase LC/MS to afford 55 mg (26% overall yield) of the title compound: $^1$H-NMR (400 MHz, CD$_3$OD): δ 6.68 (d, J=8.0 Hz, 1H), 6.55 (d, J=1.6 Hz, 1H), 6.45 (dd, J=8.0, 1.6 Hz, 1H), 4.09–4.18 (m, 2H), 2.79–2.92 (Abq, J=36.8, 13.2 Hz, 2H), 2.30 (t, J=6.8 Hz, 2H), 1.59–1.68 (m, 4H), 1.42 (s, 3H). MS (ESI) m/z 327.2 (M+H$^+$).

Example 26

3-(3,4-Bis-ethoxycarbonyloxy-phenyl)-2-hydrazino-2-methyl-propionic acid carboxymethyl ester (154)

Step A: 3-(3,4-Bis-ethoxycarbonyloxy-phenyl)-2-(N'-tert-butoxycarbonyl-hydrazino)-2-methyl-propionic acid tert-butoxycarbonyl-methyl ester (155)

To an ice cold solution of 146 (410 mg, 1 mmol) in 4 mL of CH$_2$Cl$_2$ was added Et$_3$N (0.30 mL, 2.15 mmol) followed by ethyl chloroformate (0.2 mL, 2.09 mmol). The resulting mixture was allowed to warm to room temperature and stirred for 12 h. The mixture was then diluted with ethyl acetate (50 mL) and washed with 10% citric acid aqueous solution (2×30 mL), dried over MgSO$_4$, filtered and concentrated in vacuo. The crude product was purified by radial chromatography (CH$_2$Cl$_2$ to 10% MeOH/CH$_2$Cl$_2$) to afford 0.42 g of the title compound.

Step B: 3-(3,4-Bis-ethoxycarbonyloxy-phenyl)-2-hydrazino-2-methyl-propionic acid carboxymethyl ester (154)

Compound 155 was dissolved in 2 mL CH$_2$Cl$_2$ and treated with 1 mL trifluoroacetic acid at 0° C. The resulting mixture was allowed to warm to room temperature and stirred for 1 h. The reaction mixture was cooled to 0° C. again and a solution (1 mL) of 4 N HCl in dioxane was added. After stirring at room temperature for 2 h, the solvent was removed in vacuo. The crude residue was purified by reverse phase LC/MS to afford 103 mg (24% overall yield) of the title compound. $^1$H-NMR (400 MHz, CD$_3$OD): δ 7.14–7.22 (m, 3H), 4.49–4.69 (Abq, J=62.8, 14.8, 2H), 4.24–4.29 (m, 4H), 3.03–3.13 (q, J=13.6 Hz), 1.33 (t, J=6.0 Hz, 6H). MS (ESI) m/z 429.2 (M+H$^+$).

Example 27

(S)-3-(3,4-Bis-isobutyryloxy)phenyl-2-hydrazino-2-methylpropionic acid acetoxymethyl ester (160)

Following the procedure for preparation of compound 101, and substituting ethyl chloroformate with isobutyryl chloride, provided the title compound. $^1$H NMR (D$_2$O, 400 MHz): δ 1.11 (d, 6H), 1.13 (d, 6H), 1.39 (s, 3H), 1.99 (s, 3H), 2.70 (septet, 2H), 2.97 (dd, 2H), 5.86 (dd, 2H), 6.93–7.07 (m, 3H). MS (ES) m/z 439.28 (M+H$^+$).

Example 28

(S)-3-(3,4-Bis-isobutyryloxy)phenyl-2-hydrazino-2-methylpropionic acid 2,2-dimethyl-propionyloxymethyl ester (161)

Following the procedure for preparation of compound 101, and substituting ethyl chloroformate with isobutyryl chloride and bromomethylacetate with iodomethyl pivalate, provided the title compound. $^1$H NMR (CD$_3$OD, 400 MHz): δ 1.24 (s, 9H), 1.28 (d, 6H), 1.30 (d, 6H), 1.45 (s, 3H), 2.79 (septet, 2H), 2.93 (dd, 2H), 5.63 (dd, 2H), 7.10–7.13 (m, 3H). MS (ESI) m/z 481.28 (M+H$^+$).

Example 29

(S)-3-(3,4-Bis-propionyloxy)phenyl-2-hydrazino-2-methylpropionic acid acetoxymethyl ester (162)

Following the procedure for preparation of compound 101, and substituting ethyl chloroformate with propionyl chloride, provided the title compound. $^1$H NMR (CD$_3$OD, 400 MHz): δ 1.22 (t, 6H), 1.47 (s, 3H), 2.59 (q, 4H), 3.08 (dd, 2H), 5.83 (dd, 2H), 7.09–7.17 (m, 3H). MS (ESI) m/z 411.31 (M+H$^+$).

Example 30

(S)-3-[3,4-Bis-(2,2-dimethylpropionyloxy)phenyl]-2-hydrazino-2-methylpropionic acid acetoxymethyl ester (163)

Following the procedure for preparation of compound 101, and substituting ethyl chloroformate with 2,2-dimethylpropionyl chloride, provided the title compound. $^1$H NMR (CD$_3$OD, 400 MHz): δ 1.33 (s, 9H), 1.34 (s, 9H), 1.46 (s, 3H), 2.12 (s, 3H), 3.08 (dd, 2H), 5.83 (dd, 2H), 7.05–7.12 (m, 3H). MS (ESI) m/z 467.35 (M+H$^+$).

Example 31

(S)-3-[3,4-Bis-(2,2-dimethylpropionyloxy)phenyl]-2-hydrazino-2-methylpropionic acid 2,2-dimethyl-propionyloxymethyl ester (164)

Following the procedure for preparation of compound 101, and substituting ethyl chloroformate with 2,2-dimethylpropionyl chloride and bromomethylacetate with iodomethyl pivalate, provided the title compound. $^1$H NMR (CD$_3$OD, 400 MHz): δ 1.24 (s, 9H), 1.33 (s, 9h), 1.34 (s, 9H), 1.44 (s, 3H), 3.07 (dd, 2H), 5.87 (dd, 2H), 7.07–7.15 (m, 3H). MS (ESI) m/z 509.41 (M+H$^+$).

Example 32

(S)-3-(3,4-Bis-ethoxycarbonyloxy)phenyl-2-hydrazino-2-methylpropionic acids (1R)- and (1S)-isobutyryloxy-2-methylpropyl esters (165)

Compound 101 was treated with Boc anhydride to form compound 101a. To a suspension of 101a (270 mg, 0.57 mmol) and silver carbonate (198 mg, 0.72 mmol) in dichloromethane, 1-chloro-2-methylpropyl isobutyrate (172 mg, 1.5 mmol) was added and stirred at 38° C. for 16 h. After removing the solvent, the residue was partitioned between ethyl acetate and 10% citric acid. The organic phase was separated, dried over MgSO$_4$ and concentrated. The resulting residue was treated with 30% trifluoroacetic acid in dichloromethane at room temperature for 30 min. After removing the solvent, the resulting residue was purified by reverse phase preparative HPLC to afford 19 mg of the title compounds as a mixture of two diastereoisomers. $^1$H NMR (CD$_3$OD, 400 MHz): δ 1.05 (d, 6H), 1.20 (t, 6H), 1.39 (d, 6H), 1.38 (s, 1.7H), 1.50 (s, 1.3H), 2.1 (m, 1H), 2.62 (m, 1H), 3.10 (m 2H), 4.3 (q, 4H), 6.6 (dd, 0.6H), 6.70 (dd, 0.4H), 7.18–7.24 (m, 3H). MS (ESI) m/z 513.32 (M+H$^+$).

Example 33

(S)-3-(3,4-Bis-ethoxycarbonyloxy)phenyl-2-hydrazino-2-methylpropionic acids (1R)- and (1S)-acetoxy 2-methylpropyl esters (166)

Following the procedure for preparation of compound 165, and substituting 1-chloro-2-methylpropyl isobutyrate with 1-chloro-2-methylpropyl acetate, provided the title compounds as a mixture of two diastereoisomers. $^1$H NMR (CD$_3$OD, 400 MHz): δ 1.01 (d, 6H), 1.37 (t, 6H), 1.40(s, 1.2H), 1.46 (s, 1.8H), 3.11 (dd, 2H), 4.30 (q, 4H) 6.62 (dd, 0.4H), 6.68 (dd, 0.6H), 7.18–7.27 (m, 3H). MS (ESI) m/z 485.21 (M+H$^+$).

Example 34

(S)-3-(3,4-Bis-ethoxycarbonyloxy)phenyl-2-hydrazino-2-methylpropionic acids 1(R)- and 1(S)-isobutyryloxyethyl esters (167)

Following the procedure for preparation of compound 165, and substituting 1-chloro-2-methylpropyl isobutyrate with 1-chloroethyl isobutyrate, provided the title title compounds as a mixture of two diastereoisomers. $^1$H NMR (CD$_3$OD, 400 MHz): δ 1.18 (d, 6H), 2.36 (t, 6H), 1.41 (s, 1.3H), 1.26 (s, 1.7H), 1.34 (d, 1.3H), 1.36 (d, 1.7H), 2.60 (q, 1H), 2.98–3.17 (m, 2H), 4.28 (q, 4H), 6.88 (dd, 1H), 7.16–7.28 (m, 3H). MS (ESI) m/z 485.27 (M+H$^+$).

Example 35

(S)-3-(3,4-Bis-ethoxycarbonyloxy)phenyl-2-hydrazino-2-methylpropionic acid isobutyryloxymethyl ester (168)

Following the procedure for preparation of compound 165, and substituting 1-chloro-2-methylpropyl isobutyrate with chloromethyl isobutyrate, provided the title compound. $^1$H NMR (CD$_3$OD, 400 MHz): δ 1.20 (d, 6H), 1.35 (t, 6H), 1.44 (s, 3H), 2.65 (septet, 1H), 3.10 (dd, 2H), 4.30 (q, 4H), 5.88 (dd, 2H), 7.17–7.25 (m, 3H). MS (ESI) m/z 471.25 (M+H$^+$).

Example 36

(S)-3-(3,4-Dihydroxy)phenyl-2-hydrazino-2-methylpropionic acid 2-methylbenzoyloxymethyl ester (169)

Following the procedure for preparation of compound 104, and substituting bromomethyl acetate with iodomethyl 2-methylbenzoate followed by trifluoro acetic acid (TFA) treatment, provided the title compound. $^1$H NMR (CD$_3$OD, 400 MHz): δ 1.46 (s, 3H), 2.60 (s, 3H), 2.93 (dd, 2H), 6.08 (s, 2H), 6.44–6.64 (m, 3H), 7.33–7.99 (m, 4H). MS (ESI) m/z 375.26 (M+H$^+$).

Example 37

(S)-3-(3,4-Dihydroxy)phenyl-2-hydrazino-2-methylpropionic acid 2,6-dimethylbenzoyloxymethyl ester (170)

Following the procedure for preparation of compound 104, and substituting bromomethyl acetate with iodomethyl 2,6-dimethylbenzoate followed by TFA treatment, provided the title compound. $^1$H NMR (CD$_3$OD, 400 MHz): δ 1.40 (s, 3H), 2.06 (s, 6H), 2.93 (dd, 2H), 5.98 (dd, 2H), 6.37–6.55 (m, 3H), 6.98–7.21 (m, 3H). MS (ESI) m/z 389.28 (M+H$^+$).

Example 38

(S)-3-(3,4-Dihydroxy)phenyl-2-hydrazino-2-methylpropionic acid ethoxycarbonyloxymethyl ester (171)

Step A: (S)-2-(N'-tert-Butoxycarbonyl)hydrazino-3-(3,4-dihydroxy)phenyl-2-methylpropionic acid ethoxycarbonyloxymethyl ester (172)

A mixture of chloromethyl ethyl carbonate (0.556 g, 4 mmol) and sodium iodide (600 mg, 4 mmol) in acetone was stirred at room temperature for 1 h. To that mixture was added CsHCO$_3$ (0.776 g, 4 mmol) and compound 102 (1.33 g, 4 mmol), respectively. The resulting mixture was stirred at room temperature for 16 h. After removing the solvent under reduced pressure, the residue was partitioned between ethyl acetate and 10% citric acid. The organic phase was separated, dried over MgSO$_4$, and concentrated. The resulting residue was purified by silica gel chromatography, eluting with hexane: ethyl acetate (5:5) to afford the title compound.

Step B: (S)-3-(3,4-Dihydroxy)phenyl-2-hydrazino-2-methylpropionic acid ethoxycarbonyloxymethyl ester (171)

The above compound 172 was treated with 30% trifluoroacetic acid in dichloromethane at room temperature for 30 min. After removing the solvent, the resulting residue was purified by reverse phase preparative HPLC to afford 190 mg of the title compound. $^1$H NMR (D$_2$O, 400 MHz): δ 1.14 (t, 3H), 1.38 (s, 3H), 2.84 (dd, 2H), 4.10 (q, 2H), 5.62 (dd, 2H), 6.42–6.66 (m, 3H). MS (ESI) m/z 329.23 (M+H$^+$).

Example 39

(S)-3-(3,4-Bis-ethoxycarbonyloxy)phenyl-2-hydrazino-2-methylpropionic acid ethoxycarbonyloxymethyl ester (173)

Following the procedure for preparation of compound 106, and substituting compound 108 with compound 172, provided the title compound. $^1$H NMR (CD$_3$OD, 400 MHz): δ 1.30 (t, 3H), 1.34 (t, 6H), 1.44 (s, 3H), 3.08 (dd, 2H), 4.28 (q, 6H), 5.85 (dd, 2H), 7.15–7.23 (m, 3H). MS (ESI) m/z 473.21 (M+H$^+$).

Example 40

(S)-3-(3,4-Diacetoxy)phenyl-2-hydrazino-2-methylpropionic acid ethoxycarbonyloxymethyl ester (174)

Following the procedure for preparation of compound 106, and substituting ethyl chloroformate with acetyl chloride and compound 108 with compound 172, provided the title compound. $^1$H NMR (CD$_3$OD, 400 MHz): δ 1.31 (t, 3H), 1.45 (s, 3H), 2.25 (s, 6H), 3.08 (dd, 2H), 4.25 (q, 2H), 5.85 (dd, 2H), 7.10–7.18 (m, 3H). MS (ESI) m/z 413.17 (M+H$^+$).

Example 41

(S)-3-(3,4-Bis-isobutyryloxy)phenyl-2-hydrazino-2-methylpropionic acid ethoxycarbonyloxymethyl ester (175)

Step A: (S)-3-(3,4-Bis-isobutyryloxy)phenyl-2-(N'-tert-butoxycarbonyl)hydrazino-2-methylpropionic acid (176)

A mixture of compound 102, TEA and isobutyric anhydride in dichloromethane was stirred at room temperature for 2 h. After working up with diluted HCl and extracted with EtOAc, the organic layer was separated and dried over Na$_2$SO$_4$. Removal of the solvent gave the title compound, which was used in the next step without further purification.

Step B: (S)-3-(3,4-Bis-isobutyryloxy)phenyl-2-hydrazino-2-methylpropionic acid ethoxycarbonyloxymethyl ester (175)

Following the procedure for preparation of compound 165, and substituting 1-chloro-2-methylpropyl isobutyrate with chloromethyl ethyl carbonate and compound 110 with compound 176, provided the title compound. $^1$H NMR (CD$_3$OD, 400 MHz): δ 1.30 (d, 6H), 1.32 (t, 3H), 1.41 (s, 3H), 2.80 (septet, 2H), 3.08 (dd, 2H), 4.26 (q, 2H), 5.85 (dd, 2H), 7.10–7.15 (m, 3H). MS (ESI) m/z 469.26 (M+H$^+$).

Example 42

(S)-3-(3,4-Bis-isobutyryloxy)phenyl-2-hydrazino-2-methylpropionic acids (1R)- and (1S)-ethoxycarbonyloxyethyl esters (177)

Following the procedure for preparation of compound 175, and substituting chloromethyl ethyl carbonate with 1-chloroethyl ethyl carbonate, provided the title compounds as a mixture of two diastereoisomers. $^1$H NMR (CD$_3$OD, 400 MHz): δ 1.28 (d, 12H), 1.30 (s, 3H), 1.45 (s, 1.3H), 1.48 (s, 1.7H), 1.52 (d, 1.3H), 1.58 (d, 1.7H), 2.80 (septet, 2H), 3.08 (dd, 2H), 4.22 (q, 2H), 5.77 (dd, 0.4H), 5.80 (dd, 0.6H), 7.08–7.19 (m, 3H). MS (ESI) m/z 483.38 (M+H$^+$).

Example 43

(S)-3-(3,4-Bis-ethoxycarbonyloxy)phenyl-2-hydrazino-2-methylpropionic acids (1R)- and (1S)-ethoxycarbonyloxyethyl esters (178)

Following the procedure for preparation of compound 175, and substituting 1-chloro-2-methylpropyl isobutyrate with 1-chloroethyl ethyl carbonate and isobutyric anhydride with ethylchloroformate, provided the title compounds as a mixture of two diastereoisomers. $^1$H NMR (CD$_3$OD, 400 MHz): δ 1.15 (t, 3H), 1.18 (t, 6H), 1.35 (d, 3H), 1.39 (s, 3H), 2.85–3.08 (m, 2H), 4.06 (q, 2H), 4.16 (q, 4H), 6.77 (dd, 0.4H), 6.81 (dd, 0.6H), 7.05–7.16 (m, 3H). MS (ESI) m/z 487.34 (M+H$^+$).

Example 44

(S)-3-(3,4-Dihydroxy)phenyl-2-hydrazino-2-methylpropionic acids (1R)- and (1S)-ethoxycarbonyloxyethyl esters (179)

Step A: (S)-3-(3,4-Bis-tert-butoxycarbonyloxy)phenyl-2-(N'-tert-butoxycarbonylhydrazino)-2-methylpropionic acid (180)

Following the procedure for preparation of compound 175, and substituting ethylchloroformate with Boc anhydride, provided the title compound. $^1$H NMR ((CDCl$_3$, 400 MHz): δ 1.34 (s, 3H), 1.44 (s, 9H), 1.56 (s, 18H), 3.08 (dd, 2H), 7.11–7.18 (m, 3H). MS (ESI) m/z 527.32 (M+H$^+$).

Step B: (S)-3-(3,4-Dihydroxy)phenyl-2-hydrazino-2-methylpropionic acids (1R)- and (1S)-ethoxycarbonyloxyethyl esters (179)

Following the procedure for preparation of compound 178, and the resulting mixture was treated with TFA to afford the title compounds as a mixture of two diastereoisomers. $^1$H NMR (CD$_3$OD, 400 MHz): δ 1.13 (t, 3H), 1.36 (s, 3H), 1.40 (d, 3H), 2.75–2.95 (m, 2H), 4.09 (q, 2H), 6.44. (d, 0.4H), 6.47 (d, 0.6H), 6.55–6.70 (m, 3H). MS (ESI) m/z 343.25 (M+H$^+$).

Example 45

(S)-3-(3,4-Dihydroxy)phenyl-2-hydrazino-2-methylpropionic acids (1R)- and (1S)-isopropoxycarbonyloxyethyl esters (181)

Following the procedure for preparation of compound 175, and substituting chloromethyl ethyl carbonate with 1-chloroethyl isopropyl carbonate and isobutyric anhydride with Boc anhydride, provided the title compounds as a mixture of two diastereoisomers. $^1$H NMR (D$_2$O, 400 MHz): δ 1.12 (d, 6H), 1.32–1.39 (m, 6H), 2.77–2.98 (m, 2H), 3.08 (dd, 2H), 6.46 (m, 0.45H), 6.48 (m, 0.55H), 6.53–6.65 (m, 3H). MS (ESI) m/z 357.24 (M+H$^+$).

Example 46

(S)-3-(3,4-Bis-isobutyryloxy)phenyl-2-hydrazino-2-methyl)propionic acids (1R)- and (1S)-isopropoxycarbonyloxyethyl esters (182)

Following the procedure for preparation of compound 175, and substituting chloromethyl ethyl carbonate with 1-chloroethyl isopropyl carbonate, provided the title compounds as a mixture of two diastereoisomers. $^1$H NMR (CD$_3$OD, 400 MHz): δ 1.26–1.33 (m, 18), 1.45 (s, 1.3H), 1.48 (s, 1.7H), 1.53 (d, 1.3H), 1.57 (d, 1.7H), 2.80 (septet, 2H), 2.98–3.16 (m, 2H), 6.75 (q, 0.4H), 6.79 (q, 0.6H), 7.08–7.18 (m, 3H). MS (ESI) m/z 497.31 (M+H$^+$).

Example 47

(S)-3-(3,4-Dihydroxy)phenyl-2-hydrazino-2-methylpropionic acids (1R)- and (1S)-cyclohexyloxycarbonyloxyethyl esters (183)

Step A: 1-chloroethyl cyclohexyl carbonate (184)

To a mixture of cyclohexanol (10.9 g, 10.9 mmol), pyridine (8.62 g, 10.9 mmol) in dichloromethane was added 1-chloroethyl chloroformate (15.59, 10.9 mmol) at ° C. The resulting mixture was stirred at room temperature for 60 min. The mixture was partitioned between hexane and 10% citric acid. The organic phase was separated and dried over MgSO$_4$. Removal of the solvent gave the title compound, which was used in the next reaction without further purification.

Step B: (S)-3-(3,4-Dihydroxy)phenyl-2-hydrazino-2-methylpropionic acids (1R)- and (1S)-cyclohexyloxycarbonyloxyethyl esters (183)

Following the procedure for preparation of compound 175, and substituting chloromethyl ethyl carbonate with 1-chloroethyl cyclohexyl carbonate, provided the title compounds as a mixture of two diastereoisomers. $^1$H NMR (D$_2$O, 400 MHz): δ 1.08–1.24 (m, 3H), 1.33–1.39 (m, 9H), 1.42–1.58 (m, 2H), 1.64–1.75 (m, 2H), 2.72–2.94 (m, 2H), 4.52 (m, 1H), 6.43–6.70 (m, 4H). MS (ESI) m/z 397.33 (M+H$^+$).

Example 48

(S)-3-(3,4-Dihydroxy)phenyl-2-hydrazino-2-methyl-propionic acids (1R)- and (1S)-{[(2,6-dimethylcyclohexyloxy)carbonyl]oxy}ethyl esters (185)

Following the procedure for preparation of compound 183, and substituting cyclohexanol with 2,6-dimethylcyclohexanol, provided the title compounds as a mixture of two diastereoisomers. MS (ESI) m/z 425.31 (M+H$^+$).

Example 49

(S)-3-(3,4-Dihydroxy)phenyl-2-hydrazino-2-methyl-propionic acids (1R)- and (1S)-{[(1,3,3-trimethyl-bicyclo[2.2.1]hept-2-yloxy)carbonyl]oxy}ethyl esters (186)

Following the procedure for preparation of compound 183, and substituting cyclohexanol with (1R)-endo-(+)-fenchyl, provided the title compounds as a mixture of two diastereoisomers. MS (ESI) m/z 451.31 (M+H$^+$).

Example 50

(S)-3-(3,4-Dihydroxy)phenyl-2-hydrazino-2-methyl-propionic acids (1R)- and (1S)-{[(adamantan-2-yloxy)carbonyl]oxy}ethyl esters (187)

Following the procedure for preparation of compound 183, and substituting cyclohexanol with 2-adamantanol, provided the title compounds as a mixture of two diastereoisomers. MS (ESI) m/z 449.31 (M+H$^+$).

General Procedure for Preparation of Compounds 188–209 and 211–224 Via Alkylation of a Carbidopa Derivative with a Halide To a mixture of compound 102 (1 mmol) and cesium hydrogen carbonate (1.2 mmol) in dimethylacetamide or acetone was added a halide compound 17 (1.2 mmol). After stirring at appropriate temperature (room temperature to 60° C.) for 16 h, the mixture was filtrated and the filtrate was concentrated under reduced pressure to give an oily residue. Chromatography (SiO$_2$, 3:97 methanol/ethyl acetate or 40:60 ethyl acetate/hexane) of the residue gave Boc protected carbidopa ester (yield: 45% to 75%). The Boc protecting group was removed using 30% trifluoroacetic acid/dichloromethane for 30 min at room temperature. The product was purified by HPLC (0.05% formic acid/water/acetonitrile). In some cases, the formic acid salt was converted to an HCl salt by adding 1 eq. of 0.1N HCl solution. The final product was obtained upon re-lyophilization.

Example 51

Phenylmethyl (S)-3-(3,4-dihydroxyphenyl)-2-hydrazino-2-methylpropanoate (188)

The title compound (76 mg) was prepared as a white solid according to the general procedure. $^1$H NMR (CD$_3$OD): δ 1.47 (s, 3H), 2.91 (dd, J=13.6 Hz, 2H), 5.19 (dd, J=12.4 Hz, 2H), 6.36 (dd, J=7.6 Hz, 1H), 6.58 (s, 1H), 6.62 (d, J=7.6 Hz, 1H), 7.33 (m, 5H). MS (ESI) m/z 317.2 (M+H$^+$).

Example 52

(4-Methylphenyl)methyl (S)-3-(3,4-dihydroxyphenyl)-2-hydrazino-2-methylpropanoate (189)

The title compound was prepared as a white solid according to the general procedure. $^1$H NMR (CD$_3$OD): δ 1.45 (s, 3H), 2.35 (s, 3H), 2.90 (m, 2H), 5.14 (dd, J=12.0 Hz, 2H), 6.33 (dd, J=7.6 Hz, 1H), 6.57 (s, 1H), 6.61 (d, J=7.6 Hz, 1H), 7.17 (dd, J=8.4 Hz, 4H). MS (ESI) m/z 331.2 (M+H$^+$).

Example 53

(3-Methoxyphenyl)methyl (S)-3-(3,4-dihydroxyphenyl)-2-hydrazino-2-methylpropanoate (190)

The title compound was prepared as a white solid according to the general procedure. $^1$H NMR (CD$_3$OD): δ 1.44 (s, 3H), 2.87 (dd, J=13.6 Hz, 2H), 3.79 (s, 3H), 5.13 (dd, J=12.0 Hz, 2H), 6.36 (dd, J=7.6 Hz, 1H), 6.57 (s, 1H), 6.63 (d, J=7.6 Hz, 1H), 6.90 (m, 4H), 7.26 (t, J=7.6 Hz, 1H). MS (ESI) m/z 347.2 (M+H$^+$).

Example 54

4-Pyridylmethyl (S)-3-(3,4-dihydroxyphenyl)-2-hydrazino-2-methylpropanoate (191)

The title compound was prepared as a white solid according to the general procedure. $^1$H NMR (CD$_3$OD): δ 1.60 (s, 3H), 2.95 (dd, J=13.6 Hz, 2H), 5.74 (s, 2H), 6.49 (dd, J=8 Hz, 1H), 6.51 (d, J=2 Hz, 1H), 6.63 (d, J=8 Hz, 1H), 7.75 (d, J=6.8 Hz, 2H), 8.75 (d, J=6.8 Hz, 2H). MS (ESI) m/z 318.1 (M+H$^+$).

Example 55

3-Pyridylmethyl (S)-3-(3,4-dihydroxyphenyl)-2-hydrazino-2-methylpropanoate (192)

The title compound was prepared as a white solid according to the general procedure. $^1$H NMR (CD$_3$OD): δ 1.60 (s, 3H), 2.95 (dd, J=13.6 Hz, 2H), 5.37 (s, 2H), 6.42 (d, J=8 Hz, 1H,), 6.44 (s, 1H), 6.60 (d, J=8 Hz, 1H), 8.02 (dd, J=8 Hz, 1H), 8.37 (d, J=8 Hz, 1H), 8.73 (s, 1H), 8.82 (d, J=6 Hz, 1H). MS (ESI) m/z 318.1 (M+H$^+$).

Example 56

(2-Fluorophenyl)methyl (S)-3-(3,4-dihydroxyphenyl)-2-hydrazino-2-methylpropanoate (193)

The title compound was prepared as a white solid according to the general procedure. $^1$H NMR (CD$_3$OD): δ 1.46 (s, 3H), 2.90 (dd, J=13.6 Hz, 2H), 5.23 (dd, J=12.4 Hz, 2H), 6.36 (d, J=7.6 Hz, 1H), 6.57 (s, 1H), 6.61 (d, J=7.6 Hz, 1H), 7.14 (m, 2H), 7.38 (m, 2H). MS (ESI) m/z 335.1 (M+H$^+$).

Example 57

(3-Fluorophenyl)methyl (S)-3-(3,4-dihydroxyphenyl)-2-hydrazino-2-methylpropanoate (194)

The title compound was prepared as a white solid according to the general procedure. $^1$H NMR (CD$_3$OD): δ 1.48 (s, 3H), 2.92 (dd, J=13.6 Hz, 2H), 5.20 (dd, J=12.4 Hz, 2H), 6.36 (d, J=7.6 Hz, 1H), 6.57 (s, 1H), 6.63 (d, J=7.6 Hz, 1H), 7.10 (m, 3H), 7.38 (m, 1H); MS (ESI) m/z 335.2 (M+H$^+$).

Example 58

(4-Fluorophenyl)methyl (S)-3-(3,4-dihydroxyphenyl)-2-hydrazino-2-methylpropanoate (195)

The title compound was prepared as a white solid according to the general procedure. $^1$H NMR (CD$_3$OD): δ 1.47 (s, 3H), 2.90 (m, 2H), 5.16 (dd, J=12.4 Hz, 2H), 6.36 (dd, J=7.6 Hz, 1H), 6.57 (s, 1H), 6.63 (d, J=7.6 Hz, 1H), 7.1 (dd, J=8.4 Hz, 2H), 7.33 (dd, J=8.8 Hz, 2H). MS (ESI) m/z 335.1 (M+H$^+$).

Example 59

(4-Chlorophenyl)methyl (S)-3-(3,4-dihydroxyphenyl)-2-hydrazino-2-methylpropanoate (196)

The title compound was prepared as a white solid according to the general procedure. $^1$H NMR (CD$_3$OD): δ 1.47 (s, 3H), 2.90 (dd, J=13.6 Hz, 2H), 5.16 (dd, J=12.8 Hz, 2H), 6.36 (d, J=8.4 Hz, 1H), 6.57 (s, 1H), 6.63 (d, J=8.4 Hz, 1H), 7.28 (d, J=8.0 Hz, 2H), 7.38 (d, J=8.0 Hz, 2H). MS (ESI) m/z 351.2 (M+H$^+$).

Example 60

(3-Trifluoromethylphenyl)methyl (S)-3-(3,4-dihydroxyphenyl)-2-hydrazino-2-methylpropanoate (197)

The title compound was prepared as a white solid according to the general procedure. $^1$H NMR (CD$_3$OD): δ 1.45 (s, 3H), 2.88 (dd, J=13.6 Hz, 2H), 5.24 (dd, J=12.4 Hz, 2H), 6.35 (d, J=7.6 Hz, 1H), 6.56 (s, 1H), 6.61 (d, J=7.6 Hz, 1H), 7.59 (m, 4H). MS (ESI) m/z 385.2 (M+H$^+$).

Example 61

(4-Trifluoromethylphenyl)methyl (S)-3-(3,4-dihydroxyphenyl)-2-hydrazino-2-methylpropanoate (198)

The title compound was prepared as a white solid according to the general procedure. $^1$H NMR (CD$_3$OD): δ 1.47 (s, 3H), 2.88 (dd, J=13.6 Hz, 2H), 5.23 (dd, J=12.4 Hz, 2H), 6.38 (d, J=7.6 Hz, 1H), 6.57 (s, 1H), 6.63 (d, J=7.6 Hz, 1H), 7.10 (dd, J=8.4 Hz, 4H). MS (ESI) m/z 385.2 (M+H$^+$).

Example 62

2-Phenoxyethyl (S)-3-(3,4-dihydroxyphenyl)-2-hydrazino-2-methylpropanoate (199)

The title compound was prepared as a white solid using 2-bromo-1-phenoxyethane according to the general procedure. $^1$H NMR (CD$_3$OD): δ 1.48 (s, 3H), 2.92 (dd, J=13.6 Hz, 2H), 4.20 (t, J=4.8 Hz, 2H), 4.52 (m, 2H), 6.49 (d, J=8.0 Hz, 1H), 6.61 (s, 1H), 6.63 (d, J=8.0 Hz, 1H), 6.91 (m, 3H), 7.13 (m, 2H). MS (ESI) m/z 347.3 (M+H$^+$).

Example 63

2-(4-Methylphenoxy)ethyl (S)-3-(3,4-dihydroxyphenyl)-2-hydrazino-2-methylpropanoate (200)

The title compound was prepared as a white solid using 2-bromo-1-(4-methylphenoxy)ethane according to the general procedure. $^1$H NMR (CD$_3$OD): δ 1.46 (s, 3H), 2.27 (s, 3H), 2.92 (dd, J=13.6 Hz, 2H), 4.19 (t, J=4.8 Hz, 2H), 4.51 (m, 2H), 6.49 (d, J=8.0 Hz, 1H), 6.61 (s, 1H), 6.63 (d, J=8.0 Hz, 1H), 6.82 (m, 2H), 7.08 (d, J=8.4 Hz, 2H). MS (ES) m/z 361.2 (M+H$^+$).

Example 64

2-(3-Methylphenoxy)ethyl (S)-3-(3,4-dihydroxyphenyl)-2-hydrazino-2-methylpropanoate (201)

The title compound was prepared as a white solid using 2-bromo-1-(3-methylphenoxy)ethane according to the general procedure. $^1$H NMR (CD$_3$OD): δ 1.47 (s, 3H), 2.31 (s, 3H), 2.99 (dd, J=13.6 Hz, 2H), 4.21 (t, J=4.8 Hz, 2H), 4.51 (m, 2H), 6.49 (d, J=8.0 Hz, 1H), 6.61 (s, 1H), 6.63 (d, J=8.0 Hz, 1H), 6.74 (m, 3H), 7.15 (t, J=7.6 Hz, 1H). MS (ESI) m/z 361.3 (M+H$^+$).

Example 65

2-(4-n-Butylphenoxy)ethyl (S)-3-(3,4-dihydroxyphenyl)-2-hydrazino-2-methylpropanoate (202)

The title compound was prepared as a white solid using 2-bromo-1-(4-n-butylphenoxy)ethane according to the general procedure. $^1$H NMR (CD$_3$OD): δ 0.94 (t, J=6.8 Hz, 3H), 1.32 (m, 2H), 1.45 (s, 3H), 1.57 (m, 2H), 2.55 (t, J=8.0 Hz, 2H), 2.89 (m, 2H), 4.21 (t, J=4.4 Hz, 2H), 4.52 (m, 2H), 6.50 (d, J=8.4 Hz, 1H), 6.61 (s, 1H), 6.64 (d, J=8.4 Hz, 1H), 6.84 (d, J=8.4 Hz, 2H), 7.08 (d, J=8.8 Hz, 2H). MS (ESI) m/z 403.2 (M+H$^+$).

Example 66

2-(4-Methoxyphenoxy)ethyl (S)-3-(3,4-dihydroxyphenyl)-2-hydrazino-2-methylpropanoate (203)

The title compound was prepared as a white solid using 2-bromo-1-(4-methoxyphenoxy)ethane according to the general procedure. $^1$H NMR (CD$_3$OD): δ 1.47 (s, 3H), 2.92 (dd, J=13.6 Hz, 2H), 3.74 (s, 3H), 4.17 (m, J=4.8 Hz, 2H), 4.49 (m, 2H), 6.50 (d, J=8.4 Hz, 1H), 6.61 (s, 1H), 6.64 (d, J=8.0 Hz, 1H), 6.86 (m, 4H). MS (ESI) m/z 377.2 (M+H$^+$).

Example 67

2-(2-Fluorophenoxy)ethyl (S)-3-(3,4-dihydroxyphenyl)-2-hydrazino-2-methylpropanoate (204)

The title compound was prepared as a white solid using 2-bromo-1-(2-fluorophenoxy)ethane according to the general procedure. $^1$H NMR (CD$_3$OD): δ 1.45 (s, 3H), 2.90 (m, 2H), 4.31 (m, 2H), 4.54 (m, 2H), 6.50 (d, J=7.6 Hz, 1H), 6.60 (s, 1H), 6.64 (d, J=8.0 Hz, 1H), 6.95 (m, 1H), 7.10 (m, 3H). MS (ESI) m/z 365.2 (M+H$^+$).

Example 68

2-(3-Fluorophenoxy)ethyl (S)-3-(3,4-dihydroxyphenyl)-2-hydrazino-2-methylpropanoate (205)

The title compound was prepared as a white solid using 2-bromo-1-(3-fluorophenoxy)ethane according to the general procedure. $^1$H NMR (CD$_3$OD): δ 1.46 (s, 3H), 2.90 (m, 2H), 4.24 (m, 2H), 4.52 (t, J=4.0 Hz, 2H), 6.50 (d, J=8.0 Hz, 1H), 6.70 (m, 5H), 7.27 (q, J=8.0 Hz, 1H). MS (ESI) m/z 365.3 (M+H$^+$).

Example 69

2-(4-Fluorophenoxy)ethyl (S)-3-(3,4-dihydroxyphenyl)-2-hydrazino-2-methylpropanoate (206)

The title compound was prepared as a white solid using 2-bromo-1-(4-fluorophenoxy)ethane according to the general procedure. $^1$H NMR (CD$_3$OD): δ 1.46 (s, 3H), 2.12 (q, J=2.0 Hz, 2H), 2.91 (dd, J=13.6 Hz, 2H), 3.96 (m, 2H), 4.36 (m, 2H), 6.45 (d, J=7.6 Hz, 1H), 6.58 (s, 1H), 6.67 (d, J=7.6 Hz, 1H), 6.90 (m, 2H), 7.25 (m, 2H). MS (ESI) m/z 365.2 (M+H$^+$).

Example 70

2-(2-Chlorophenoxy)ethyl (S)-3-(3,4-dihydroxyphenyl)-2-hydrazino-2-methylpropanoate (207)

The title compound was prepared as a white solid using 2-bromo-1-(2-chlorophenoxy)ethane according to the general procedure. $^1$H NMR (CD$_3$OD): δ 1.47 (s, 3H), 2.93 (dd, J=13.6 Hz, 2H), 4.31 (m, 2H), 4.55 (m, 2H), 6.49 (dd, J=8.0 Hz, 1H), 6.61 (s, 1H), 6.62 (d, J=8.4 Hz, 1H), 6.95 (t, J=7.2 Hz, 1H), 7.09 (d, J=8.0 Hz, 1H), 7.27 (t, J=7.6 Hz, 1H), 7.36 (d, J=8.0 Hz, 1H). MS (ESI) m/z 381.2 (M+H$^+$).

Example 71

2-(4-Chlorophenoxy)ethyl (S)-3-(3,4-dihydroxyphenyl)-2-hydrazino-2-methylpropanoate (208)

The title compound was prepared as a white solid using 2-bromo-1-(4-chlorophenoxy)ethane according to the general procedure. $^1$H NMR (CD$_3$OD): δ 1.46 (s, 3H), 2.92 (dd, J=13.6 Hz, 2H), 4.21 (t, J=4.0 Hz, 2H), 4.51 (m, 2H), 6.49 (d, J=8.0 Hz, 1H), 6.61 (s, 1H), 6.64 (d, J=8.4 Hz, 1H), 6.92 (m, 2H), 7.26 (m, 2H). MS (ESI) m/z 381.2 (M+H$^+$).

Example 72

(4-Chlorophenoxy)methyl (S)-3-(3,4-dihydroxyphenyl)-2-hydrazino-2-methylpropanoate (209)

The title compound was prepared as a white solid using 4-chloro-1-(chloromethoxy)benzene according to the general procedure. $^1$H NMR (CD$_3$OD): δ 1.38 (s, 3H), 2.82 (dd, J=13.6 Hz, 2H), 5.81 (dd, J=6 Hz, J=16 Hz, 2H), 6.40 (d, J=8.0 Hz, 1H), 6.57 (s, 1H), 6.62 (d, J=8.4 Hz, 1H), 6.93 (d, J=10 Hz, 2H), 7.79 (d, J=10 Hz, 2H). MS (ESI) m/z 367.2 (M+H$^+$).

Example 73

(4-Chlorophenoxy)methyl (S)-3-(3,4-diethoxycarbonyloxyphenyl)-2-hydrazino-2-methylpropanoate (210)

To a mixture of Boc protected (4-chlorophenoxy)methyl (2S)-3-(3,4-dihydroxyphenyl)-2-hydrazino-2-methylpropanoate (639 mg, 1.37 mmol) and triethylamine (0.38 mL, 2.74 mmol) in dry dichloromethane was added diethyl pyrocarbonate (0.41 mL, 2.74 mmol) and a catalytic amount of 4-dimethylaminopyridine (DMAP), respectively, at 0° C. After stirring at 0° C. to room temperature for 2 h. the reaction was quenched with 10% citric acid, and the mixture was extracted with dichloromethane. The organic phase was separated and dried over sodium sulfate. After removing the solvent under reduced pressure, chromatography (SiO2, 20% ethyl acetate/hexane) of the residue gave 650 mg (78%) of Boc protected (2S)-3-(3,4-diethoxycarbonyloxyphenyl)-2-hydrazino-2-methylpropanoate, which was treated with 30%TFA/DCM at room temperature for 30 min to remove Boc. After removing the solvent, the residue was purified by HPLC (0.05% trifluoroacetic acid/water/acetonitrile) to give 100 mg of the title compound as a white powder. $^1$H NMR (CD$_3$OD): δ 1.32 (s, 3H), 1.27 (t, J=7.2 Hz, 3H), 1.28 (t, J=7.2 Hz, 3H), 2.95 (dd, J=13.6 Hz, 2H), 4.34 (q, J=7.2 Hz, 2H), 4.35 (q, J=7.2 Hz, 2H), 5.84 (dd, J=6 Hz, J=14 Hz, 2H), 7.07 (d, J=8.0 Hz, 1H), 7.15 (s, 1H), 7.24 (d, J=8.4 Hz, 1H), 7.10 (d, J=8 Hz, 2H), 7.38 (d, J=8 Hz, 2H). MS (ESI) m/z 513.1 (M+H$^+$).

Example 74

(Phenoxycarbonyl)methyl (S)-3-(3,4-dihydroxyphenyl)-2-hydrazino-2-methylpropanoate (211)

The title compound was prepared as a white solid using phenyl 2-bromoacetate according to the general procedure. $^1$H NMR (CD$_3$OD): δ 1.46 (s, 3H), 2.92 (dd, J=13.6 Hz, 2H), 5.07 (s, 2H), 6.56 (dd, J=8.0 Hz, J=2 Hz, 1H), 6.71 (d, J=2 Hz, 1H), 6.70 (d, J=8 Hz, 1H), 7.15 (d, J=8 Hz, 2H), 7.26 (t, J=8 Hz, 1H), 7.40 (t, J=8 Hz, 2H). MS (ESI) m/z 361.2 (M+H$^+$).

Example 75

[(2'-Methylphenyl)oxycarbonyl]methyl (S)-3-(3,4-dihydroxyphenyl)-2-hydrazino-2-methylpropanoate (212)

The title compound was prepared as a white solid using 2'-methylphenyl 2-bromoacetate according to the general procedure. $^1$H NMR (CD$_3$OD): δ 1.50 (s, 3H), 2.20 (s, 3H), 2.92 (dd, J=13.6 Hz, 2H), 5.12 (s, 2H), 6.55 (dd, J=8.0 Hz, J=2 Hz, 1H), 6.66 (d, J=2 Hz, 1H), 6.68 (d, J=8 Hz, 1H), 7.05 (d, J=8 Hz, 1H), 7.20 (m, 2H), 7.27 (d, J=8 Hz, 1H). MS (ESI) m/z 375.2 (M+H$^+$).

Example 76

[(2,6-Dimethylphenyl)oxycarbonyl]methyl (S)-3-(3,4-dihydroxyphenyl)-2-hydrazino-2-methylpropanoate (213)

The title compound was prepared as a white solid using 2',6'-dimethylphenyl 2-bromoacetate according to the general procedure. $^1$H NMR (CD$_3$OD): δ 1.50 (s, 3H), 2.17 (s, 6H), 3.00 (dd, J=13.6 Hz, 2H), 5.17 (s, 2H), 6.56 (dd, J=8.0 Hz, J=2 Hz, 1H), 6.66 (d, J=2 Hz, 1H), 6.68 (d, J=8 Hz, 1H), 7.07 (m, 3H). MS (ESI) m/z 389.2 (M+H$^+$).

Example 77

[Benzyloxycarbonyl]methyl (S)-3-(3,4-dihydroxyphenyl)-2-hydrazino-2-methylpropanoate (214)

The title compound was prepared as a white solid using phenylmethyl 2-bromoacetate according to the general procedure. $^1$H NMR (DMSO-d$_6$): δ 1.18 (s, 3H), 2.74 (dd, J=13.6 Hz, 2H), 4.81 (s, 2H), 5.17 (s, 2H), 6.39 (dd, J=8.0 Hz, J=2 Hz, 1H), 6.52 (d, J=2 Hz, 1H), 6.57 (d, J=8 Hz, 1H), 7.36 (m, 5H). MS (ESI) m/z 375.2 (M+H$^+$).

Example 78

2-Oxo-2-phenylethyl (S)-3-(3,4-dihydroxyphenyl)-2-hydrazino-2-methylpropanoate (215)

The title compound was prepared as a white solid using 2-bromo-1-phenylethan-1-one according to the general procedure. $^1$H NMR (CD$_3$OD): δ 1.52 (s, 3H), 3.04 (dd, J=13.6 Hz, 2H), 5.65 (dd, J=12 Hz, 2H), 6.57 (dd, J=8.0 Hz, J=2 Hz, 1H), 6.67 (d, J=2 Hz, 1H), 6.71 (d, J=8 Hz, 1H), 7.71 (t, J=8.8 Hz, 2H), 7.69 (t, J=8.8 Hz, 1H), 8.01 (D, J=8.8 Hz, 2H). MS (ESI) m/z 345.2 (M+H$^+$).

Example 79

(Methoxycarbonyl)methyl (S)-3-(3,4-dihydroxyphenyl)-2-hydrazino-2-methylpropanoate (216)

The title compound was prepared as a white solid using methyl 2-bromoacetate according to the general procedure. $^1$H NMR (CD$_3$OD): δ 1.48 (s, 3H), 2.98 (dd, J=13.6 Hz, 2H), 3.80 (s, 3H), 4.82 (s, 2H), 6.53 (dd, J=8.0 Hz, J=2 Hz, 1H), 6.63 (d, J=2 Hz, 1H), 6.69 (d, J=8 Hz, 1H). MS (ESI) m/z 299.1 (M+H$^+$).

Example 80

(t-Butoxycarbonyl)methyl (S)-3-(3,4-dihydroxyphenyl)-2-hydrazino-2-methylpropanoate (217)

The title compound was prepared as a white solid using t-butyl 2-bromoacetate according to the general procedure. $^1$H NMR (CD$_3$OD): δ 1.47 (s, 3H), 1.51 (s, 9H), 2.98 (dd, J=13.6 Hz, 2H), 4.70 (s, 2H), 6.53 (dd, J=8.0 Hz, J=2 Hz, 1H), 6.62 (d, J=2 Hz, 1H), 6.69 (d, J=8 Hz, 1H). MS (ESI) m/z 341.2 (M+H$^+$).

Example 81

(1S)-(Methoxycarbonyl)ethyl (S)-3-(3,4-dihydroxyphenyl)-2-hydrazino-2-methylpropanoate (218)

The title compound was prepared as a white solid using methyl (2S)-2-bromopropanoate according to the general procedure. $^1$H NMR (CD$_3$OD): δ 1.38 (s, 3H), 1.50 (d, J=7.2 Hz, 3H), 2.88 (m, J=13.6 Hz, 2H), 3.80 (s, 3H), 5.26 (q, J=7.2 Hz, 1H), 6.50 (dd, J=8.0 Hz, J=2 Hz, 1H), 6.60 (d, J=2 Hz, 1H), 6.68 (d, J=8 Hz, 1H). MS (ESI) m/z 313.2 (M+H$^+$).

Example 82

(1R)-(Methoxycarbonyl)ethyl (S)-3-(3,4-dihydroxyphenyl)-2-hydrazino-2-methylpropanoate (219)

The title compound was prepared as a white solid using methyl (2R)-2-bromopropanoate according to the general procedure. $^1$H NMR (CD$_3$OD): δ 1.43 (s, 3H), 1.49 (d, J=7.2 Hz, 3H), 2.89 (dd, J=13.6 Hz, 2H), 3.76 (s, 3H), 5.26 (q, J=7.2 Hz, 1H), 6.49 (dd, J=8.0 Hz, J=2 Hz, 1H), 6.59 (d, J=2 Hz, 1H), 6.68 (d, J=8 Hz, 1H). MS (ESI) m/z 313.3 (M+H$^+$).

Example 83

2-Acetyloxyethyl (S)-3-(3,4-dihydroxyphenyl)-2-hydrazino-2-methylpropanoate (220)

The title compound was prepared as a white solid using 2-bromoethyl acetate according to the general procedure. MS (ESI) m/z 313.2 (M+H$^+$).

Example 84

2-Phenylethyl (S)-3-(3,4-dihydroxyphenyl)-2-hydrazino-2-methylpropanoate (221)

The title compound was prepared as a white solid using (2-bromoethyl)benzene according to the general procedure. $^1$H NMR (CD$_3$OD): δ 1.39 (s, 3H), 2.84 (dd, J=13.6 Hz, 2H), 2.95 (t, J=7.2 Hz, 2H), 4.36 (m, 2H), 6.31 (d, J=7.6 Hz, 1H), 6.53 (s, 1H), 6.65 (d, J=8.4 Hz, 1H), 7.20 (m, 3H), 7.29 (m, 2H). MS (ESI) m/z 331.2 (M+H$^+$).

Example 85

3-Phenylpropyl (S)-3-(3,4-dihydroxyphenyl)-2-hydrazino-2-methylpropanoate (222)

The title compound was prepared as a white solid using (3-bromopropyl)benzene according to the general procedure. $^1$H NMR (CD$_3$OD): δ 1.46 (s, 3H), 1.97 (q, J=7.6 Hz, 2H), 2.65 (t, J=6.0 Hz, 2H), 2.90 (dd, J=13.6 Hz, 2H), 4.17 (m, 2H), 6.45 (d, J=8.4 Hz, 1H), 6.58 (s, 1H), 6.68 (d, J=8.0 Hz, 1H), 7.17 (m, 3H), 7.26 (m, 2H). MS (ESI) m/z 345.2 (M+H$^+$).

Example 86

3-Phenoxypropyl (S)-3-(3,4-dihydroxyphenyl)-2-hydrazino-2-methylpropanoate (223)

The title compound was prepared as a white solid using 3-bromo-1-phenoxypropane according to the general procedure. $^1$H NMR (CD$_3$OD): δ 1.46 (s, 3H), 2.12 (q, J=2.0 Hz, 2H), 2.91 (dd, J=13.6 Hz, 2H), 3.96 (m, 2H), 4.36 (m, 2H), 6.45 (d, J=7.6 Hz, 1H), 6.58 (s, 1H), 6.67 (d, J=7.6 Hz, 1H), 6.90 (m, 3H), 7.25 (m, 2H). MS (ESI) m/z 361.2 (M+H$^+$).

Example 87

2-Morpholin-4-ylethyl (S)-3-(3,4-dihydroxyphenyl)-2-hydrazino-2-methylpropanoate (224)

The title compound was prepared as a white solid using 4-(2-bromoethyl)morpholine according to the general procedure. ¹H NMR (CD₃OD): δ 1.53 (s, 3H), 2.91 (dd, J=13.6 Hz, 2H), 3.08 (m, 4H), 3.43 (m, 2H), 3.92 (m, 4H), 4.42 (m, 2H,), 6.50 (d, J=7.6 Hz, 1H), 6.59 (s, 1H), 6.72 (d, J=7.6 Hz, 1H). MS (ESI) m/z 340.2 (M+H⁺).

Example 88

Cyclohexyl (S)-3-(3,4-dihydroxyphenyl)-2-hydrazino-2-methylpropanoate (226)

Acetyl chloride (1 mL) was slowly added to cyclohexanol (5 mL) at 0° C. After stirring at 0° C. for 10 min, carbidopa (294 mg, 1.5 mmol) was added slowly as solid. The resulting mixture was warmed to 50° C. for 16 h. After cooling to room temperature, ethyl acetate (40 mL) was added and product was extracted with water (4×5 mL), then the aqueous phase was lyophilized to give the crude product. HPLC of the crude product afforded 50 mg of the title compound as an oil. ¹H NMR (CD₃OD): δ 1.46 (s, 3H), 1.52–1.80 (m, 10H), 2.92 (dd, J=13.6 Hz, 2H,), 4.85 (m, 1H), 6.49 (d, J=7.6 Hz, 1H), 6.59 (s, 1H), 6.68 (d, J=7.6 Hz, 1H). MS (ESI) m/z 309.3 (M+H⁺).

Example 89

Phenyl (S)-3-(3,4-dihydroxyphenyl)-2-hydrazino-2-methylpropanoate (227)

A mixture of Boc-carbidopa (296 mg, 1 mmol) and N,N'-carbonyldiimimidazole (356 mg, 2.2 mmol) in anhydrous tetrahydrofuran (THF) (20 mL) was stirred at room temperature for 6 h. Then, to the mixture was added phenol (1.2 mmol) followed by addition of a catalytic amount of 4-dimethylaminopyridine (DMAP). The resulting mixture was stirred at 50° C. for 16 h. After concentration, the residue was dissolved in ethyl acetate, and washed with cold 5% aqueous NaHCO₃ and then 10% citric acid. The organic phase was separated and dried over Na₂SO₄ After filtration, the solvent was removed under reduced pressure. The resulting residue was purified by chromatography (SiO2, 50:50 ethyl acetate/hexane) to provide Boc-protected carbidopa ester (yield: 20% to 25%). The Boc group was removed with 30% trifluoroacetic acid/dichloromethane at room temperature for 30 min. After concentration, HPLC (0.05% trifluoroacetic acid/water/acetonitrile) followed by lyophilization afforded 90 mg of the title compound. ¹H NMR (CD₃OD): δ 1.61 (s, 3H), 3.04 (dd, J=13.6 Hz, 2H), 6.59 (d, J=8.0 Hz, 1H), 6.70 (s, 1H), 6.73 (d, J=8.4 Hz, 1H), 7.09 (d, J=8 Hz), 7.26 (t, J=8 Hz), 7.40 (t, J=8 Hz). MS (ESI) m/z 303.2 (M+H⁺).

Example 90

4-Methylthiophenyl (S)-3-(3,4-dihydroxyphenyl)-2-hydrazino-2-methylpropanoate (228)

The title compound was prepared as a solid following the procedure outlined in Example 98 but substituting 4-methylthiophenol for phenol. ¹H NMR (CD₃OD): δ 1.43 (s, 3H), 2.49 (s, 3H) 3.13 (dd, J=13.6 Hz, 2H), 6.58 (d, J=8.0 Hz, 1H), 6.69 (s, 1H), 6.73 (d, J=8.4 Hz, 1H), 7.03 (d, J=8 Hz), 7.30 (d, J=8 Hz). MS (ESI) m/z 349.1 (M+H⁺).

Example 91

(S)-3-(3,4-Dihydroxyphenyl)-2-hydrazino-2-methylpropionic acid carboxymethylester (229)

Step A: tert-Butyl (S)-α-[3-(3,4-dihydroxyphenyl)-2-(N'-tert-butoxycarbonyl-hydrazino)-2-methylpropionyloxy]-acetate (230)

To a stirred solution of 102 (650 mg, 2 mmol) in anhydrous N,N-dimethylformamide (7 mL) in a 50 mL capacity screwcap-septum vial was added cesium hydrogencarbonate (480 mg, 2.5 mmol). After having stirred at room temperature for 30 min, a solution of tert-butyl α-bromoacetate (2.5 mmol) was introduced into the reaction mixture. The resulting mixture was stirred at room temperature for 3 h and then, at 45° C. overnight (~12 h). The reaction mixture was cooled to room temperature and filtered. The residue was washed with ethyl acetate (25 mL×4). The combined filtrates were washed with water (25 mL×2), dried over anhydrous sodium sulfate and concentrated. The residue was chromatographed over silica gel using a gradient of 10–100% ethyl acetate and hexane to afford 710 mg (81%) of the title compound as a light yellow thick liquid. MS (ESI) m/z 463.16 (M+Na⁺) and 439.02 (M–H⁻).

Step B: (S)-3-(3,4-Dihydroxyphenyl)-2-hydrazino-2-methylpropionic acid carboxymethylester (229)

A solution of compound 230 (441 mg, 1 mmol) in 1:1 (v/v) dichloromethane and trifluoroacetic acid was stirred at room temperature for 8 h (monitored by LC/MS). After removing the solvent under reduced pressure at room temperature, the residue was purified by preparative LC/MS technique to afford 165 mg (58%) of the title compound as a light yellow solid. ¹H NMR (400 MHz, CD₃OD): δ1.39 (3H, s), 2.93 (2H, m), 4.56 (1H, d), 4.75 (1H, d), 6.50 (1H, dd), 6.60 (1H, d), 6.67 (1H, d). MS (ESI) m/z 285.26 (M+H⁺) and 283.13 (M–H⁻).

Example 92

(S)-4-[3-(3,4-Dihydroxyphenyl)-2-hydrazino-2-methylpropionyloxy]-butyric acid (231)

Following the procedure described for preparation of compound 229, and substituting tert-butyl bromomethyl acetate with 2,4-dimethoxybenzyl γ-bromobutyrate, provided the title compound (41% over 2 steps) as a colorless thick liquid. ¹H NMR (400 MHz, CD₃OD): δ1.45 (3H, s), 1.95 (2H, q), 2.35 (2H, t), 2.86(2H, m), 4.21 (2H, m), 6.46 (1H, dd), 6.56(1H, d), 6.68 (1H, d). MS (ESI) m/z 313.21 (M+H⁺) and 311.18 (M–H⁻).

Example 93

(S)-6-[3-(3,4-Dihydroxyphenyl)-2-hydrazino-2-methylpropionyl]-oxy-hexanoic acid (232)

Following the procedure described for preparation of compound 229, and substituting tert-butyl bromomethyl acetate with 4-methoxybenzyl 6-bromohexanoate, provided the title compound (20% over 2 steps) as a colorless thick liquid. ¹H NMR (400 MHz, DMSO-d₆): δ1.28 (3H, s), 1.50 (4H, m), 1.99 (2H, broad s), 2.17 (2H, t), 4.03 (2H, m), 6.33 (1H, dd), 6.47(1H, d), 6.60 (1H, d). MS (ESI) m/z 341.26 (M+H⁺) and 339.21 (M–H⁻).

Example 94

(S)-3-[3-(3,4-Dihydroxyphenyl)-2-hydrazino-2-methylpropionyloxy]methylbenzoic acid (233)

Following the procedure described for preparation of compound 229, and substituting tert-butyl bromomethyl acetate with 2,4-dimethoxybenzyl m-chloromethyl-benzoate, provided the title compound (26% over 2 steps) as a white solid. $^1$H NMR (400 MHz, CD$_3$OD): δ1.42 (3H, s), 2.79 (1H, d), 2.90 (1H, d), 5.2 (2H, m), 6.35 (1H, dd), 6.56 (1H, d); 6.60 (1H, d), 7.45 (2H, m), 7.97 (2H, m). MS (ESI) m/z 361.15 (M+H$^+$) and 359.17 (M–H$^-$).

Example 95

(S)-3-(3,4-Dihydroxyphenyl)-2-hydrazino-2-methylpropionic acid 4-carboxymethyl-benzyl ester (234)

Following the procedure described for preparation of compound 229, and substituting tert-butyl bromomethyl acetate with 2,4-dimethoxybenzyl p-bromomethyl-benzoate, provided the title compound (25% over 2 steps) as a white solid. $^1$H NMR (400 MHz, CD$_3$OD): δ1.40 (3H, s), 2.85 (2H, m), 3.30 (2H, m), 3.58 (2H, d), 5.11 (1H, d), 6.31 (1H, m), 6.58 (2H, m), 7.27 (4H, m). MS (ESI) m/z 375.17 (M+H$^+$) and 373.13 (M–H$^-$).

Example 96

1(R)- and 1(S)-Methyl-2-Phenylethyl (S)-3-(3,4-dihydroxyphenyl)-2-hydrazino-2-methylpropionates (237)

Following the procedure described for preparation of compound 229, and substituting tert-butyl bromomethyl acetate with 2-phenylisopropyl bromide, provided the colorless thick liquid title compound as a mixture of two diastereoisomers. $^1$HNMR (CD$_3$OD): δ 1.24–1.22 (3H, m), 1.31 (3H, s), 2.87–2.60 (4H, m), 5.14–5.05 (1H, m), 6.37–6.12 (1H, m), 6.53–6.46 (1H, m), 6.63–6.55 (1H, m), 7.27–7.14 (5H, m). MS (ESI) m/z 345.26 (M+H$^+$).

Example 97

Cinnamyl (S)-3-(3,4-Dihydroxyphenyl)-2-hydrazino-2-methylpropionate (238)

Step A: N-Fmoc Carbidopa (239)

To a stirred solution of carbidopa (5.0 g, 22.12 mmol) in dry methanol was added 9-fluorenylmethyloxycarbonyl chloride (Fmoc-chloride) (6.3 g, 24.3 mmol) and triethylamine (3.5 mL, 25 mmol) at 0° C. The resulting mixture was stirred at room temperature overnight. The reaction mixture was diluted with water (200 mL) and extracted with ethyl acetate (2×200 mL). The combined extracts were washed with brine (100 mL), dried over magnesium sulfate and evaporated to give 10 g of crude title compound as a light brown liquid, which was used in the next step without further purification. MS (ESI) m/z 449.26 (M+H$^+$).

Step B: Cinnamyl (S)-3-(3,4-Dihydroxyphenyl)-2-hydrazino-2-methylpropionate (238)

To a stirred suspension of compound 239 (0.9 g, 2.0 mmol) and cesium hydrogen carbonate (0.39 g, 2 mmol) in anhydrous N,N-dimethylformamide (15 mL) was added cinnamyl bromide (0.12 mL, 1.1 mmol) and then, the reaction mixture was stirred at room temperature overnight (monitored by LC/MS). The reaction mixture was cooled to room temperature and filtered. The residue was washed with ethyl acetate (25 mL×4). The combined filtrates were washed with water (25 mL×2), dried over magnesium sulfate and evaporated the solvent. The residue was purified by flash chromatography using 1:1 (v/v) ethyl acetate/hexane as eluent to afford the crude cinnamyl ester derivative of N-Fmoc carbidopa as a yellow thick liquid, which was then dissolved in dry tetrahydrofuran (10 mL). To this solution was added a catalytic amount of DBU (0.2 mL) followed by 1-octanethiol (2 mL). The resulting mixture was stirred at room temperature for 15 min (monitored by LC/MS). Upon completion of the reaction, the reaction mixture was washed with diethyl ether (2×0 mL) and the residue was purified by preparative LC/MS technique. The title compound (15%) was isolated as a colorless thick liquid. $^1$HNMR (CD$_3$OD): δ 1.39 (3H, s), 2.80 (2H, m), 4.74 (2H, dd), 6.27 (1H, m), 6.43 (1H, m), 6.67–6.56 (3H, m), 7.42–7.21 (5H, m). MS (ESI) m/z 343.04 (M+M$^+$).

Example 98

1(R)- and 1(S)-Phenylethyl (S)-3-(3,4-dihydroxyphenyl)-2-hydrazino-2-methylpropionates (240)

Following the procedure described for preparation of compound 228, and substituting cinnamyl bromide with 1-bromo-1-phenylethane, provided the colorless thick liquid title compound (10%) as a mixture of two diastereoisomers. $_1$HNMR (CD$_3$OD): δ 1.36 (3H, broad s), 1.51 (3H, broad s), 2.69–2.88 (2H, m), 5.81–5.89 (1H, m), 6.39 (1H, m), 6.49–6.57 (1H, m), 6.60 (1H, m), 7.34–7.26 (5H, m). MS (ESI) m/z 331.25 (M+H$^+$).

Example 99

2-Methylbenzoic acid (S)-4-(2-hydrazino-2-methoxycarbonyl-propyl)-2-hydroxy-phenyl ester (241)
and 2-Methylbenzoic acid (S)-5-(2-hydrazino-2-methoxycarbonyl-propyl)-2-hydroxy-phenyl ester (242)

Following the procedure for preparation of compounds 125 and 126, and substituting 2,6-dimethyl-benzoyl chloride with 2-methyl-benzoyl chloride and carbidopa with carbidopa methyl ester, provided the title compounds 241 and 242 as a mixture of two inseparable regioisomers. $^1$H NMR (CD$_3$OD): δ1.42 (s, 1.5H), 1.46 (s, 1.5H), 2.60 (bs, 3H), 2.90–3.05 (m, 2H), 3.76 (s, 1.5H), 3.80 (s, 1.5H), 6.66 (dd, 1H), 6.76 (d, 1H), 7.04 (d, 1H), 7.32 (m, 2H), 7.50 (m, 1H), 8.12 (d, 1H).

Example 100

4-Pyridylmethyl (S)-3-(3,4-diethylcarbonyloxyphenyl)-2-hydrazino-2-methylpropanoate (243)

Following the procedure for preparation of compounds 210 in Example 73, and substituting N-Boc protected (4-chlorophenoxy)methyl (2S)-3-(3,4-dihydroxyphenyl)-2-hydrazino-2-methylpropanoate with N-Boc protected 4-pyridylmethyl (2S)-3-(3,4-dihydroxyphenyl)-2-hydrazino-2-methylpropanoate, provided the title compound. $_1$H NMR (CD$_3$OD): δ1.34 (t, J=7.2 Hz, 3H), 1.35 (t, J=7.2 Hz, 3H), 1.61 (s, 3H), 3.13 (s, 2H), 4.29 (q, J=7.2 Hz, 2H), 4.30 (q, J=7.2 Hz, 2H), 5.43 (s, 2H), 7.18 (d, J=2 Hz, 1H), 7.19 (s, 1H), 7.21 (d, J=2 Hz, 1H), 7.72 (d, J=6 Hz, 1H), 8.75 (d, J=6 Hz, 1H), 8.73 (s, 1H), 8.82 (d, J=6 Hz, 1H). MS (ESI) m/z 462.17 (M+H+).

Example 101

Uptake of L-Dopa Following Administration of L-Dopa and Carbidopa-Dopa Prodrugs in Rats Sustained release oral dosage forms, which release drug slowly over periods of 6–24 hours, generally release a significant proportion of the dose within the colon. Thus drugs suitable for use in such dosage forms can exhibit good colonic absorption. This experiment was conducted to assess the uptake and resultant blood levels of L-dopa, coadministered (intracolonically or intraperitoneally) with a carbidopa prodrug, for assessing suitability for use in an oral sustained release dosage form. Bioavailability of L-dopa was calculated relative to oral coadministration of L-dopa and carbidopa. Relative bioavailability of L-dopa is $F_{rel}$ in Table 1 and is expressed as a percent of the L-dopa bioavailability of orally administered L-dopa, coadministered with carbidopa.

Step A: Administration Protocol

Rats were obtained commercially and were pre-cannulated in the both the ascending colon and the jugular vein. Animals were conscious at the time of the experiment. All animals were fasted overnight and until 4 hours post-dosing of L-Dopa. Carbidopa or carbidopa prodrug was administered as a solution in water or citrate buffer either orally, or intraperitoneally or intracolonically at a dose equivalent to 25 mg of carbidopa per kg. Either at the same time or 1 hour after carbidopa dosing, L-dopa HCl salt was administered as a solution (in water) directly into the colon via the cannula at a dose equivalent to 75 mg of L-Dopa per kg. Blood samples (0.3 mL) were obtained from the jugular cannula at intervals over 8 hours and were quenched immediately by addition of sodium metabisulfite to prevent oxidation of L-Dopa. Blood was then further quenched with methanol/perchloric acid to prevent hydrolysis of the prodrug. Blood samples were analyzed as described below.

Step B: Sample Preparation for Colonic Absorbed Drug

1. In blank 1.5 mL tubes, 300 µL of methanol/perchloric acid was added.
2. Rat blood 300 µL was collected at different time points into EDTA tubes containing 75 µL of sodium metabisulfite, and vortexed to mix. A fixed volume of blood (100 µL) was immediately added into the eppendorf tube and vortexed to mix.
3. Ten microliters of an L-dopa standard stock solution (0.04, 0.2, 1, 5, 25, 100 µg/mL) and 10 µL of the 10% sodium metabisulfate was added to 80 µL of blank rat blood to make up a final calibration standard (0.004, 0.02, 0.1, 0.5, 2.5, 10 µg/mL). Then 300 µL of 50/50 methanol/perchloric acid was added into each tube followed by 20 µL of p-chlorophenylalanine.
4. Samples were vortexed and centrifuged at 14,000 rpm for 10 min.
5. Supernatant was analyzed by LC/MS/MS.

Step C: LC/MS/MS Analysis

An API 40000 LC/MS/MS spectrometer equipped with Agilent 1100 binary pumps and a CTC HTS-PAL autosampler were used in the analysis. A Zorbax XDB C8 4.6×150 mm column was used during the analysis. The mobile phase was 0.1% formic acid (A) and acetonitrile with 0.1% formic acid (B). The gradient condition was: 5% B for 0.5 min, then to 98% B in 3 min, then maintained at 98% B for 2.5 min. The mobile phase was returned to 2% B for 2 min. A TurboIonSpray source was used on the API4000. The analysis was done in positive ion mode and the MRM transition for each analyte was optimized using standard solution. 5 µL of the samples were injected. Non-compartmental analysis was performed using WinNonlin (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2,z}$ (terminal half-life). Maximum concentrations of L-dopa in the blood (Cmax values) and the area under blood concentration versus time curve (AUC) values after intracolonic dosing of L-dopa with carbidopa prodrugs were significantly higher (>2-fold) than those produced from colonic administration of L-dopa with carbidopa.

As shown in Table 1, intracolonic coadministration of L-dopa and carbidopa results in very low relative bioavailability of L-dopa (i.e., only 2.4% of orally coadministered L-dopa and carbidopa). By comparison, coadministration of all of the carbidopa prodrugs tabulated in Table 2 with L-dopa (except the mixture of compounds 125 and 126) exhibited improved relative bioavailability of L-dopa. Carbidopa prodrug compounds 109, 160 and 177 all exhibited at least 10-fold higher relative bioavailability of L-dopa, and compounds 101, 105, 162, 163, 167, 168, 173, 175, 177, and 208 all exhibited at least 5-fold higher relative bioavailability of L-dopa. These data demonstrate that certain compounds can be formulated as compositions suitable for effective sustained oral release and uptake from the colon.

TABLE 1

L-Dopa Bioavailabilities in Rats

| Carbidopa Prodrug Compound #/ Example # | L-Dopa Compound | L-Dopa Dose (mg-eq L-dopa/kg) | Vehicle | Carbidopa Prodrug Route and Dose (mg-eq carbidopa/kg) | Number of Rats | Average Relative Bioavailability of L-Dopa $F_{rel}$ (%) |
|---|---|---|---|---|---|---|
| N/A (comparative) | L-Dopa HCl Salt | 75 | Water | Carbidopa HCl Salt Intracolonic (25) | 6 | 2.4 |

TABLE 1-continued

L-Dopa Bioavailabilities in Rats

| Carbidopa Prodrug Compound #/ Example # | L-Dopa Compound | L-Dopa Dose (mg-eq L-dopa/ kg) | Vehicle | Carbidopa Prodrug Route and Dose (mg-eq carbidopa/kg) | Number of Rats | Average Relative Bioavailability of L-Dopa $F_{rel}$ (%) |
|---|---|---|---|---|---|---|
| N/A (comparative) | L-Dopa HCl Salt | 75 | Water | Carbidopa HCl Salt Oral bolus (25) | 6 | 100 |

TABLE 2

Carbidopa Prodrug Administration Schedule

| Carbidopa Prodrug Compound # | L-Dopa Compound | L-Dopa Dose (mg-eq L-dopa/ kg) | Vehicle | Carbidopa Prodrug Route and Dose (mg-eq carbidopa/kg) | Number of Rats |
|---|---|---|---|---|---|
| Compounds 241 and 242 (50:50 mix) | L-Dopa | 75 | Citrate Buffer | Intracolonic (25) | 3 |
| Compounds 125 and 126 (50:50 mix) | L-Dopa | 75 | Citrate Buffer | Intracolonic (25) | 3 |
| Compounds 127 and 128 (50:50 mix) | L-Dopa | 75 | Citrate Buffer | Intracolonic (25) | 3 |
| Compound 110 | L-Dopa HCl Salt | 75 | Water | Intracolonic (25) | 3 |
| Compound 109 | L-Dopa HCl Salt | 75 | Water | Intracolonic (50) | 3 |
| Compound 105 | L-Dopa TFA Salt | 75 | Water | Intracolonic (25) | 3 |
| Compound 101 | L-Dopa HCl Salt | 75 | Water | Intracolonic (25) | 6 |
| Compound 163 | L-Dopa HCl Salt | 75 | Water | Intracolonic (25) | 8 |
| Compound 161 | L-Dopa HCl Salt | 75 | Water | Intracolonic (25) | 6 |
| Compound 160 | L-Dopa HCl Salt | 75 | Water | Intracolonic (25) | 6 |
| Compound 162 | L-Dopa HCl Salt | 75 | Water | Intracolonic (25) | 5 |
| Compound 177 | L-Dopa HCl Salt | 75 | Water | Intracolonic (25) | 7 |
| Compound 168 | L-Dopa HCl Salt | 75 | Water | Intracolonic (25) | 6 |
| Compound 167 | L-Dopa HCl Salt | 75 | Water | Intracolonic (25) | 5 |
| Compound 175 | L-Dopa HCl Salt | 75 | Water | Intracolonic (25) | 5 |
| Compound 173 | L-Dopa HCl Salt | 75 | Water | Intracolonic (25) | 5 |
| Compound 174 | L-Dopa HCl Salt | 75 | Water | Intracolonic (25) | 7 |
| Compound 227 | L-Dopa HCl Salt | 75 | Water | Intracolonic (25) | 6 |
| Compound 164 | L-Dopa HCl Salt | 75 | Water | Intracolonic (25) | 7 |
| Compound 243 | L-Dopa HCl Salt | 75 | Water | Intracolonic (25) | 6 |
| Compound 208 | L-Dopa HCl Salt | 75 | Water | Intracolonic (25) | 6 |
| Compound 183 | L-Dopa HCl Salt | 75 | Water | Intracolonic HCl Salt (25) | 5 |

What is claimed is:

1. A compound of Formula (I):

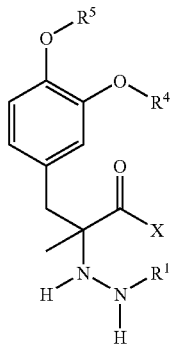
(I)

a stereoisomer thereof, an enantiomer thereof, a pharmaceutically acceptable salt thereof, a hydrate thereof, or a solvate of any of the foregoing, wherein:

X is a moiety of Formula (II):

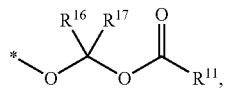
(II)

where:

$R^1$ is selected from hydrogen and a moiety comprising Formula (IX):

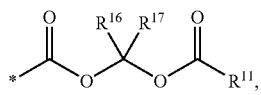
(IX)

$R^4$ and $R^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, cycloheteroalkyl, substituted cycloheteroalkyl, —C(O)OR$^{27}$, —C(O)R$^{27}$, —(CR$^{16}$R$^{17}$)OC(O)R$^{11}$ and moieties of Formulae (XVII) and (XVIII):

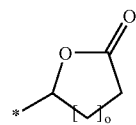
(XVII)

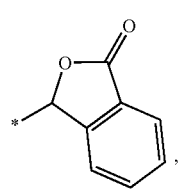
(XVIII)

wherein o is 1–3, and the cycloheteroalkyl rings in (XVII) and (XVIII) are optionally substituted with one or more groups selected from halo, CN, NO$_2$, OH, C$_{1-6}$ alkyl, and C$_{1-6}$ alkoxy;

or $R^4$ and $R^5$ together form a structure selected from Formulae (XII) to (XVI):

(XII)

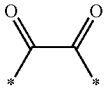
(XIII)

(XIV)

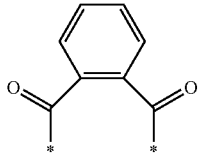
(XV)

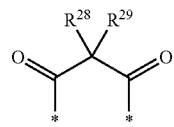
(XVI)

wherein the aryl ring in Formula (XV) is optionally substituted with one or more groups selected from halo, CN, OH, C$_{1-6}$ alkyl, C$_{1-6}$ alkoxy, and —CO$_2$R$^{31}$;

$R^{11}$ is selected from hydrogen, alkyl, substituted alkyl, alkoxy, substituted alkoxy, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl, or optionally, $R^{11}$ and either $R^{16}$ or $R^{17}$, together with the atoms to which $R^{11}$, and either $R^{16}$ or $R^{17}$ are attached, form a cycloheteroalkyl or substituted cycloheteroalkyl ring, optionally to which is fused an aryl, substituted aryl, heteroaryl, substituted heteroaryl, cycloalkyl, substituted cycloalkyl, cycloheteroalkyl or substituted cycloheteroalkyl ring;

$R^{16}$ and $R^{17}$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbomoyl, cycloalkyl, substituted cycloalkyl, cycloalkoxycarbonyl, substituted cycloalkoxycarbonyl, cycloheteroalkyl, substituted cycloheteroalkyl, heteroaryl, substituted heteroaryl, heteroarylalkyl, and substituted heteroarylalkyl or optionally, $R^{16}$ and $R^{17}$ together with the carbon atom to which $R^{16}$ and $R^{17}$ are attached form a cycloalkyl, substituted cycloalkyl, cycloheteroalkyl or substituted cycloheteroalkyl ring;

$R^{27}$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

with the proviso that none of $R^1$, $R^4$, $R^5$, $R^{11}$, $R^{16}$, $R^{17}$, $R^{27}$, $R^{28}$, $R^{29}$, and $R^{31}$ comprise a bile acid moiety.

2. A compound of Formula (Ib):

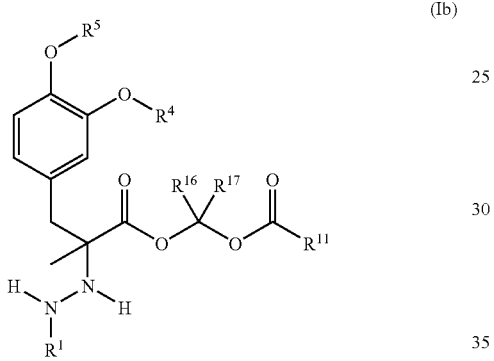

(Ib)

a stereoisomer thereof, an enantiomer thereof, a pharmaceutically acceptable salt thereof, a hydrate thereof, or a solvate of any of the foregoing, wherein:

$R^1$ is selected from hydrogen, and a moiety comprising Formula (IX):

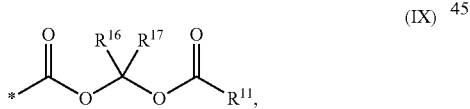

(IX)

$R^4$ and $R^5$ are independently selected from hydrogen, alkyl, substituted alkyl, aryl, substituted aryl, heteroalkyl, substituted heteroalkyl, arylalkyl, substituted arylalkyl, heteroaryl, substituted heteroaryl, heteroarylalkyl, substituted heteroarylalkyl, cycloalkyl, substituted cycloalkyl, cycloheteroalkyl, substituted cycloheteroalkyl, —C(O)OR$^{27}$, —C(O)R$^{27}$, —(CR$^{16}$R$^{17}$)OC(O)R$^{11}$ and moieties of Formulae (XVII) and (XVIII):

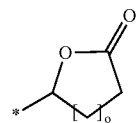

(XVII)

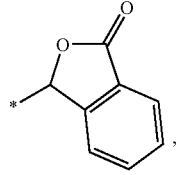

(XVIII)

wherein o is 1–3, and the cycloheteroalkyl rings in (XVII) and (XVIII) are optionally substituted with one or more groups selected from halo, CN, NO$_2$, OH, C$_{1-6}$ alkyl, and C$_{1-6}$ alkoxy;

or $R^4$ and $R^5$ together form a structure selected from Formulae (XII) to (XVI):

(XII)

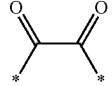

(XIII)

(XIV)

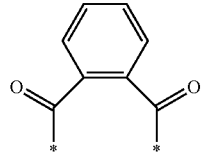

(XV)

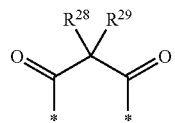

(XVI)

wherein the aryl ring in Formula (XV) is optionally substituted with one or more groups selected from halo, CN, OH, C$_{1-6}$ alkyl, C$_{1-6}$ alkoxy, and —CO$_2$R$^{31}$;

$R^{11}$ is selected from hydrogen, alkyl, substituted alkyl, alkoxy, substituted alkoxy, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl, or optionally, $R^{11}$ and either $R^{16}$ or $R^{17}$, together with the atoms to which $R^{11}$, $R^{16}$ and $R^{17}$ are attached, form a cycloheteroalkyl or substituted cycloheteroalkyl ring, to which an aryl, substituted aryl, heteroaryl, substituted heteroaryl, cycloalkyl, substituted cycloalkyl, cycloheteroalkyl or substituted cycloheteroalkyl ring is optionally fused to said cycloheteroalkyl or substituted cycloheteroalkyl ring;

$R^{16}$ and $R^{17}$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroarylalkyl, and substituted heteroarylalkyl or optionally, $R^{16}$ and $R^{17}$ together with the carbon atoms to which $R^{16}$ and $R^{17}$ are attached form a cycloalkyl, substituted cycloalkyl, cycloheteroalkyl or substituted cycloheteroalkyl ring;

$R^{27}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^{28}$ and $R^{29}$ are independently selected from hydrogen, alkyl, substituted alkyl, alkoxy, substituted alkoxy, alkoxycarbonyl, substituted alkoxycarbonyl, aryl, substituted aryl, cycloalkyl, substituted cycloalkyl, heteroalkyl, and substituted heteroalkyl; and $R^{31}$ is selected from hydrogen, alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl; with the proviso that none of $R^1$, $R^4$, $R^5$, $R^{11}$, $R^{16}$, $R^{17}$, $R^{27}$, $R^{28}$, $R^{29}$, and $R^{31}$ comprise a bile acid moiety.

3. A compound according to claim 2, wherein $R^4$ and $R^5$ are independently selected moieties from Formulae (XVII), and (XVIII).

4. A compound according to claim 2, wherein $R^1$ hydrogen.

5. A compound according to claim 2, wherein $R^1$ a moiety comprising Formula (IX).

6. A compound according to claim 2, wherein $R^4$ and $R^5$ are independently selected from hydrogen, alkanyl, substituted alkanyl, arylalkanyl, substituted arylalkanyl, heteroarylalkanyl, substituted heteroarylalkanyl, cycloalkanyl, substituted cycloalkanyl, cycloheteroalkanyl, and substituted cycloheteroalkanyl.

7. A compound according to claim 2, wherein $R^4$ and $R^5$ are independently selected from hydrogen, methyl, ethyl, propyl, isopropyl, butyl, isobutyl, sec-butyl, tert-butyl, cyclopentyl, cyclohexyl, benzyl, and pyridyl, where the aryl rings of the benzyl and pyridyl groups are optionally substituted with one or more substituents selected from halo, CN, $NO_2$, OH, $C_{1-6}$ alkyl, $C_{1-6}$ alkoxy and $-CO_2R^{31}$.

8. A compound according to claim 2, wherein $R^4$ and $R^5$ are independently selected from hydrogen, $-C(O)OR^{27}$, and $-C(O)R^{27}$.

9. A compound according to claim 8, wherein $R^{27}$ is selected from $C_{1-10}$ alkyl, substituted $C_{1-10}$ alkyl, $C_{5-8}$ aryl, $C^{5-8}$ substituted aryl, $C_{6-10}$ arylalkyl, and substituted $C_{6-10}$ arylalkyl.

10. A compound according to claim 2, wherein $R^4$ and $R^5$ are both independently $-C(O)OR^{27}$ or $-C(O)R^{27}$.

11. A compound according to claim 10, wherein $R^{27}$ is selected from $C_{1-10}$ alkyl, substituted $C_{1-10}$ alkyl, $C_{5-8}$ aryl, $C_{5-8}$ substituted aryl, $C_{6-10}$ arylalkyl, and substituted $C_{6-10}$ arylalkyl.

12. A compound according to claim 2, wherein $R^{27}$ is an alkyl selected from alkanyl, substituted alkanyl, cycloalkanyl, substituted cycloalkanyl, arylalkanyl, substituted arylalkanyl, heteroarylalkanyl, and substituted heteroarylalkanyl.

13. A compound according to claim 2, wherein $R^{27}$ is selected from methyl, ethyl, propyl, isopropyl, butyl, isobutyl, sec-butyl, tert-butyl, cyclopropyl, cyclobutyl, cyclopentyl, cyclohexyl and benzyl, where the aryl ring of the benzyl group is optionally substituted with one or more substituents selected from halo, CN, $NO_2$, OH, $C_{1-6}$ alkyl, $C_{1-6}$ alkoxy, and $-CO_2R^{31}$.

14. A compound according to claim 2, wherein $R^{27}$ is selected from aryl, substituted aryl, heteroaryl, and substituted heteroaryl.

15. A compound according to claim 2, wherein $R^{27}$ is selected from phenyl, pyridyl, furyl, and thienyl, the aromatic rings of which are optionally substituted with one or more substituents selected from halo, CN, $NO_2$, OH, $C_{1-6}$ alkyl, $C_{1-6}$ alkoxy, and $-CO_2R^{31}$.

16. A compound according to claim 2, wherein $R^4$ and $R^5$ are independently selected from hydrogen and $-(CR^{16}R^{17})OC(O)R^{11}$.

17. A compound according to claim 16, wherein $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy.

18. A compound according to claim 16, wherein $R^{16}$ and $R^{17}$ are independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

19. A compound according to claim 2, wherein $R^4$ and $R^5$ are both independently $-(CR^{16}R^{17})OC(O)R^{11}$.

20. A compound according to claim 19, wherein $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy.

21. A compound according to claim 19, wherein $R^{16}$ and $R^{17}$ are independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

22. A compound according to claim 2, wherein $R^{11}$ is an alkyl selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, cycloheteroalkanyl, substituted cycloheteroalkanyl, heteroarylalkanyl, and substituted heteroarylalkanyl.

23. A compound according to claim 2, wherein $R^{11}$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, and styryl, where the aryl ring of the styryl group is optionally substituted with one or more substituents are selected from halo, CN, $NO_2$, OH, $C_{1-6}$ alkyl, $C_{1-6}$ alkoxy, and $-CO_2R^{31}$.

24. A compound according to claim 2, wherein $R^{11}$ is selected from aryl, substituted aryl, heteroaryl, and substituted heteroaryl.

25. A compound according to claim 2, wherein $R^{11}$ is selected from phenyl, pyridyl, indolyl, furyl, imidazolyl, and oxazolyl, the aromatic rings of which are optionally substituted with one or more substituents selected from halo, CN, $NO_2$, OH, $C_{1-6}$ alkyl, $C_{1-6}$ alkoxy, and $-CO_2R^{31}$.

26. A compound according to claim 2, wherein $R^{11}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy.

27. A compound according to claim 2, wherein $R^{11}$ is selected from methoxy, ethoxy, propoxy, isopropoxy, butoxy, isobutoxy, sec-butoxy, tert-butoxy, pentyloxy, hexyloxy, cyclopropoxy, cyclobutoxy, cyclopentyloxy, cyclohexyloxy, 2,6-dimethylcyclohexyloxy, fenchyloxy, and adamantyloxy.

28. A compound according to claim 2, wherein $R^{11}$ and either $R^{16}$ or $R^{17}$, together with the atoms to which $R^{11}$ and either $R^{16}$ or $R^{17}$ are attached, form a cycloalkyl, substituted cycloalkyl, cycloheteroalkyl or substituted cycloheteroalkyl ring, to which an aryl, substituted aryl, heteroaryl or substituted heteroaryl ring is optionally fused to said cycloheteroalkyl or substituted cycloheteroalkyl ring.

29. A compound according to claim 2, wherein $R^1$ is hydrogen, $R^4$ and $R^5$ are each $C(O)OR^{27}$, $R^{16}$ is hydrogen, $R^{27}$ is ethyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and $C_{1-4}$ alkyl.

30. A compound according to claim 29, wherein $R^{17}$ is hydrogen.

31. A compound according to claim 29, wherein $R^{17}$ is methyl.

32. A compound according to claim 2, wherein $R^1$ is hydrogen, $R^4$ and $R^5$ are each $C(O)R^{27}$, $R^{16}$ is hydrogen, $R^{27}$ is isopropyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ selected from hydrogen, and $C_{1-4}$ alkyl.

33. A compound according to claim 32, wherein $R^{17}$ is hydrogen.

34. A compound according to claim 32, wherein $R^{17}$ is methyl.

35. A compound according to claim 2, wherein $R^1$ is hydrogen, $R^4$ and $R^5$ are each $C(O)R^{27}$, $R^{16}$ is hydrogen, $R^{27}$ is tert-butyl, $R^{11}$ is selected from $C_{1-4}$ alkyl, $C_{1-4}$ alkoxy, cyclohexyloxy, 2,6-dimethylcyclohexyloxy, fenchyloxy, and adamantyloxy, and $R^{17}$ is selected from hydrogen, and $C_{1-4}$ alkyl.

36. A compound according to claim 35, wherein $R^{17}$ is hydrogen.

37. A compound according to claim 35, wherein $R^{17}$ is methyl.

38. A compound according to claim 2, wherein $R^{16}$ and $R^{17}$ are independently selected from hydrogen, alkanyl, substituted alkanyl, cycloalkanyl, substituted cycloalkanyl, aryl, substituted aryl, heteroaryl, substituted heteroaryl, arylalkanyl, and substituted arylalkanyl.

39. A compound according to claim 2, wherein $R^{16}$ and $R^{17}$ are independently selected from hydrogen, methyl, ethyl, propyl, isopropyl, butyl, isobutyl, sec-butyl, tert-butyl, cyclopropyl, cyclobutyl, cyclopentyl, cyclohexyl, phenyl, and benzyl.

40. A compound according to claim 2, wherein $R^{16}$ is hydrogen and $R^{17}$ is selected from hydrogen, methyl, ethyl, propyl, isopropyl, butyl, isobutyl, sec-butyl, tert-butyl, cyclopropyl, cyclobutyl, cyclopentyl, cyclohexyl, phenyl, and benzyl.

41. A compound according to claim 2, wherein $R^{16}$ and $R^{17}$ together with the carbon atoms to which $R^{16}$ and $R^{17}$ are attached form a cycloalkanyl, substituted cycloalkanyl, cycloheteroalkanyl or substituted cycloheteroalkanyl ring.

42. A compound according to claim 2, wherein $R^{16}$ and $R^{17}$ together with the carbon atoms to which $R^{16}$ and $R^{17}$ are attached form a cyclopropyl, cyclobutyl, cyclopentyl or cyclohexyl ring.

43. A compound according to claim 2, wherein $R^{16}$ and $R^{17}$ are independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

44. A compound according to claim 2, wherein $R^{28}$ and $R^{29}$ are independently selected from hydrogen, alkanyl, aryl, and alkoxycarbonyl.

45. A compound according to claim 2, wherein $R^{28}$ and $R^{29}$ are independently selected from hydrogen, methyl, ethyl, propyl, butyl, phenyl, methoxycarbonyl, and ethoxycarbonyl.

46. A compound according to claim 2, wherein $R^{28}$ and $R^{29}$ are both hydrogen.

47. A compound according to claim 2, wherein $R^{31}$ is selected from hydrogen and $C_{1-8}$ alkyl.

48. A compound according to claim 2, wherein $R^{31}$ is selected from hydrogen, methyl, ethyl, propyl, isopropyl, butyl, isobutyl, sec-butyl, tert-butyl, cyclopropyl, cyclobutyl, cyclopentyl, and cyclohexyl.

49. A pharmaceutical composition comprising at least one pharmaceutically acceptable excipient, and a therapeutically effective amount of at least one compound according to any one of claims 1 or 48.

50. The pharmaceutical composition of claim 49, wherein the pharmaceutical composition further comprises at least one additional active agent.

51. The pharmaceutical composition of claim 50, wherein the at least one additional active agent is susceptible to decarboxylation, and the amount of the at least one compound is in an effective amount to inhibit decarboxylation of the at least one additional active agent.

52. The pharmaceutical composition of claim 50, wherein the at least one additional active agent is selected from levodopa and prodrugs of levodopa.

53. The pharmaceutical composition of claim 49, wherein the pharmaceutical composition is formulated for oral administration.

54. The pharmaceutical composition of claim 53, wherein the pharmaceutical composition is a sustained release formulation.

55. The pharmaceutical composition of claim 50, wherein the compound and the additional active agent comprise a single unit dosage form.

56. The pharmaceutical composition of claim 49, wherein the at least one compound is present in an amount effective for the treatment in a patient of a disease selected from Parkinson's disease, and hypertension.

57. A method of treating a Parkinson's disease in a patient, in need of such treatment, comprising administering to the patient a therapeutically effective amount of an active agent that is susceptible to decarboxylation, and at least one compound according to any of claims 1 or 2.

58. The method of claim 57, wherein the active agent is selected from levodopa and prodrugs of levodopa.

59. A method of treating hypertension in a patient in need of such treatment comprising administering to the patient a therapeutically effective amount of at least one compound according to any of claims 1 or 2.

60. A method of providing a therapeutically effective concentration of at least one active agent selected from levodopa and prodrugs of levodopa in the plasma of a patient, which active agent is susceptible to premature inactivation by decarboxylation, comprising co-administering to the patient the at least one active agent and the at least one compound according to any one of claims 1 or 2.

61. A method of inhibiting decarboxylation of at least one active agent selected from levodopa and prodrugs of levodopa in a patient, comprising administering to the patient at least one compound according to any one of claims 1 or 2.

62. The method of claim 61, wherein inhibiting decarboxylation comprises inhibiting a decarboxylase enzyme.

63. The compound of claim 1, wherein the compound is selected from:
(S)-3-(3,4-Dihydroxy)phenyl-2-hydrazino-2-methylpropionic acid (1R)-cyclohexyloxycaxbonyloxyethyl ester;
(S)-3-(3,4-Dihydroxy)phenyl-2-hydrazino-2-methylpropionic acid (1S)-cyclohexyloxycarbonyloxyethyl ester;

(S)-3-(3,4-Dihydroxyphenyl)-2-hydrazino-2-methyl-propionic acid acetoxymethyl ester;
(S)-3-(3,4-Dihydroxy-phenyl)-2-hydrazino-2-methyl-propionic acid 2,2-dimethyl-propionyloxymethyl ester;
(S)-3-(3,4-Bis-ethoxycarbonyloxy-phenyl)-2-hydrazino-2-methylpropionic acid 2,2-dimethyl-propionyloxymethyl ester;
(S)-3-(3,4-Dihydroxy-phenyl)-2-hydrazino-2-methyl-propionic acid 3-oxo-1,3-dihydro-isobenzofuran-1-yl ester;
(S)-3-(3,4-Bis-isobutyryloxy)phenyl-2-hydrazino-2-methylpropionic acid acetoxymethyl ester;
(S)-3-(3,4-Bis-isobutyryloxy)phenyl-2-hydrazino-2-methylpropionic acid 2,2-dimethyl-propionyloxymethyl ester;
(S)-3-(3,4-Bis-propionyloxy)phenyl-2-hydrazino-2-methylpropionic acid acetoxymethyl ester;
(S)-3-[3,4-Bis-(2,2-dimethylpropionyloxy)phenyl]-2-hydrazino-2-methylpropionic acid acetoxymethyl ester;
(S)-3-[3,4-Bis-(2,2-dimethylpropionyloxy)phenyl]-2-hydrazino-2-methylpropionic acid 2,2-dimethylpropionyloxymethyl ester;
(S)-3-(3,4-Bis-ethoxycarbonyloxy)phenyl-2-hydrazino-2-methylpropionic acid (1R)-isobutyryloxy-2-methylpropyl ester;
(S)-3-(3,4-Bis-ethoxycarbonyloxy)phenyl-2-hydrazino-2-methylpropionic acid (1S)-isobutyryloxy-2-methylpropyl ester;
(S)-3-(3,4-Bis-ethoxycarbonyloxy)phenyl-2-hydrazino-2-methylpropionic acid (1R)-acetoxy-2-methylpropyl ester;
(S)-3-(3,4-Bis-ethoxycarbonyloxy)phenyl-2-hydrazino-2-methylpropionic acid (1S)-acetoxy-2-methylpropyl ester;
(S)-3-(3,4-Bis-ethoxycarbonyloxy)phenyl-2-hydrazino-2-methylpropionic acid 1(R)-isobutyryloxyethyl ester;
(S)-3-(3,4-Bis-ethoxycarbonyloxy)phenyl-2-hydrazino-2-methylpropionic acid 1(S)-isobutyryloxyethyl ester;
(S)-3-(3,4-Bis-ethoxycarbonyloxy)phenyl-2-hydrazino-2-methylpropionic acid isobutyryloxymethyl ester;
(S)-3-(3,4-Dihydroxy)phenyl-2-hydrazino-2-methylpropionic acid 2-methylbenzoyloxymethyl ester;
(S)-3-(3,4-Dihydroxy)phenyl-2-hydrazino-2-methylpropionic acid 2,6-dimethylbenzoyloxymethyl ester;
(S)-3-(3,4-Dihydroxy)phenyl-2-hydrazino-2-methylpropionic acid ethoxycarbonyloxymethyl ester;
(S)-3-(3,4-Bis-ethoxycarbonyloxy)phenyl-2-hydrazino-2-methylpropionic acid ethoxycarbonyloxymethyl ester;
(S)-3-(3,4-Diacetoxy)phenyl-2-hydrazino-2-methylpropionic acid ethoxycarbonyloxymethyl ester;
(S)-3-(3,4-Bis-isobutyryloxy)phenyl-2-hydrazino-2-methylpropionic acid ethoxycarbonyloxymethyl ester;
(S)-3-(3,4-Bis-isobutyryloxy)phenyl-2-hydrazino-2-methylpropionic acid (1R)-ethoxycarbonyloxyethyl ester;
(S)-3-(3,4-Bis-isobutyryloxy)phenyl-2-hydrazino-2-methylpropionic acid (1S)-ethoxycarbonyloxyethyl ester;
(S)-3-(3,4-Bis-ethoxycarbonyl)oxyphenyl-2-hydrazino-2-methylpropionic acid (1R)-ethoxycarbonyloxyethyl ester;
(S)-3-(3,4-Bis-ethoxycarbonyl)oxyphenyl-2-hydrazino-2-methylpropionic acid (1S)-ethoxycarbonyloxyethyl ester;
(S)-3-(3,4-Dihydroxy)phenyl-2-hydrazino-2-methylpropionic acid (1R)-ethoxycarbonyloxyethyl ester;
(S)-3-(3,4-Dihydroxy)phenyl-2-hydrazino-2-methylpropionic acid (1S)-ethoxycarbonyloxyethyl ester;
(S)-3-(3,4-Dihydroxy)phenyl-2-hydrazino-2-methylpropionic acid (1R)-isopropoxycarbonyloxyethyl ester;
(S)-3-(3,4-Dihydroxy)phenyl-2-hydrazino-2-methylpropionic acid (1S)-isopropoxycarbonyloxyethyl ester;
(S)-3-(3,4-Bis-isobutyryloxy)phenyl-2-hydrazino-2-methylpropionic acid (1R)-isopropoxycarbonyloxyethyl ester;
(S)-3-(3,4-Bis-isobutyryloxy)phenyl-2-hydrazino-2-methylpropionic acid (1S)-isopropoxycarbonyloxyethyl ester;
(S)-3-(3,4-Dihydroxy)phenyl-2-hydrazino-2-methylpropionic acid (1R)-{[(1,3,3-trimethyl-bicyclo[2.2.1]hept-2-yloxy)carbonyl]oxy}ethyl ester; and
(S)-3-(3,4-Dihydroxy)phenyl-2-hydrazino-2-methylpropionic acid (1S)-{[(1,3,3-trimethyl-bicyclo[2.2.1]hept-2-yloxy)carbonyl]oxy}ethyl ester;
or pharmaceutically acceptable salts thereof, or solvates of any of the foregoing.

* * * * *

UNITED STATES PATENT AND TRADEMARK OFFICE
CERTIFICATE OF CORRECTION

PATENT NO. : 7,101,912 B2
APPLICATION NO. : 10/728942
DATED : September 5, 2006
INVENTOR(S) : Jia-Ning Xiang et al.

It is certified that error appears in the above-identified patent and that said Letters Patent is hereby corrected as shown below:

In claim 1, column 77, line 9, "$R^{31}$is" should read --$R^{31}$ is--.

In claim 2, column 79, line 17, "$R^{31}$is" should read --$R^{31}$ is--.

In claim 3, column 79, lines 25-26, "(XVII), and" should read --(XVII) and--.

In claim 4, column 79, lines 27-28, "$R^1$ hydrogen." should read --$R^1$ is hydrogen.--.

In claim 5, column 79, line 29, "$R^1$ a" should read --$R^1$ is a--.

In claim 9, column 79, line 49, "$C^{5-8}$" should read --$C_{5-8}$--.

In claim 23, column 80, line 36, "2,wherein" should read --2, wherein--.

In claim 23, column 80, line 41, "substituents are selected" should read --substituents selected--.

In claim 32, column 81, line 15, "$R^{17}$ selected" should read --$R^{17}$ is selected--.

In claim 32, column 81, line 15, "hydrogen, and" should read --hydrogen and--.

In claim 35, column 81, line 25, "hydrogen, and" should read --hydrogen and--.

In claim 49, column 82, line 10, "48." should read --2.--.

In claim 56, column 82, line 34, "disease, and" should read --disease and--.

In claim 57, column 82, line 35, "treating a Parkinson's" should read --treating Parkinson's--.

In claim 63, column 82, line 64, "(1R)-cyclohexyloxycaxbonyloxyethyl" should read --(1R)-cyclohexyloxycarbonyloxyethyl--.

UNITED STATES PATENT AND TRADEMARK OFFICE
CERTIFICATE OF CORRECTION

PATENT NO.       : 7,101,912 B2
APPLICATION NO.  : 10/728942
DATED            : September 5, 2006
INVENTOR(S)      : Jia-Ning Xiang et al.

It is certified that error appears in the above-identified patent and that said Letters Patent is hereby corrected as shown below:

In claim 63, column 83, lines 32-33, "(S)-3-(3,4-Bis-ethoxycarbonyloxy)pheny1-2-hydrazino-2-methylpropionic" should read --(S)-3-(3,4-Bis-ethoxycarbonyloxy)phenyl-2-hydrazino-2-methylpropionic--.

Signed and Sealed this

Twenty-sixth Day of December, 2006

JON W. DUDAS
*Director of the United States Patent and Trademark Office*